United States Patent
Song et al.

(10) Patent No.: US 11,759,528 B2
(45) Date of Patent: *Sep. 19, 2023

(54) PEG LINKER AND LIGAND DRUG CONJUGATE

(71) Applicant: JenKem Technology Co., Ltd. (Beijing), Beijing (CN)

(72) Inventors: Yanping Song, Beijing (CN); Wen Li, Beijing (CN); Jinliang Wang, Beijing (CN); Yan Liu, Beijing (CN); Kun Zheng, Beijing (CN); Meina Lin, Beijing (CN); Zhen Wei, Beijing (CN); Zewang Feng, Beijing (CN); Xuan Zhao, Beijing (CN)

(73) Assignee: JENKEM TECHNOLOGY CO., LTD. (BEIJING), Beijing (CN)

( * ) Notice: Subject to any disclaimer, the term of this patent is extended or adjusted under 35 U.S.C. 154(b) by 1026 days.

This patent is subject to a terminal disclaimer.

(21) Appl. No.: 16/213,485

(22) Filed: Dec. 7, 2018

(65) Prior Publication Data

US 2019/0117790 A1    Apr. 25, 2019

Related U.S. Application Data

(63) Continuation of application No. PCT/CN2016/090397, filed on Jul. 19, 2016.

(30) Foreign Application Priority Data

Jun. 7, 2016  (CN) .......................... 201610398765.4

(51) Int. Cl.
  *A61K 47/68* (2017.01)
  *A61K 31/4745* (2006.01)
  (Continued)

(52) U.S. Cl.
  CPC ........ *A61K 47/6855* (2017.08); *A61K 31/436* (2013.01); *A61K 31/4745* (2013.01);
  (Continued)

(58) Field of Classification Search
  None
  See application file for complete search history.

(56) References Cited

U.S. PATENT DOCUMENTS

| | | | | |
|---|---|---|---|---|
| 2010/0316656 | A1* | 12/2010 | Bouchard | C07D 519/00 540/496 |
| 2016/0082119 | A1* | 3/2016 | Gonzalez | A61K 47/645 514/19.5 |
| 2018/0161446 | A1* | 6/2018 | Xiang | A61K 47/6803 |

FOREIGN PATENT DOCUMENTS

| | | |
|---|---|---|
| CN | 1706865 A | 12/2005 |
| CN | 1995094 A | 7/2007 |

(Continued)

OTHER PUBLICATIONS

Wangler et al., ChemBioChem 2010, 11, 2168-2181 (Year: 2010).*
(Continued)

*Primary Examiner* — Karl J Puttlitz
(74) *Attorney, Agent, or Firm* — FLENER IP & BUSINESS LAW; Zareefa B. Flener

(57) ABSTRACT

A PEG linker as represented by formula (I), wherein n and m are respectively an integer from 1 to 7, providing the PEG linker with 1 to 49 linking sites. A ligand drug conjugate as represented by formula (II). The conjugate uses the PEG linker to increase a drug loading capacity and drug loading diversity, thereby improving pharmaceutical efficacy.

$$Y1\text{-}PEG1\text{-}\{R^1\text{-}PEG2\text{-}\{Y4\}_n\}_m \quad (I)$$

$$TM\text{-}\{R^2\text{-}PEG1\text{-}\{R^1\text{-}PEG2\text{-}\{R^3\text{-}A'\text{-}drug\}_n\}_m\}_l \quad (II)$$

1 Claim, 2 Drawing Sheets

(51) Int. Cl.

| | | |
|---|---|---|
| *C08G 65/48* | (2006.01) | |
| *A61P 37/02* | (2006.01) | |
| *A61P 31/00* | (2006.01) | |
| *A61P 35/00* | (2006.01) | |
| *C08G 65/334* | (2006.01) | |
| *C07C 69/708* | (2006.01) | |
| *A61K 47/60* | (2017.01) | |
| *C08G 65/333* | (2006.01) | |
| *A61K 31/436* | (2006.01) | |
| *A61K 47/10* | (2017.01) | |
| *A61K 47/34* | (2017.01) | |
| *C07C 59/125* | (2006.01) | |
| *C07C 247/04* | (2006.01) | |
| *C07C 309/65* | (2006.01) | |
| *C07D 207/452* | (2006.01) | |
| *C07D 207/46* | (2006.01) | |
| *C07K 16/28* | (2006.01) | |
| *C07K 16/32* | (2006.01) | |

(52) U.S. Cl.
CPC ............... *A61K 47/10* (2013.01); *A61K 47/34* (2013.01); *A61K 47/60* (2017.08); *A61K 47/6803* (2017.08); *A61K 47/6849* (2017.08); *A61K 47/6883* (2017.08); *A61P 31/00* (2018.01); *A61P 35/00* (2018.01); *A61P 37/02* (2018.01); *C07C 59/125* (2013.01); *C07C 69/708* (2013.01); *C07C 247/04* (2013.01); *C07C 309/65* (2013.01); *C07D 207/452* (2013.01); *C07D 207/46* (2013.01); *C07K 16/2809* (2013.01); *C07K 16/32* (2013.01); *C08G 65/334* (2013.01); *C08G 65/3332* (2013.01); *C08G 65/3344* (2013.01); *C08G 65/33303* (2013.01); *C08G 65/33317* (2013.01); *C08G 65/48* (2013.01); *C07K 2317/94* (2013.01)

(56) References Cited

FOREIGN PATENT DOCUMENTS

| | | | |
|---|---|---|---|
| CN | 101108895 A | 1/2008 | |
| CN | 102711837 A | 10/2012 | |
| CN | 103083680 A | 5/2013 | |
| CN | 104448296 A | 3/2015 | |
| CN | 104497303 A | 4/2015 | |
| WO | 2016050209 | * | 4/2016 |

OTHER PUBLICATIONS

Yoon et al., Small (2013), 9(2), 284-293 CODEN: SMALBC; ISSN: 1613-6810 (Year: 2013).*
Database Caplus Chemical Abstracts Service, Columbus, Ohio, US; Database Accession No. 2012:1261827 Abstract of Yoon et al., Small (2013), 9(2), 284-293 CODEN: SMALBC; ISSN: 1613-6810 (Year: 2013).*
Certified Copy of CN201510313585.7 (Year: 2015).*
Lu et al., Int. J. Mol. Sci. 2016, 17, 561 (Year: 2016).*
Machine Translation of WO201605020; downloaded Jan. 31, 2023 from https://patentimages.storage.googleapis.com/91/6d/e0/672bffaeaaadb4/WO2016050209A1.pdf (Year: 2016).*
Database Caplus Chemical Abstracts Service, Columbus, Ohio, US; Database Accession No. 2015:683933, Abstractor WO 2016050209; Xiamen Sinopeg Biotech Co., Ltd., Peop. Rep. China Apr. 22, 2016 (Year: 2016).*
The State Intellectual Property Office of People's Republic of China, First Office Action, Application No. or Publication No. 201610398765.4, Date of filing: Jun. 7, 2016; dated May 9, 2019.
The State Intellectual Property Office of People's Republic of China, The Second Office Action, Application No. or Publication No. 201610398765.4, dated Dec. 26, 2019.
International Search Report, International application No. PCT/CN2016/090397, Date of the actual completion of the international search dated Mar. 6, 2017.
Patent Cooperation Treaty Written Opinion of the International Searching Authority, International application No. PCT/CN2016/090397, dated Mar. 14, 2017.
Kevin J. Hamblett et al., Effects of Drug Loading on the Antitumor Activity of a Monoclonal Antibody Drug Conjugate, American Association for Cancer Research Journals, Clinical Cancer Research, Oct. 15, 2002, vol. 10, pp. 7063-7070.
Jagath R. Junutula, et al., Engineered Thio-Trastuzumab-DM1 Conjugate with an Improved Therapeutic Index to Target Human Epidermal Growth Factor Receptor 2-Positive Breast Cancer, American Association for Cancer Research Journals, Clinical Cancer Research, Oct. 1, 2020, vol. 16 Issue 19, pp. 4769-4778.

* cited by examiner

PEG LINKER AND LIGAND DRUG CONJUGATE

CROSS-REFERENCE TO RELATED APPLICATION

This application is a continuation application of International patent application No. PCT/CN2016/090397, filed on Jul. 19, 2016, which claims the benefit and priority of Chinese patent application No. CN201610398765.4, filed on Jun. 7, 2016, each of which is incorporated herein by reference in its entirety and for all purposes.

FIELD OF THE INVENTION

The present invention relates to the field of Ligand Drug Conjugates (LDC), in particular to a ligand drug conjugate having a PEG linker and a pharmaceutical composition comprising the same, and a preparation method and application thereof.

BACKGROUND OF THE INVENTION

The advent of Antibody-Drug Conjugates (ADC) has revolutionized the treatment of cancer. In the ADC, a biologically active small molecule drug is linked to a monoclonal antibody (MAb) via a linker, and the MAb, as a carrier, may deliver the small molecule drug to target cells, which not only improves the anticancer effect of the MAb, but also reduces the toxicity of the small molecule drug. Currently, two commercial ADCs, Adcetris® and Kadcyla®, have achieved good results in the treatment of Hodgkin lymphoma and breast cancer. Among them, in Adcetris®, the sulfydryl of cysteine in the antibody is coupled with a maleimide linker, and in Kadcyla®, the amino of lysine in the antibody forms an amide bond with a linker.

In the current study, there is a hypothesis that the higher the drug loading capacity, the better the pharmaceutical efficacy, while the actual pharmaceutical efficacy results in vivo are contrary to this hypothesis. Hamblett et al. found that auristatin coupled with four or eight drugs showed similar activity in mouse model (Hamblett et al., Clinical Cancer Res. 10: 7063-70, 2004). Hamblett et al. further reported that the higher the loading capacity of ADC, the easier it was to be cleared in animals, and that this rapid clearance trait appeared to be PK dependent in a drug conjugate with high loading capacity compared to a drug conjugate with a low loading capacity. Hamblett et al. also found that the drug conjugate with a high loading capacity showed a lower drug maximum tolerated dose (MTD) in a mouse model, which in turn led to a narrower therapeutic window. Studies have reported that ADCs carrying two drug molecules have better PK characteristics and therapeutic window compared to ADCs carrying four drug molecules (Junutula et al., Clinical Cancer Res. 16: 4769, 2010).

Linkers play a fundamental role in determining the therapeutic potential of ADCs. In the case of effective delivery of hydrophobic cytotoxic drugs, if the linker itself is hydrophobic, it may increase the aggregation of the conjugate or reduce the affinity of the antibody, especially at high drug loading capacity. Moreover, drug-resistant tumor cells may limit the activity of ADCs, most of which is caused by the increase in the expression or activity of drug transporters, which accelerates the efflux of hydrophobic compounds. Therefore, one of the challenges in the design and development of ADCs is the generation of a hydrophilic linker suitable for coupling of an antibody to a drug. By using this hydrophilic linker, a higher drug loading capacity can be achieved and a higher concentration of toxin can be delivered to target cells.

By using a PEG linker in a ligand drug conjugate, the present invention is capable of masking the hydrophobicity of the drug or conjugate, thereby allowing the conjugate to carry more drug molecules and maintain pharmacokinetic characteristics and other characteristics consistent with the conjugate with low drug loading capacity. In addition, the ligand drug conjugate is further designed to ensure that the drug molecule can be selected for low toxicity analysis under high drug loading capacity, thereby effectively preventing damage to the individual due to drug release. Furthermore, the linking sites in the PEG linker of the present invention are uniformly distributed, thereby avoiding the problem of reduced pharmaceutical efficacy caused by hydrophobic aggregation brought by local dense distribution of drugs (mostly hydrophobic).

SUMMARY OF THE INVENTION

An object of the present invention is to provide a PEG linker with a high loading capacity and a high purity.

Another object of the present invention is to provide a ligand drug conjugate with a high loading capacity and a low toxicity, and a pharmaceutically acceptable salt and a pharmaceutical composition thereof.

Still another object of the present invention to provide a preparation and use of a ligand drug conjugate with a high loading capacity and a low toxicity.

In order to achieve the above objects, in one aspect, the present invention provides a PEG linker having a structure represented by general formula (I):

$$Y1\text{-}PEG1\text{-}\{R^1\text{-}PEG2\text{-}\{Y4\}_n\}_m \qquad (I)$$

wherein,

PEG1 and PEG2 are the same or different polyethylene glycol residues;

m is an integer from 1 to 7, and preferably, m is an integer from 2 to 7;

n is an integer from 1 to 7, and preferably, n is an integer from 2 to 7;

$R^1$ is a linking unit linking PEG1 to PEG2;

Y1 has a structure of Z1-X1-, and Y4 has a structure of —X4-Z4;

wherein, X1 and X4 are independently selected from the group consisting of —$(CH_2)_i$—, —$(CH_2)_i$NH—, —$(CH_2)_i$OCOO—, —$(CH_2)_i$OCONH—, —$(CH_2)_i$NHCONH—, —$(CH_2)_i$NHCO—, —OC$(CH_2)_i$COO—, —$(CH_2)_i$COO— and —$(CH_2)_i$ONH—, i is an integer from 0 to 10, and preferably, i is 0, 1 or 2;

Z1 is selected from the group consisting of succinimido

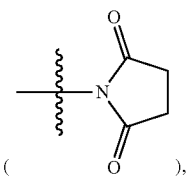

sulfydryl, carboxyl, propionic acid group (2-carboxyethyl,

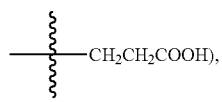

aldehyde group, acryloxy

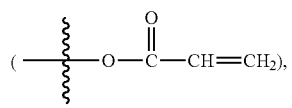

glutaric acid group (4-carboxybutyryloxy,

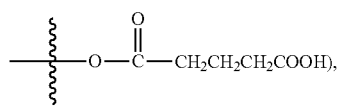

maleimido

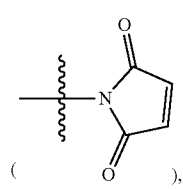

N-hydroxy-succinimido

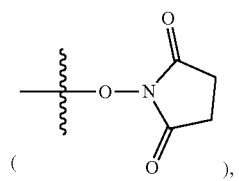

N-hydroxy-glutarimide

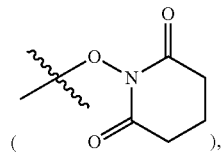

succinimide carbonate group

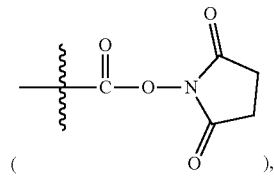

succinimide acetate group

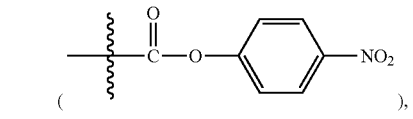 [SMILES: *C(=O)Oc1ccc([N+](=O)[O-])cc1]

succinimide propionate group (structure)

succinimide succinate group (structure)

imidate group (structure)

R' is a suitable group such as an alkyl group, specifically, e.g., methyl, ethyl, etc.), p-nitrophenyl carbonate group (structure)

cyanuric chloride group

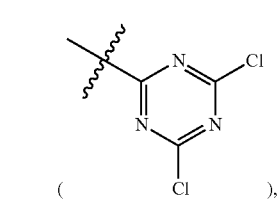

o-dithiopyridinyl

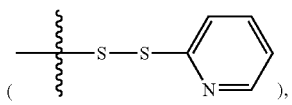

thioester group

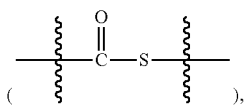

hydrazide group

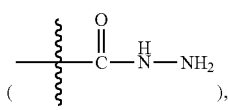

isocyanato

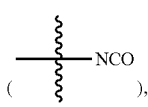

isothiocyano

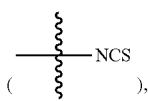

and vinyl sulfone group

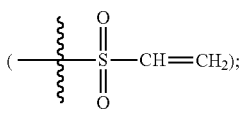

and

Z4 is carboxyl, hydroxyl or carbonyl.

In an embodiment of the present invention, the PEG linker has 1 to 49 linking sites and can be coupled to 1 to 49 drug molecules, for example, one drug molecule when m is 1 and n is 1; 2 drug molecules when m is 1 and n is 2; 4 drug molecules when m is 2 and n is 2; 6 drug molecules when m is 2 and n is 3; 9 drug molecules when m is 3 and n is 3; 21 drug molecules when m is 3 and n is 7; and 49 drug molecules when m is 7 and n is 7.

In a specific embodiment of the present invention, preferably, m is an integer from 2 to 7 (i.e., 2, 3, 4, 5, 6, or 7), and n is an integer from 2 to 7 (i.e., 2, 3, 4, 5, 6, or 7). The PEG linker is capable of coupling 2 to 49 drug molecules, and more preferably, 4 to 49, 6 to 42, 9 to 36, 12 to 30, 15 to 25, or 21 to 24 drug molecules.

In an embodiment of the present invention, in the PEG linker represented by general formula (I), one form of said $R^1$, the linking unit that links PEG1 to PEG2, is thiol-reactive form, and the reactive end groups are independently selected from the group consisting of sulfydryl and sulfydryl-reactive group, and the sulfydryl-reactive group is capable of reacting with sulfydryl to form a thioether bond or a disulfide bond, including but not limited to: maleimido, glutaric acid group, vinyl sulfone group, haloacetamido, dithiopyridinyl, thiosulfonate group, ethyleneimine group, aziridinyl group, and aminosulfonyl group; and preferably, the sulfydryl-reactive group is selected from the group consisting of maleimido, vinyl sulfone group, and haloacetamido.

In another specific embodiment of the present invention, another form of said $R^1$, the linking unit that links the PEG1 and PEG2, is a form obtained by a click reaction, and the reactive end groups are independently selected from the group consisting of azido and alkynyl.

The PEG linker of the present invention can be used in the preparation of a ligand drug conjugate.

In another aspect, the present invention provides a ligand drug conjugate having a structure represented by general formula (II):

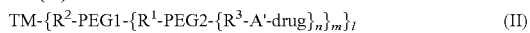

wherein,

TM is a ligand unit;

PEG1 and PEG2 are the same or different polyethylene glycol residues;

l is an integer from 1 to 10 (i.e., 1, 2, 3, 4, 5, 6, 7, 8, 9, or 10);

m is an integer from 1 to 7 (i.e., 1, 2, 3, 4, 5, 6, or 7);

n is an integer from 1 to 7 (i.e., 1, 2, 3, 4, 5, 6, or 7);

$R^1$ is a spacer that may or may not be present;

$R^1$ is a linking unit linking PEG1 to PEG2;

$R^2$ is a coupling unit linking the ligand unit to PEG1; and $R^3$ is a linking unit linking PEG2 to the spacer A' or a drug.

In an embodiment of the present invention, the ligand unit has 1 to 10 linking sites, and optionally, the PEG linker can be linked to any one or more of the linking sites of the ligand unit. For example, when l is 1, any linking site of the ligand unit may be linked to one PEG linker molecule; and when l is 2, any two linking sites of the ligand unit may be respectively linked to two PEG linker molecules.

In a specific embodiment of the present invention, preferably, l is an integer from 1 to 8, more preferably, l is an integer from 1 to 4, and most preferably, l is 1, 2 or 3.

In an embodiment of the present invention, when one PEG linker molecule is present, the ligand drug conjugate is capable of coupling from 1 to 49 drug molecules, for example, one drug molecule when m is 1 and n is 1; 2 drug molecules when m is 1 and n is 2; 4 drug molecules when m is 2 and n is 2; 6 drug molecules when m is 2 and n is 3; 9 drug molecules when m is 3 and n is 3; 21 drug molecules when m is 3 and n is 7; and 49 drug molecules when m is 7 and n is 7. When two PEG linker molecules are present, the ligand drug conjugate is capable of coupling from 2 to 98 drug molecules. And, when three PEG linker molecules are present, the ligand drug conjugate is capable of coupling from 3 to 147 drug molecules.

In a specific embodiment of the present invention, preferably, n is an integer from 1 to 3 (i.e., 1, 2, or 3), m is an integer from 2 to 7 (i.e., 2, 3, 4, 5, 6, or 7), and n is an integer from 2 to 7 (i.e., 2, 3, 4, 5, 6, or 7); and the ligand drug conjugate is capable of coupling from 2 to 147 drug molecules, and more preferably, 3 to 147, 6 to 126, 9 to 108, 15 to 75, or 21 to 63 drug molecules.

In an embodiment of the present invention, in the ligand drug conjugate represented by general formula (II), preferably, the TM ligand unit is a disease targeting unit, and the disease targeting moiety may be an antibody, a protein, a polypeptide or an oligonucleotide, wherein the antibody includes a monoclonal antibody and a polyclonal antibody, preferably a monoclonal antibody, and more preferably an internalizing monoclonal antibody. In the present invention, the antibody may be in the form of, for example, a chimeric antibody, a humanized antibody, a human antibody, an antibody fragment capable of binding to an antigen (Fab, Fab', F(ab)$_2$, and F(ab')$_2$), a subfragment (single-stranded construct), or an antibody Fc fusion protein, etc.

In a specific embodiment of the present invention, preferably, the monoclonal antibody is reactive with an antigen associated with cancer, malignant cells, infectious organisms or autoimmune diseases, or an epitope thereof.

In a specific embodiment of the present invention, preferably, the monoclonal antibody is selected from the group consisting of an anti-HER2 antibody, an anti-EGFR antibody, an anti-PMSA antibody, an anti-VEGFR antibody, an anti-CD30 antibody, an anti-CD22 antibody, an anti-CD56 antibody, an anti-CD29 antibody, an anti-GPNMB antibody, an anti-CD138 antibody, an anti-CD74 antibody, an anti-ENPP3 antibody, an anti-Nectin-4 antibody, an anti-EGFRVIII antibody, an anti-SLC44A4 antibody, an anti-mesothelin antibody, an anti-ET8R antibody, an anti-CD37 antibody, an anti-CEACAM5 antibody, an anti-CD70 antibody, an anti-MUC16 antibody, an anti-CD79b antibody, an anti-MUC16 antibody, and an anti-Muc1 antibody.

In a specific embodiment of the present invention, preferably, the antigen is selected from the group consisting of HER-2/neu, carbonic anhydrase IX, B7, CCCL19, CCCL21, CSAp, BrE3, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM-6, alpha fetoprotein (AFP), VEGF, ED-B fibronectin, EGP-1, EGP-2, EGF receptor (ErbB1), ErbB2, ErbB3, factor H, FHL-1, Flt-3, folate receptor, Ga 733, GROB, HMGB-1, hypoxia-inducible factor (HIF), HM1.24, insulin-like growth factor (ILGF), IFN-γ, IFN-α, IFN-β, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, ganglioside, HCG, HLA-DR, CD66a-d, MAGE, mCRP, MCP-1, MIP-1A, MIP-1B, macrophage migration inhibitory factor (MIF), MUC1, MUC2, MUC3, MUC4, MUC5, placental growth factor (PIGF), PSA, PSMA, PSMA dimer, PAM4 antigen, NCA-95, NCA-90, A3, A33, Ep-CAM, KS-1, Le(y), mesothelin, S100, tenascin, TAC, Tn antigen, Thomas-Friedenreich antigen, tumor necrosis antigen, tumor angiogenic antigen, TNF-α, TRAIL receptor (R1 and R2), VEGFR, RANTES, T101, cancer stem cell antigen, complement factors C3, C3a, C3b, C5a, and C5, and oncogene products, etc.

In an embodiment of the present invention, in the ligand drug conjugate represented by general formula (II), said A', the spacer, is selected from a chemically labile linker (such as hydrazone and disulfide linkers), an enzymatic catalysis linker (such as a peptide linker, a β-glucosiduronide linker, a carbonate linker labile to esterase), a non-cleavable linker (such as succinimide-thioether bond), and one or more of amino acid residues which are the same or not the same or derivatives thereof; and the amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; and preferably, the amino acid is selected from the group consisting of aspartic acid, glutamic acid, glycine, isoleucine, leucine, phenylalanine and valine.

In a specific embodiment of the present invention, preferably, said A', the spacer, is a carbonate residue, a β-glucosiduronide residue, or one or more of amino acid residues which are the same or not the same or derivatives thereof.

In a specific embodiment of the present invention, preferably, the amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, etc. More preferably, the amino acid is selected from the group consisting of aspartic acid, glutamic acid, glycine, isoleucine, leucine, phenylalanine and valine.

In a specific embodiment of the present invention, preferably, said A' is a carbonate residue, a β-glucosiduronide residue, a proline residue, an aspartic acid-valine residue, or a glutamic acid-valine residue.

In a specific embodiment of the present invention, in the ligand drug conjugate represented by general formula (II), one form of said $R^1$, the linking unit that links PEG1 to PEG2, is thiol-reactive form, and the reactive end groups are independently selected from the group consisting of sulfydryl and sulfydryl-reactive group, and the sulfydryl-reactive group is capable of reacting with sulfydryl to form a thioether bond or a disulfide bond, including but not limited to: maleimido, glutaric acid group, vinyl sulfone group, haloacetamido, dithiopyridinyl, thiosulfonate group, ethyleneimine group, aziridinyl group, and aminosulfonyl group; and preferably, the sulfydryl-reactive group is selected from the group consisting of maleimido, vinyl sulfone group, and haloacetamido.

In another specific embodiment of the present invention, in the ligand drug conjugate represented by general formula (II), another form of said $R^1$, the linking unit that links PEG1 to PEG2, is a form obtained by a click reaction, and the reactive end groups are independently selected from the group consisting of azido and alkynyl.

In an embodiment of the present invention, in the ligand drug conjugate represented by general formula (II), said $R^2$, the coupling unit that links the ligand unit to PEG1, has a structure of —B-A-, wherein:

A is selected from the group consisting of —(CH$_2$)$_i$—, —(CH$_2$)$_i$NH—, —(CH$_2$)$_i$OCOO—, —(CH$_2$)$_i$OCONH—, —(CH$_2$)$_i$NHCONH—, —(CH$_2$)$_i$NHCO—, —OC(CH$_2$)$_i$COO—, —(CH$_2$)$_i$COO— and —(CH$_2$)$_i$CONH—, i is an integer from 0 to 10; and preferably, i is 0, 1 or 2;

B is selected from the group consisting of succinimido, carboxyl, sulfydryl, succinimide carbonate, succinimide acetate, succinimide propionate, succinimide succinate, N-hydroxy-succinimido, N-hydroxy-glutarimide, imino acid ester group, p-nitrophenyl carbonate, cyanuric chloride group, o-dithiopyridinyl, propionic acid group, aldehyde group, thioester group, acryloxy, glutaric acid group, hydrazide group, isocyanato, isothiocyano, and vinyl sulfone group.

In a specific embodiment of the present invention, in the ligand drug conjugate represented by general formula (II), said $R^2$, the coupling unit that links the ligand unit to PEG1, is formed by reacting the amino of the ligand unit with the reactive end group of PEG1 to form an amide bond, and the reactive end group of PEG1 is selected from the group consisting of succinimidyl succinate (SS) group, succinimidyl carbonate (SC) group, mPEG-imidate group

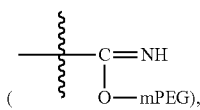

p-nitrophenyl carbonate (NPC) group, succinimidyl propionate (SPA) group and cyanuric chloride group.

It is known to those skilled in the art that common groups on the ligand unit which can react with PEG1 further include: —NH—, OH—, SH—, COOH—, in addition to guanidino of arginine, imidazolyl of histidine, glycosyl of glycoprotein (comprising aldehyde group, hydroxyl, primary amino, carboxyl, phosphate group, etc.).

In an embodiment of the present invention, in the ligand drug conjugate represented by general formula (II), said $R^3$, the linking unit that links PEG2 to the spacer A' or the drug, is selected from the group consisting of —(CH$_2$)$_i$OCOO—, —(CH$_2$)$_i$OCONH—, —(CH$_2$)$_i$NHCONH—, —(CH$_2$)$_i$NHCO—, —OC(CH$_2$)$_i$COO—, —(CH$_2$)$_i$COO— and —(CH$_2$)$_i$CONH—, i is an integer from 0 to 10; preferably, i is 0, 1 or 2.

In an embodiment of the present invention, in the ligand drug conjugate represented by general formula (II), the drug is selected from the group consisting of irinotecan, topotecan, belotecan, exatecan, lurtotecan, diflomotecan, gimatecan, karenitecin, doxorubicin (DOX), epirubicin, morpholinyldoxorubicin, cyanomorpholinyldoxorubicin, 2-pyrrolinyldoxorubicin, camptothecin (CPT), 10-hydroxycamptothecin, SN-38, 9-aminocamptothecin, 9-nitrocamptothecin, taxane, geldanamycin, ansamycin, and epothilone.

In a specific embodiment of the present invention, preferably, in the ligand drug conjugate represented by general formula (II), the drug is selected from the group consisting of irinotecan, topotecan, belotecan, exatecan, lurtotecan, diflomotecan, gimatecan, karenitecin, camptothecin (CPT), 10-hydroxycamptothecin, SN-38, 9-aminocamptothecin, and 9-nitrocamptothecin. More preferably, the drug is irinotecan.

In a specific embodiment of the present invention, preferably, in the ligand drug conjugate represented by general formula (II), the drug is a drug with a low toxicity. Specifically, when the drug is a drug with low toxicity, the ligand drug conjugate contains more drug molecules.

In a specific embodiment of the present invention, the ligand drug conjugate is selected from the group consisting of APEGA-2 (TM-NHS-4ARMPEG1-(MAL)3-(SH)-PEG2-Irinotecan), APEGA-4 (TM-NHS-4ARMPEG1-(MAL)3-(SH)-4ARMPEG2-(Irinotecan)3), APEGA-5 (TM-NHS-4ARMPEG1-(MAL)3-(SH)-8ARMPEG2-(Irinotecan)7), and APEGA-6 (TM-NHS-8ARMPEG1-(MAL)7-(SH)-4ARMPEG2-(Irinotecan)3), the structures of which are as follows:

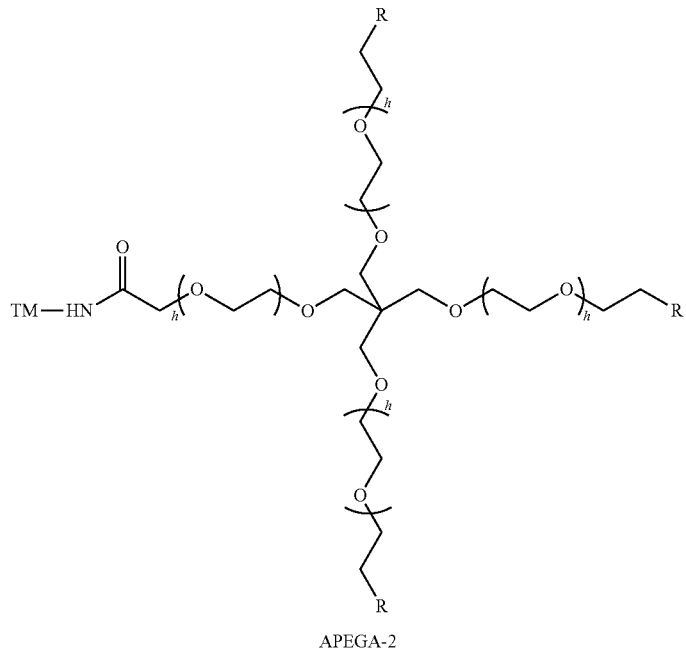

APEGA-2

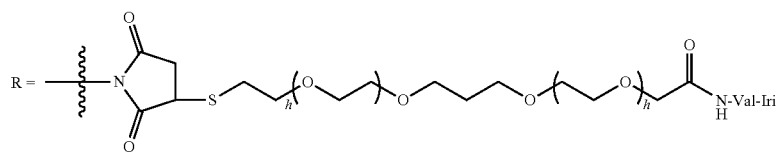

-continued
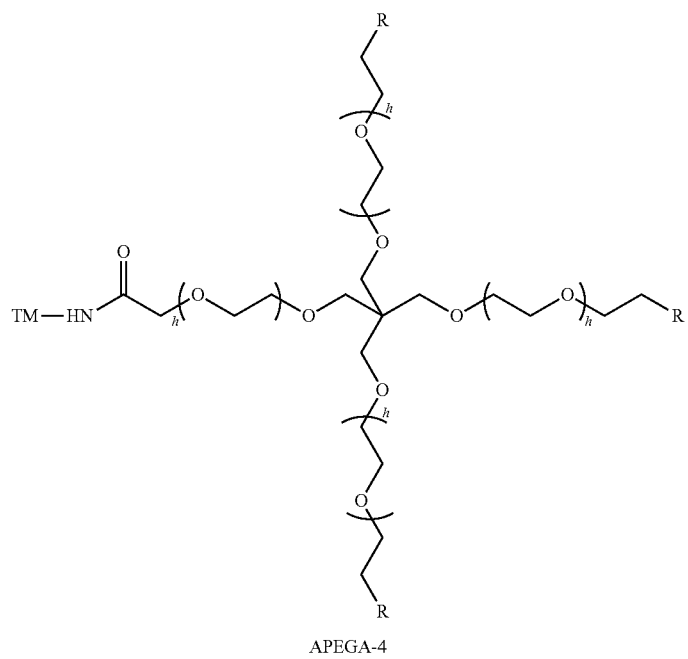
APEGA-4
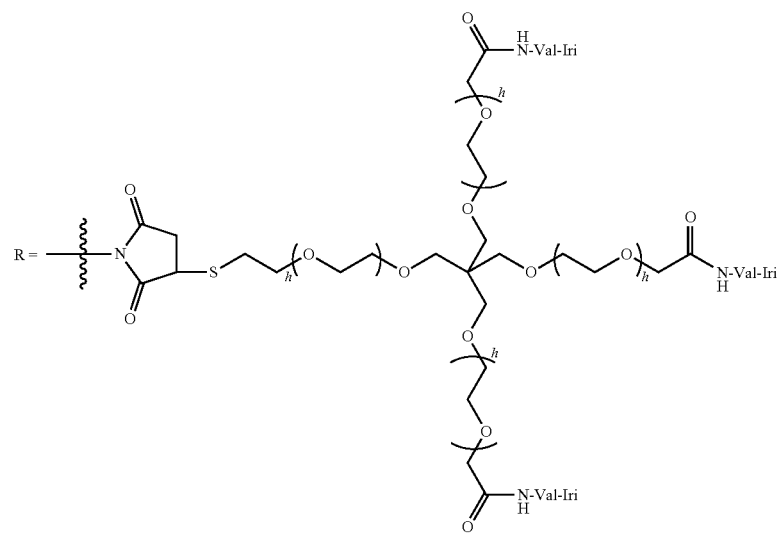

-continued
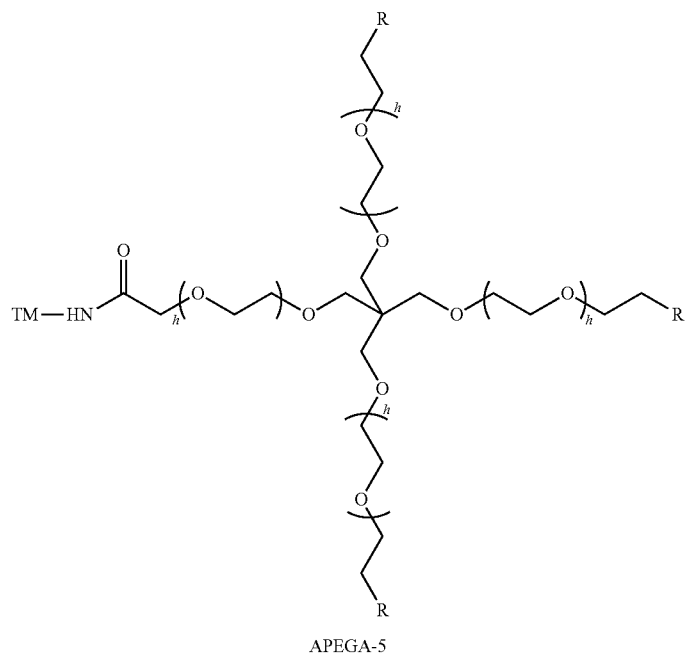
APEGA-5
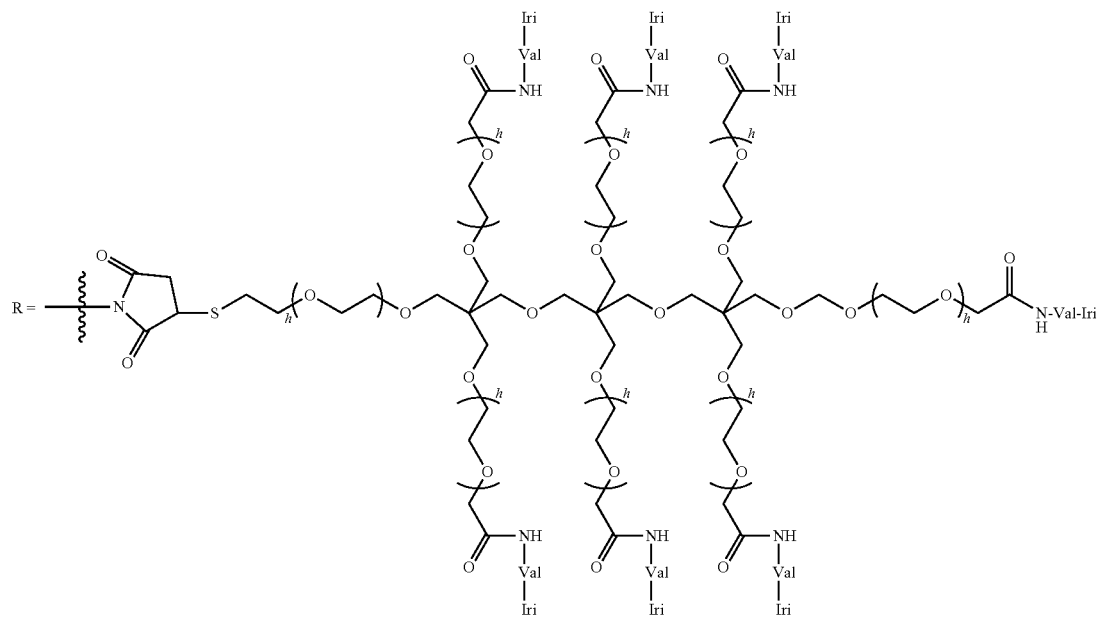

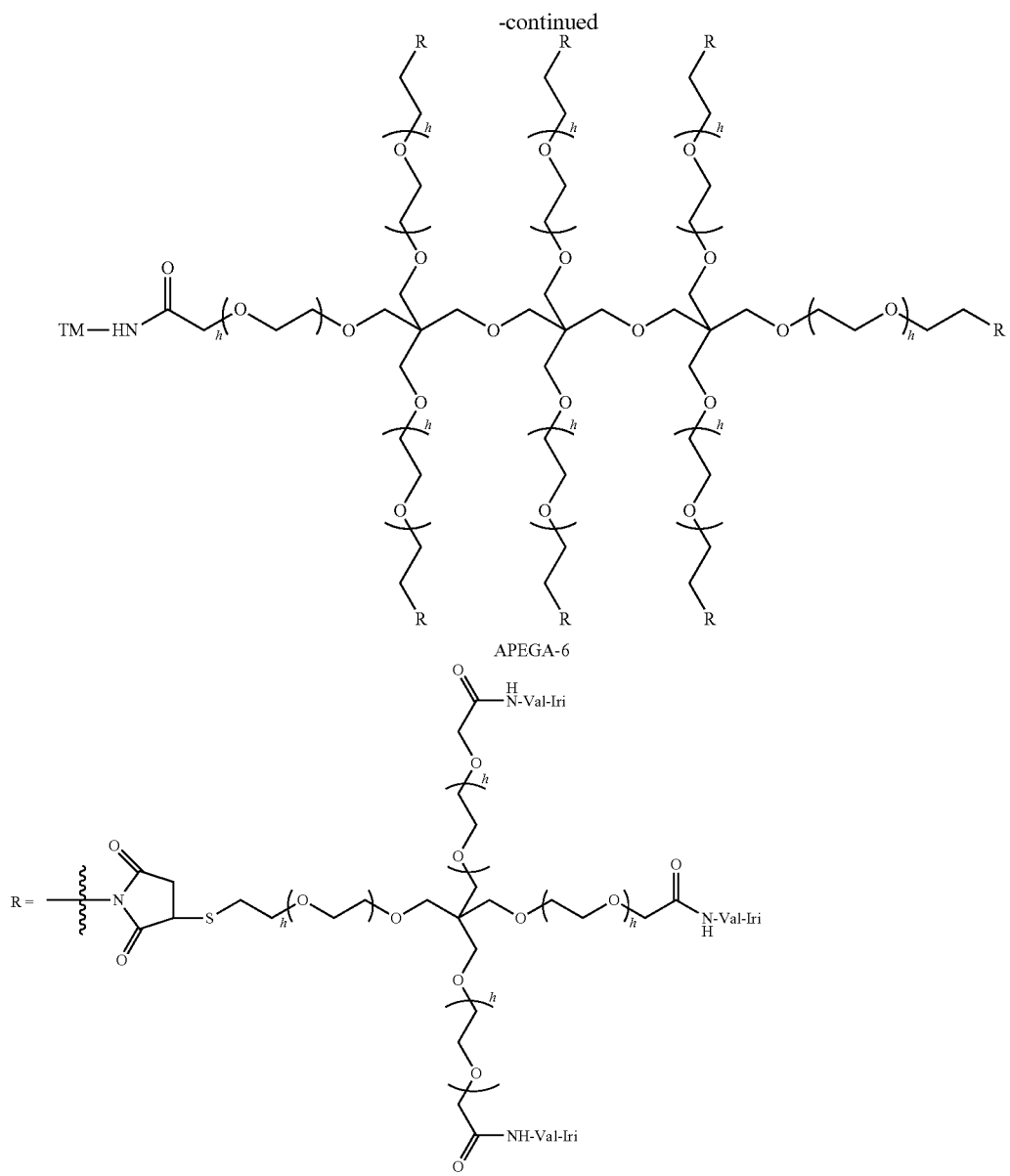

APEGA-6

Wherein, in the above structures, TM is a ligand unit, preferably, TM is a monoclonal antibody; Val is proline; Iri is irinotecan; h may be the same or not the same, and each independently is an integer selected from 1 to 240, preferably, an integer from 1 to 120, and more preferably an integer from 1 to 60.

In an embodiment of the present invention, in the PEG linker represented by general formula (I) or the ligand drug conjugate represented by general formula (II), said PEG1 is a polyethylene glycol residue having definite monomer units from 1 to 240, and preferably a polyethylene glycol residue having definite monomer units from 1 to 120.

In an embodiment of the present invention, in the PEG linker represented by general formula (I) or the ligand drug conjugate represented by general formula (II), said PEG1 is a linear, Y-type, or multi-branched polyethylene glycol residue, including, for example, a linear double-ended PEG, a Y-type PEG, a 4-arm branched PEG, a 6-arm branched PEG, or an 8-arm branched PEG, etc., and preferably a Y-type polyethylene glycol residue, or a multi-branched polyethylene glycol residue. The molecular weight of PEG is 1 to 100 KDa, such as, 1 to 20 KDa (specifically 1, 2, 3, 4, 5, 6, 7, 8, 9, 10, 11, 12, 13, 14, 15, 16, 17, 18, 19, or 20 KDa), 20 to 50 KDa (specifically 20, 25, 30, 35, 40, 45, or 50 KDa), or 50 to 100 KDa (specifically 50, 55, 60, 65, 70, 75, 80, 85, 90, 95, or 100 KDa), etc.; and preferably, the molecular weight of PEG is 1 to 20 KDa, more preferably 1 to 10 KDa, for example, 1 to 5 KDa, or 5 to 10 KDa.

In a specific embodiment of the present invention, said PEG1 is a linear polyethylene glycol residue having a structure shown below:

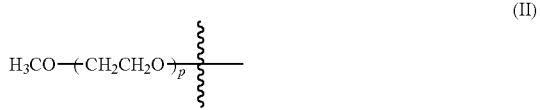

(II)

wherein, p is an integer from 1 to 240, preferably an integer from 1 to 120.

In a specific embodiment of the present invention, said PEG1 is a Y-type polyethylene glycol residue having a structure of general formula (III):

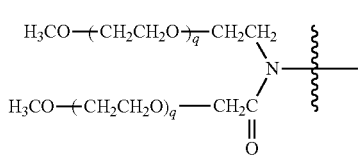
(III)

wherein, q is an integer from 1 to 120, preferably an integer from 1 to 60.

In a specific embodiment of the present invention, said PEG1 is a multi-branched polyethylene glycol residue having a structure of general formula (IV):

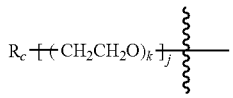
(IV)

wherein, k is an integer from 1 to 80, preferably an integer from 1 to 40;

j is an integer from 3 to 8;

$R_c$ is a core molecule of the multi-branched polyethylene glycol, and $R_c$ is selected from the group consisting of residues of pentaerythritol, oligo-pentaerythritol, methyl glucoside, sucrose, diglycol, propanediol, glycerol, and polyglycerol, and preferably, $R_c$ is selected from the group consisting of residues of pentaerythritol, dipentaerythritol and tripentaerythritol.

In an embodiment of the present invention, in the PEG linker represented by general formula (I) or the ligand drug conjugate represented by general formula (II), said PEG2 is a polyethylene glycol residue having definite monomer units from 1 to 240, preferably a polyethylene glycol residue having definite monomer units from 1 to 120.

In an embodiment of the present invention, in the PEG linker represented by general formula (I) or the ligand drug conjugate represented by general formula (II), said PEG2 is a linear, Y-type, or multi-branched polyethylene glycol residue, including, for example, a linear double-ended PEG, a Y-type PEG, a 4-arm branched PEG, a 6-arm branched PEG, or an 8-arm branched PEG, etc., preferably a Y-type polyethylene glycol residue, or a multi-branched polyethylene glycol residue. The molecular weight of PEG is 1 to 100 KDa, such as, 1 to 20 KDa (specifically 1, 2, 3, 4, 5, 6, 7, 8, 9, 10, 11, 12, 13, 14, 15, 16, 17, 18, 19, or 20 KDa), 20 to 50 KDa (specifically 20, 25, 30, 35, 40, 45, or 50 KDa), or 50 to 100 KDa (specifically 50, 55, 60, 65, 70, 75, 80, 85, 90, 95, or 100 KDa), etc.; and preferably, the molecular weight of PEG is 1 to 20 KDa, more preferably 1 to 10 KDa, for example, 1 to 5 KDa, or 5 to 10 KDa.

In a specific embodiment of the present invention, said PEG2 is a linear polyethylene glycol residue having a structure of general formula (II):

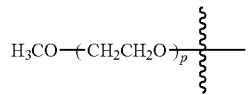
(II)

wherein, p is an integer from 1 to 240, preferably an integer from 1 to 120.

In a specific embodiment of the present invention, said PEG2 is a Y-type polyethylene glycol residue having a structure of general formula (III):

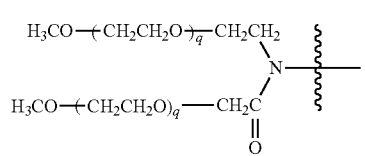
(III)

wherein, q is an integer from 1 to 120, preferably an integer from 1 to 60.

In a specific embodiment of the present invention, said PEG2 is a multi-branched polyethylene glycol residue having a structure of general formula (IV):

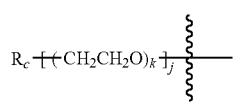
(IV)

wherein, k is an integer from 1 to 80, preferably an integer from 1 to 40;

j is an integer from 3 to 8;

$R_c$ is a core molecule of the multi-branched polyethylene glycol, and $R_c$ is selected from the group consisting of residues of pentaerythritol, oligo-pentaerythritol, methyl glucoside, sucrose, diglycol, propanediol, glycerol, and polyglycerol, and preferably, $R_c$ is selected from the group consisting of residues of pentaerythritol, dipentaerythritol and tripentaerythritol.

The present invention also provides a pharmaceutically acceptable salt of the ligand drug conjugate of the present invention. The pharmaceutically acceptable salt includes an organic salt or an inorganic salt, including, but are not limited to, a sodium salt, a potassium salt, a cesium salt, a calcium salt, a magnesium salt, a triethylamine salt, a pyridine salt, a methylpyridine salt, an ethanolamine salt, a triethanolamine salt, a dicyclohexylamine salt, a N,N-dibenzylethylenediamine salt, hydrochloride, hydrobromide, sulfate, nitrate, phosphate, formate, acetate, trifluoroacetate, pantothenate, succinate, citrate, tartrate, fumarate, maleate, gluconate, glucuronate, saccharate, benzoate, lactate, mesylate, esilate, besylate, tosilate, aspartate, glutamate, ascorbate, and a combination of the above salts.

The present invention further provides a pharmaceutical composition comprising the ligand drug conjugate of the present invention and a pharmaceutically acceptable carrier or excipient.

In an embodiment of the present invention, the pharmaceutically acceptable composition may comprise from about 1 to about 99% by weight of the conjugate of the present invention, and from 99 to 1% by weight of a suitable pharmaceutically acceptable carrier or excipient, depending on the mode of administration desired. Preferably, the composition comprises from about 5 to 75% by weight of the conjugate of the present invention, the balance being a suitable pharmaceutically acceptable carrier or excipient. More preferably, the composition comprises from about 10 to 50% by weight of the conjugate of the present invention, the balance being a suitable pharmaceutically acceptable carrier or excipient.

In an embodiment of the present invention, the pharmaceutical composition of the present invention may further comprise a small amount of auxiliary substances such as a wetting or emulsifying agent, a pH buffering agent, an antioxidant, etc., for example, citric acid, sorbitan monolaurate, triethanolamine oleate, butylated hydroxytoluene or the like.

In an embodiment of the present invention, the pharmaceutical composition is in the form of a tablet, a capsule, a pill, a granule, a powder, a suppository, an injection, a solution, a suspension, a patch, a lotion, a drop, a liniment, a spray, or the like.

In an embodiment of the present invention, the conjugate of the present invention may be administered in the form of a pure compound or a suitable pharmaceutical composition, and can be carried out by any acceptable mode of administration or reagents for similar uses. Thus, the mode of administration employed may be selected by oral, intranasal, parenteral, topical, transdermal or rectal administration in the form of a solid, semi-solid or liquid pharmaceutical form, for example, tablets, suppositories, pills, soft and hard gelatin capsules, powders, solutions, suspensions and injections, etc. A unit dosage form suitable for simple administration of a precise dosage is preferred.

The pharmaceutical composition which can be administered in a liquid form may be, for example, a solution or suspension formed by dissolving and dispersing the conjugate of the present invention (about 0.5 to about 20%) and the optionally present pharmaceutically acceptable adjuvant in a carrier by means of dissolution, dispersion, or the like. Examples of the carrier may be water, saline, aqueous glucose, glycerol, ethanol, etc.

In another aspect, the present invention provides use of the ligand drug conjugate of the present invention or a salt and a pharmaceutical composition thereof for the prophylaxis and/or treatment of a disease.

In an embodiment of the present invention, the disease is cancer, pathogenic organism infection or autoimmune disease.

Wherein, the cancer is hematopoietic tumor, carcinoma, sarcoma, melanoma or neuroglioma.

Wherein, the pathogenic organism is selected from the group consisting of: human immunodeficiency virus (HIV), *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis, Pneumococcus, Hemophilus influenzae* type b, *Treponema pallidum, Borrelia burgdorferi*, West Nile virus, *Bacillus pyocyaneus, Mycobacterium leprae, Alcaligenes abortus*, Rabies virus, Influenza virus, cytomegalovirus, Herpes simplex virus type I, Herpes simplex virus type II, human serum parvo-like virus, Respiratory syncytial virus, varicella-zoster virus, Hepatitis B virus, Measles virus, Adenovirus, human T cell leukemia virus, Epstein-Barr virus, Murine leukemia virus, mumps virus, Vesicular stomatitis virus, Sindbis virus, Lymphocytic choriomeningitis virus, Wart virus, Bluetongue virus, Sendai virus, Feline leukemia virus, reovirus, poliovirus, simian virus 40, mouse mammary tumor virus, Dengue virus, Rubella virus, *Plasmodium falciparum, Plasmodium vivax, Toxoplasma gondii*, and *Trypanosoma cruzi*.

Wherein, the autoimmune disease is selected from the group consisting of immune-mediated thrombocytopenia, dermatomyositis, Sjogren's syndrome, multiple sclerosis, Sydenham's Chorea, myasthenia gravis, systemic lupus erythematosus, lupus nephritis, rheumatic fever, rheumatoid arthritis, polyglandular syndrome, bullous pemphigoid, diabetes, henoch-schonlein purpura, post-streptococcal infection nephritis, erythema nodosum, Takayasu's arteritis, Addison's disease, sarcoidosis, ulcerative colitis, erythema multiforme, IgA nephropathy, polyarteritis nodosa, ankylosing spondylitis, Goodpasture syndrome, thromboangitis obliterans, primary biliary cirrhosis, hashimoto thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, locomotor ataxia, giant cell arteritis/polymyalgia, pernicious anemia, acute glomerulonephritis, fibrosing alveolitis and juvenile diabetes.

The present invention also provides a method of treating a disease, the method comprising administering to a subject the ligand drug conjugate of the present invention, or a pharmaceutically acceptable salt or pharmaceutical composition thereof.

In a specific embodiment of the present invention, the ligand drug conjugate or a pharmaceutically acceptable salt or pharmaceutical composition thereof is administered in combination with one or more of the following therapeutic methods: an unconjugated antibody, a radiolabeled antibody, a drug-conjugated antibody, a toxin-conjugated antibody, a gene therapy, a chemotherapy, a therapeutic peptide, an oligonucleotide, a local radiotherapy, a surgery, and an interfering RNA therapy.

In an embodiment of the present invention, the disease is cancer, a pathogenic organism infection or an autoimmune disease.

Wherein, the cancer is hematopoietic tumor, carcinoma, sarcoma, melanoma or neuroglioma.

Wherein, the pathogenic organism is selected from the group consisting of human immunodeficiency virus (HIV), *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis, Pneumococcus, Hemophilus influenzae* type b, *Treponema pallidum, Borrelia burgdorferi*, West Nile virus, *Bacillus pyocyaneus, Mycobacterium leprae, Alcaligenes abortus*, Rabies virus, Influenza virus, cytomegalovirus, Herpes simplex virus type I, Herpes simplex virus type II, human serum parvo-like virus, Respiratory syncytial virus, varicella-zoster virus, Hepatitis B virus, Measles virus, Adenovirus, human T cell leukemia virus, Epstein-Barr virus, Murine leukemia virus, mumps virus, Vesicular stomatitis virus, Sindbis virus, Lymphocytic choriomeningitis virus, Wart virus, Bluetongue virus, Sendai virus, Feline leukemia virus, reovirus, poliovirus, simian virus 40, mouse mammary tumor virus, Dengue virus, Rubella virus, *Plasmodium falciparum, Plasmodium vivax, Toxoplasma gondii*, and *Trypanosoma cruzi*.

Wherein, the autoimmune disease is selected from the group consisting of immune-mediated thrombocytopenia, dermatomyositis, Sjogren's syndrome, multiple sclerosis, Sydenham's Chorea, myasthenia gravis, systemic lupus erythematosus, lupus nephritis, rheumatic fever, rheumatoid arthritis, polyglandular syndrome, bullous pemphigoid, diabetes, henoch-schonlein purpura, post-streptococcal infection nephritis, erythema nodosum, Takayasu's arteritis, Addison's disease, sarcoidosis, ulcerative colitis, erythema multiforme, IgA nephropathy, polyarteritis nodosa, ankylosing spondylitis, Goodpasture syndrome, thromboangitis obliterans, primary biliary cirrhosis, hashimoto thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, locomotor ataxia, giant cell arteritis/polymyalgia, pernicious anemia, acute glomerulonephritis, fibrosing alveolitis and juvenile diabetes.

In still another aspect, the present invention provides a preparation method of a ligand drug conjugate, and the synthetic route of the preparation method is as follows:
(1) PEG1+modifying group=[PEG-1],
(2) [PEG-1]+ligand unit=ligand unit-[PEG-1] (Compound A),
(3) PEG2+modifying group=[PEG-2],
(4) Drug+[PEG-2]=[PEG-2]-drug (Compound B),
(5) Compound A+Compound B=ligand drug conjugate;
or,
(1) PEG1+modifying group=[PEG-1],
(2) PEG2+modifying group=[PEG-2],
(3) Drug+[PEG-2]=[PEG-2]-drug (Compound B),
(4) [PEG-1]+Compound B=[PEG-1]-[PEG-2]-drug (Compound C),
(5) Ligand unit+compound C=ligand drug conjugate;
or,
(1) PEG1+modifying group=[PEG-1],
(2) PEG2+modifying group=[PEG-2],
(3) [PEG-1]+[PEG-2]=[PEG-1]-[PEG-2] (Compound D),
(4) Compound D+drug=[PEG-1]-[PEG-2]-drug (Compound C),
(5) Ligand unit+Compound C=ligand drug conjugate.

In an embodiment of the present invention, said [PEG-1] is a double- or multi-terminally modified polyethylene glycol residue, at least one end of which comprises a reactive end group Z1 for linking with the ligand unit, and at least one end of which comprises a reactive end group Z2 for linking with PEG2;

the reactive end group Z1 is selected from the group consisting of succinimido, sulfydryl, carboxyl, propionic acid group (2-carboxyethyl), aldehyde group, acryloxy, glutaric acid group (4-carboxybutyryloxy), maleimido, N-hydroxy-succinimido, N-hydroxy-glutarimide, succinimide carbonate group, succinimide acetate group, succinimide propionate group, succinimide succinate group, imino acid ester group, p-nitrophenyl carbonate group, cyanuric chloride group, o-dithiopyridinyl, thioester group, hydrazide group, isocyanato, isothiocyano, and vinyl sulfone group;

the reactive end group Z2 is selected from the group consisting of ethynyl, azido, sulfydryl and sulfydryl-reactive group, and the sulfydryl-reactive group is capable of reacting with sulfydryl to form a thioether bond or a disulfide bond, including, but not limited to, maleimido, glutaric acid group, vinyl sulfone group, haloacetamido, dithiopyridinyl, thiosulfonate group, ethyleneimine group, aziridinyl group, and aminosulfonyl group;

said [PEG-2] is a double- or multi-terminally modified polyethylene glycol residue, at least one end of which comprises a reactive end group Z3 that can react with the reactive end group Z2, and at least one end of which comprises a reactive end group Z4;

the reactive end group Z3 is selected from the group consisting of ethynyl, azido, sulfydryl and sulfydryl-reactive group, and the sulfydryl-reactive group is capable of reacting with sulfydryl to form a thioether bond or a disulfide bond, including, but not limited to, maleimido, glutaric acid group, vinyl sulfone group, haloacetamido, dithiopyridinyl, thiosulfonate group, ethyleneimine group, aziridinyl group, and aminosulfonyl group; and the reactive end group Z4 is carboxyl, hydroxyl or carbonyl.

In an embodiment of the present invention, between the reactive end groups, Z1 and Z2, Z3, Z4, and polyethylene glycol residues, a linking group may be further included according to actual needs, and the linking group includes, but is not limited to, $-(CH_2)_i-$, $-(CH_2)_iNH-$, $-(CH_2)_iOCOO-$, $-(CH_2)_iOCONH-$, $-(CH_2)_iNHCONH-$, $-(CH_2)_iNHCO-$, $-OC(CH_2)_iCOO-$, $-(CH_2)_iCOO-$ and $-(CH_2)_iCONH-$, i is an integer from 0 to 10; and preferably, i is 0, 1 or 2.

Compared with the prior art, the present invention has the following beneficial effects:

In the ligand drug conjugate of the present invention, a PEG linker is used for coupling a drug and a ligand unit, wherein, in a preferred embodiment of the present invention, a plurality of drug molecules may be linked by using a branched PEG or a multi-arm PEG, which increases the drug loading capacity; and at the same time, due to the hydrophilicity of PEG, while ensuring a high drug loading capacity, it is also ensured that the pharmacokinetic characteristics of the ligand drug conjugate are close to those of antibody-conjugated drugs with a low drug loading capacity.

The ligand drug conjugate of the present invention has the characteristics of high loading capacity, high pharmaceutical efficacy, low toxicity and low risk. In a preferred embodiment, it can be especially used for linking a drug molecule with a low toxicity, thereby expanding the therapeutic window.

Further, the PEG linker provided by the present invention is obtained by adopting a stepwise linkage of two or more PEG molecules, has high purity and simple preparation, and overcomes the defects that the traditional multi-arm PEG (especially the PEG having 8 or more arms) has low purity and difficulty in application. In addition, the linking sites in the PEG linker of the present invention are uniformly distributed, which causes the drug uniformly distributed, thereby avoiding the problem of reduced pharmaceutical efficacy caused by hydrophobic aggregation brought by local dense distribution of drugs (mostly hydrophobic).

Figure 1:
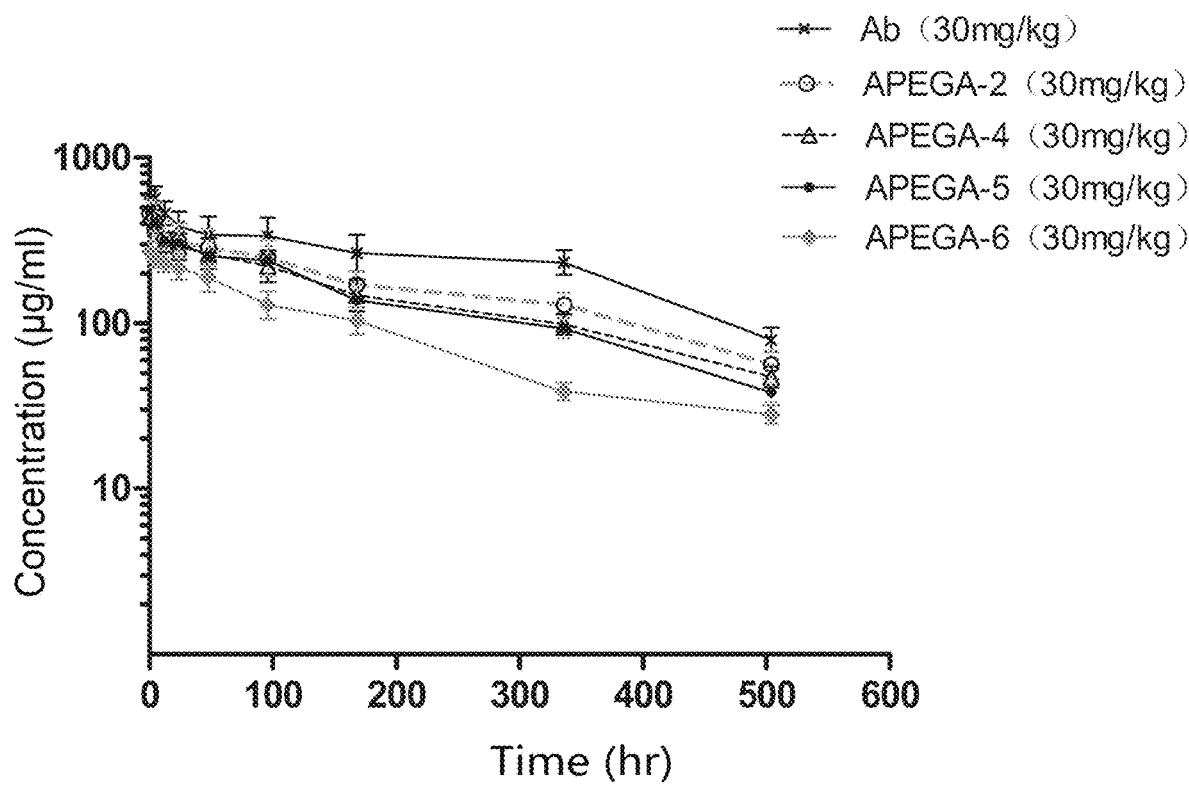
FIG. 1 is a rat pharmacokinetic graph (total antibody concentration, μg/mL Vs time, days), Ab: unmodified antibody; APEGA-2: antibody-drug conjugate (four-arm+single-arm); APEGA-4: antibody-drug conjugate (four-arm+four-arm); APEGA-5: antibody-drug conjugate (four-arm+eight-arm); and APEGA-6: antibody-drug conjugate (eight-arm+four-arm).

antibody-drug conjugate (four-arm+eight-arm); and APEGA-6: antibody-drug conjugate (eight-arm+four-arm).

DETAILED DESCRIPTION OF THE INVENTION

Unless otherwise stated, the following terms appearing herein have the following meanings.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al. (2003) Jour. of Immunology, 170: 4854-4861). Antibodies may be murine, human, humanized, chimeric antibodies or derived from other species. An antibody is a protein generated by an immune system capable of recognizing and binding to a specific antigen (Janeway, C. et al. (2001) ImmunoBiology, 5th Ed., Garland Publishing, New York). A target antigen generally has a large number of binding sites, also referred to as epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but are not limited to, cancer cell or cells that produce autoimmune antibodies associated with an autoimmune diseases. In particular, the antibody of the present invention is reactive against an antigen or epitopes thereof associated with a cancer cell, malignant cell, infectious organism or autoimmune disease. The immunoglobulin disclosed herein can be any type (e.g., IgG, IgE, IgM, IgD, and IgA), class (e.g., IgG1, IgG2, IgG3, IgG4, IgA, and IgA2) or subclass of immunoglobulin molecule. The immunoglobulins can be derived from any species. However, in one aspect, the immunoglobulin is of human, murine, or rabbit origin.

The term "antibody fragment" as used herein encompasses a portion of a full-length antibody, generally the antigen binding or variable region thereof. Examples of antibody fragments include: Fab, Fab', F(ab')2 and Fv fragments; diabodies; linear antibodies; minibodies (Olafsen et al. (2004) Protein Eng. Design & Sel. 17(4): 315-323); fragments produced by a Fab expression library; anti-idiotype (anti-Id) antibodies; CDR (complementarity determining region); and epitope-binding fragments of any of the above which immunospecifically bind to cancer cell antigens, viral antigens or microbial antigens; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Moreover, in contrast to polyclonal antibody preparations which typically include different antibodies directed against different determinants (epitopes), each monoclonal antibody is directed against a single determinant on the antigen. In addition to their specificity, the monoclonal antibodies have the advantage that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be prepared by the hybridoma method first described by Kohler et al. (Kohler et al. (1975) Nature 256: 495) or may be prepared by recombinant DNA methods (see for example: U.S. Pat. Nos. 4,816,567; 5,807,715). For example, the monoclonal antibodies may also be isolated from phage antibody libraries using the techniques described in Clackson et al. (Clackson et al. (1991) Nature, 352: 626-628) and Marks et al. (Marks et al. (1991) J. Mol. Biol., 222: 581-597).

The "monoclonal antibodies" herein specifically include "chimeric" antibodies in which a portion of the heavy chain and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired biological activity (U.S. Pat. No. 4,816,567; and Morrison et al. (1984) Proc. Natl. Acad. Sci. USA, 81:6851-6855). Chimeric antibodies of interest herein include "primatized" antibodies comprising variable region antigen-binding sequences derived from a non-human primate and human constant region sequences.

The term "intact antibody" as used herein is one comprising a VL and VH domains as well as a light chain constant domain (CL) and heavy chain constant domains, CH1, CH2 and CH3. The constant domains may be native sequence constant domains (e.g., human native sequence constant domains) or an amino acid sequence variant thereof. The intact antibody may have one or more "effector functions" which refer to those biological activities attributable to the Fc constant region (a native sequence Fc region or amino acid sequence variant Fc region) of an antibody. Examples of effector functions of antibody include C1q binding; complement dependent cytotoxicity; Fc receptor binding; antibody-dependent cell-mediated cytotoxicity (ADCC); phagocytosis; and down regulation of cell surface receptors such as B cell receptors and BCR.

Depending on the amino acid sequence of the constant domain of their heavy chains, intact antibodies can be assigned to different "classes". There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA1 and IgA2. The heavy chain constant domains that correspond to different classes of antibodies are referred to as α, δ, cε, γ, and μ, respectively. The subunit structures and three-dimensional configurations of different classes of immunoglobulins are well known. Ig forms include hinge-modifications or hingeless forms (Roux et al. (1998) J. Immunol. 161: 4083-4090; Lund et al. (2000) Eur. J. Biochem. 267: 7246-7256; US 2005/0048572; US 2004/0229310).

The term "parent antibody" herein is an antibody comprising an amino acid sequence from which one or more amino acid residues are replaced by one or more cysteine residues. The parent antibody may comprise a native or wild type sequence. The patent antibody may have pre-existing amino acid sequence modifications (such as additions, deletions and/or substitutions) relative to other native, wild type, or modified forms of an antibody. A parent antibody may be directed against a target antigen of interest, e.g., a biologically important polypeptide. Antibodies directed against non-polypeptide antigens, such as tumor-associated glycolipid antigens; see U.S. Pat. No. 5,091,178, are also contemplated. Exemplary parent antibodies include antibodies having affinity and selectivity for cell surface and transmembrane receptors and tumor-associated antigens (TAA).

The term "antigen that binds to an antibody" as used herein includes, but is not limited to, HER-2/neu, carbonic anhydrase IX, B7, CCCL19, CCCL21, CSAp, BrE3, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM-6, alpha fetoprotein (AFP), VEGF, ED-B fibronectin, EGP-1, EGP-2, EGF receptor (ErbB1), ErbB2, ErbB3, factor H, FHL-1, Flt-3, folate receptor, Ga 733, GROB, HMGB-1, hypoxia inducible factor (HIF), HM1.24, insulin-like growth factor (ILGF), IFN-γ, IFN-α, IFN-β, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, ganglioside, HCG, HLA-DR, CD66a-d, MAGE, mCRP, MCP-1, MIP-1A, MIP-1B, macrophage migration inhibitory factor (MIF), MUC1, MUC2, MUC3, MUC4, MUC5, placental growth factor (PIGF), PSA, PSMA, PSMA antigen, PAM4 antigen, NCA-95, NCA-90, A3, A33, Ep-CAM, KS-1, Le(y), mesothelin, S100, tenascin, TAC, Tn antigen, Thomas-Friedenreich antigen, tumor necrosis antigen, tumor angiogenic antigen, TNF-α, TRAIL receptor (R1 and R2), VEGFR, RANTES, T101, cancer stem cell antigen, complement factors C3, C3a, C3b, C5a, and C5, and oncogene products, etc.

EXAMPLE

The various embodiments of the present invention are illustrated by the following examples, but are not intended to limit the present invention.

The irinotecan used in the examples was purchased from Shanghai Longxiang Biomedical Development Co., Ltd., 4-dimethylaminopyridine (DMAP) and 1-hydroxybenzotriazole (HOBT) were purchased from Shanghai MEDPEP Co., Ltd., other reagents were purchased from Sinopharm Chemical Reagent Co., Ltd., and polyethylene glycol derivatives were provided by JenKem Technology Co., Ltd. (Beijing).

Synthesis Examples of [PEG-1]

Example 1: Synthesis of Four-Arm Polyethylene Glycol Hydroxy-Monoacetic Acid (III-1)

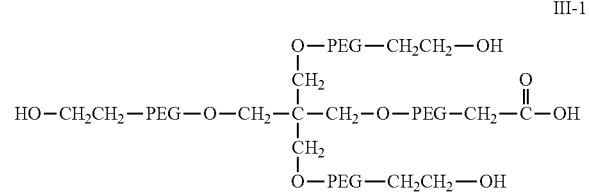

III-1

Steps:

In a three-neck round-bottom flask, nitrogen gas was introduced, and 100 g of four-arm polyethylene glycol (4ARM-PEG-5K) and 800 mL of tetrahydrofuran (THF) were added. The resulting mixture was heated for dissolution, and about 20% solvent was distilled off. The resulting mixture was cooled and added with 4.48 g of potassium t-butoxide. The resulting mixture was reacted at room temperature for 2 hours, then added dropwise with 5.17 mL of t-butyl bromoacetate, and reacted overnight at room temperature. On the next day, the reaction mixture was filtered. The filtrate was concentrated to a viscous state, added with 500 mL of an alkaline hydrolysis solution (8.16 g of sodium hydroxide and 77.52 g of sodium phosphate in 500 mL of water), and alkalized at 80° C. for 2 hours. The resulting solution was adjusted to pH 2-3 with 2 N hydrochloric acid solution, added with 15% sodium chloride, and extracted three times with dichloromethane. The organic phases were combined, dried over anhydrous sodium sulfate, and filtered. The filtrate was concentrated at 50° C. to a viscous state and added with diethyl ether for precipitation. The obtained precipitate was dried under vacuum. 22 g of the crude product was prepared into an aqueous solution having a conductivity of 100 μs/cm, which was separated by a DEAE anion column. The sodium chloride aqueous solution eluate having a conductivity of 50 μs/cm was collected. The aqueous phase was adjusted to pH 2-3 with 2 N aqueous hydrochloric acid and extracted with dichloromethane. The organic phases were combined, dried over anhydrous sodium sulfate, and filtered. The filtrate was concentrated and precipitated with diethyl ether to give four-arm polyethylene glycol hydroxy-monoacetic acid (III-1).

NMR (DMSO) δ:

Four-arm polyethylene glycol hydroxy-monoacetic acid (III-1): 4.01 (s, 2H, CH$_2$COOH), 4.54 (t, 3H, CH$_2$OH).

Example 2: Four-Arm Polyethylene Glycol Hydroxy-Methyl Monoacetate (IVA-1)

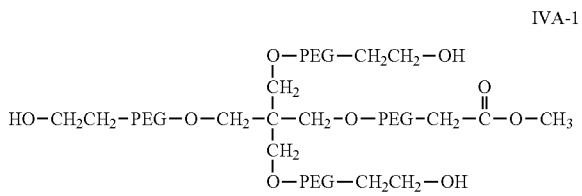

IVA-1

Steps:

In a single-neck round-bottom flask, 3.2 g of four-arm polyethylene glycol hydroxy-monoacetic acid (III-1) was added and dissolved in 16 mL of anhydrous methanol. The resulting mixture was ice-bathed, added dropwise with 0.64 mL of concentrated sulfuric acid, and then reacted for 3 hours at room temperature. The reaction system was adjusted to pH 7.0 with 8% aqueous sodium hydrogencarbonate and extracted three times with dichloromethane. The organic phases were combined, dried over anhydrous magnesium, and filtered. The filtrate was concentrated at 40° C. to a viscous state and precipitated with diethyl ether. The obtained precipitate was vacuum dried to give four-arm polyethylene glycol hydroxy-methyl monoacetate (IVA-1).

NMR (DMSO) δ: 3.32 (s, 3H, CH$_2$COOCH$_3$), 4.13 (s, 2H, CH$_2$COOCH$_3$), 4.57 (t, 3H, CH$_2$OH).

Example 3: Four-Arm Polyethylene Glycol Sulfonate-Methyl Monoacetate (IVB-1)

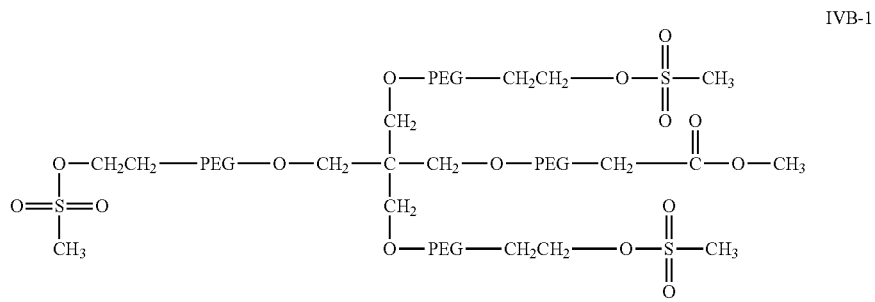

IVB-1

Steps:

In a three-neck round-bottom flask, nitrogen gas was introduced, and 3.0 g of four-arm polyethylene glycol hydroxy-methyl monoacetate was added and dissolved in 50 mL of toluene. The resulting mixture was heated, and 38 mL of toluene was distilled off. When the distillate was clear, the mixture was cooled to room temperature, added with 5 mL of dichloromethane, and stirred for 10 minutes, added with 188 µL of triethylamine, and stirred for 5 minutes, and added with 94 µL of methylsulfonyl chloride dropwise. The resulting mixture was reacted overnight under closed conditions. On the next day, the reaction mixture was added with 720 µL of absolute ethanol, stirred for 15 minutes, filtered, concentrated at 60° C. to a viscous state, and then dissolved in 60 mL of isopropanol under heating, then precipitated in an ice water bath, and filtered. The obtained filter cake was washed once with isopropanol and dried under vacuum to give four-arm polyethylene glycol sulfonate-methyl monoacetate (IVB-1).

NMR (DMSO) δ: 3.17 (s, 9H, $CH_2OSO_2CH_3$), 4.13 (s, 2H, $CH_2COOCH_3$), 4.30 (t, 6H, $CH_2OSO_2CH_3$).

Example 4: Four-Arm Polyethylene Glycol Azide-Methyl Monoacetate (IVB-2)

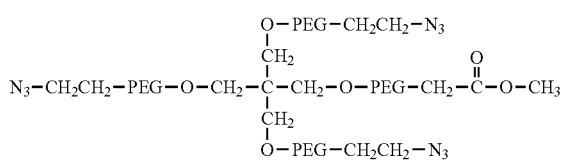

IVB-2

Steps:

In a three-neck round-bottom flask, nitrogen gas was added, and 5.0 g of four-arm polyethylene glycol sulfonate-methyl monoacetate and 0.351 g of sodium azide were added and dissolved in 25 mL of DMF. The resulting mixture was heated to 90° C., reacted for 3 hours, and then cooled to room temperature. The reaction mixture was added with 25 mL of water and 15% sodium chloride and extracted with dichloromethane. The organic phase was dried over anhydrous sodium sulfate and filtered. The filtrate was concentrated, dissolved in 100 mL of isopropanol under heating, then precipitated in an ice water bath, and filtered. The obtained filter cake was washed once with isopropanol and dried under vacuum to give four-arm polyethylene glycol azide-methyl monoacetate (IVB-2).

NMR (DMSO) δ: 4.13 (s, 2H, $CH_2COOCH_3$).

Example 5: Four-Arm Polyethylene Glycol Azide-Monoacetic Acid (IVB-3)

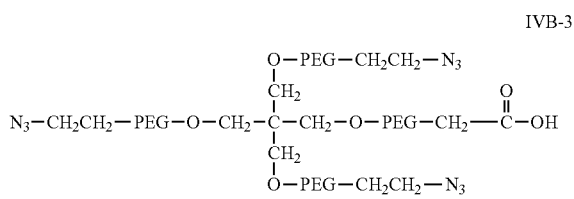

IVB-3

Steps:

To a 100 mL beaker, 4.5 g of four-arm polyethylene glycol azide-methyl monoacetate was added, and de-aerated water was added. The system was adjusted to pH 12 with 0.2 N sodium hydroxide, reacted under stirring at room temperature for 3 hours, then adjusted to pH 2-3 with 1 N hydrochloric acid, added with 15% sodium chloride, and extracted with dichloromethane. The organic phase was dried over anhydrous sodium sulfate and filtered. The filtrate was concentrated, dissolved in 90 mL of isopropanol under heating, then precipitated in an ice water bath, and filtered. The obtained filter cake was washed once with isopropanol and dried under vacuum to give four-arm polyethylene glycol azide-monoacetic acid (IVB-3).

NMR (DMSO) δ: 4.01 (s, 2H, $CH_2COOH$).

Example 6: Four-Arm Polyethylene Glycol Azide-Monoacetate Succinimide Ester (IVB-4)

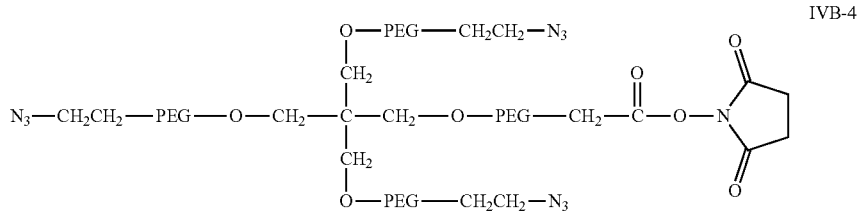

Steps:
To a 100 mL beaker, 2.0 g of four-arm polyethylene glycol azide-monoacetic acid and 56 mg of N,N-hydroxysuccinimide (NETS) were added and dissolved in 20 mL of dichloromethane, and 165 mg of dicyclohexylcarbodiimide (DCC) was added. The resulting mixture was reacted under stirring at room temperature for 2 hours and then filtered. The filtrate was concentrated, dissolved in 40 mL of isopropanol under heating, precipitated in an ice water bath, and filtered. The obtained filter cake was washed once with isopropanol and dried under vacuum to give four-arm polyethylene glycol azide-monoacetate succinimidyl ester (IVB-4).

NMR (DMSO) δ: 2.83 (s, 4H,

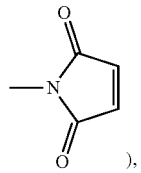

), 4.60 (s, 2H, CH$_2$COO).

Example 7: Synthesis of Four-Arm Polyglycol Amine-Monoacetic Acid (V-1)

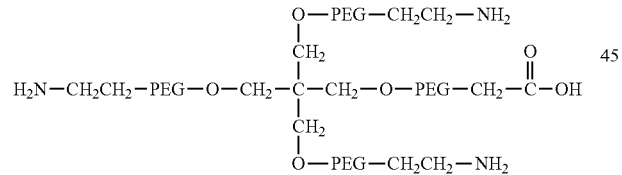

Steps:
In a three-neck round-bottom flask, 5 g of four-arm polyethylene glycol sulfonate-methyl monoacetate was dissolved in 7.8 mL of de-aerated water under nitrogen protection. The solution was adjusted to pH 12.0 with 2 N aqueous sodium hydroxide solution and reacted at room temperature for 2 to 2.5 hours. The system was added with 26 mL of an aqueous ammonia solution in which 1.3 g of ammonium chloride was dissolved, and reacted under stirring at room temperature for 72 hours. After the reaction was completed, the reaction mixture was added with 7 g of sodium chloride, and after dissolving, the reaction mixture was extracted three times with dichloromethane. The organic phases were combined, concentrated at 40° C. to dryness, then added with 30 mL of degassed water, stirred for dissolution until the solution was clear. The solution was adjusted to pH 2-3 with 2 N hydrochloric acid, added with 5 g of sodium chloride, and then extracted three times with dichloromethane. The organic phases were combined, dried over anhydrous sodium sulfate until the liquid was clarified, and filtered. The filtrate was concentrated at 40° C. to a viscous state, precipitated with 50 mL of diethyl ether, and then filtered. The obtained precipitate was dried under vacuum to give four-arm polyethylene glycol amine-monoacetic acid (V-1).

NMR (DMSO) δ: 2.96 (t, 6H, CH$_2$CH$_2$NH$_2$), 4.40 (s, 2H, CH$_2$COOH).

Example 8: Synthesis of Four-Arm Polyethylene Glycol Maleimide-Monoacetic Acid (V-2)

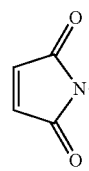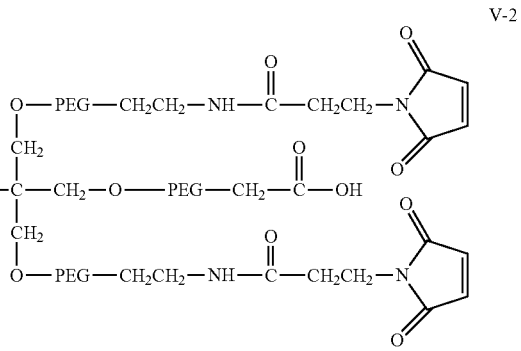

Steps:

In a single-neck round-bottom flask, 2.6 g of four-arm polyethylene glycol amine-monoacetic acid was added, dissolved in dichloromethane, and bathed in ice water, and 500 μL of TEA and 1.06 g of MAL-NHS were added. The resulting mixture was reacted under stirring at room temperature for 12 hours or more. The reaction mixture was concentrated at 40° C. to dryness, added with 30 mL of de-aerated water, stirred, and then washed with 20 mL of ethyl acetate. The aqueous phase was extracted three times with dichloromethane. The organic phases were combined, dried over anhydrous sodium sulfate until the liquid was clarified, and filtered. The filtrate was concentrated at 40° C. to a viscous state, precipitated with 50 mL of isopropanol in an ice water bath, and then filtered. The obtained precipitate was dried under vacuum to give four-arm polyethylene glycol maleimide-monoacetic acid (V-2).

NMR (DMSO) δ: 2.32 (t, 6H,

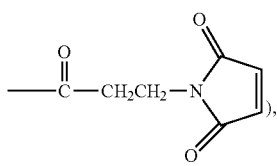

3.13 (q, 6H, CH$_2$CH$_2$NH), 4.40 (s, 2H, CH$_2$COOH), 6.99 (s, 6H,

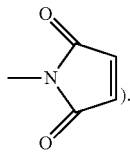

Example 9: Four-Arm Polyethylene Glycol Maleimide-Monoacetate Succinimidyl Ester (V-3)

Steps:

To a 100 mL beaker, 2.0 g of four-arm polyethylene glycol maleimide-monoacetic acid and 53 mg of NHS were added and dissolved in 20 mL of dichloromethane, and 120 mg of DCC was added. The resulting mixture was reacted under stirring at room temperature for 2 hours, and then filtered. The filtrate was concentrated, dissolved in 40 mL of isopropanol under heating, then precipitated in an ice water bath, and then filtered. The obtained filter cake was washed once with isopropanol and dried under vacuum to give four-arm polyethylene glycol maleimide-monoacetate succinimidyl ester (V-3).

NMR (DMSO) δ: 2.32 (t, 6H,

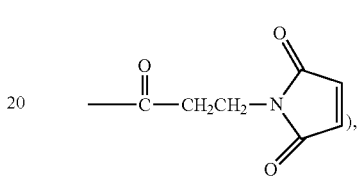

2.82 (s, 4H,

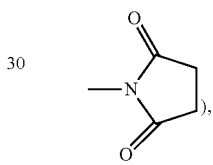

3.15 (q, 6H, CH$_2$CH$_2$NH), 4.60 (s, 2H, CH$_2$COO), 6.99 (s, 6H,

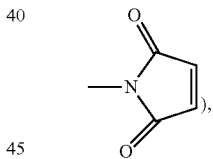

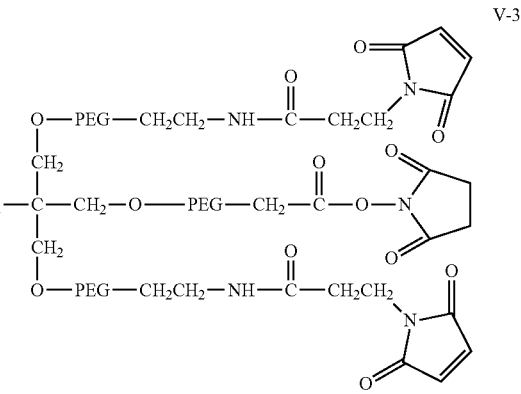

(MAL)$_3$-4ARM-PEG(5K)-NHS

Example 10: Synthesis of Eight-Arm Polyethylene Glycol Hydroxy-Monoacetic Acid (III-2)

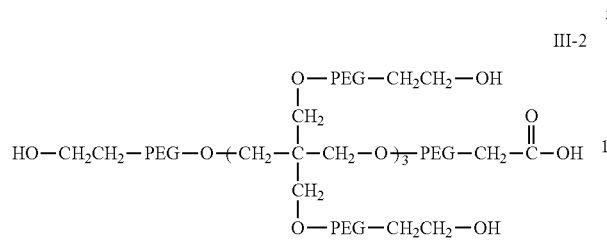

Steps:

In a three-neck round-bottom flask, nitrogen gas was added, and 100 g of 8ARM-PEG-5000 and 800 ml of THF were added and dissolved by heating, and about 20% solvent was distilled off. The resulting mixture was cooled, added with 17.92 g of potassium t-butoxide, and reacted at room temperature for 2 hours. The resulting mixture was added dropwise with 20.68 ml of t-butyl bromoacetate, and reacted overnight at room temperature. On the next day, the reaction mixture was filtered. The filtrate was concentrated to a viscous state, added with 1000 ml of an alkaline hydrolysis solution (16.32 g of sodium hydroxide and 155.04 g of sodium phosphate in 1000 ml of water), and alkalized at 80° C. for 2 hours. The solution was adjusted to pH 2-3 with 2 N hydrochloric acid solution, added with 15% sodium chloride, and extracted three times with dichloromethane. The organic phases were combined, dried over anhydrous sodium sulfate, and filtered. The filtrate was concentrated at 50° C. to a viscous state, and precipitated with diethyl ether. The obtained precipitate was dried under vacuum. 40 g of the crude product was prepared into an aqueous solution having a conductivity of 100 μs/cm, which was separated by a DEAE anion column. Sodium chloride aqueous solution eluate having a conductivity of 50 μs/cm was collected. The aqueous phase was adjusted to pH 2-3 with 2 N hydrochloric acid and extracted with dichloromethane. The organic phases were combined, dried over anhydrous sodium sulfate, and filtered. The filtrate was concentrated to dryness to give eight-arm polyethylene glycol hydroxy-monoacetic acid (III-2).

Eight-arm polyethylene glycol hydroxy-monoacetic acid (III-2): 4.01 (s, 2H, CH$_2$COOH), 4.54 (t, 7H, CH$_2$OH).

Example 11: Eight-Arm Polyethylene Glycol Hydroxy-Methyl Monoacetate (IIIB-2)

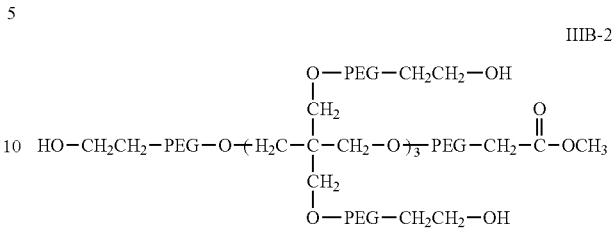

Steps:

In a single-neck round-bottom flask, 4.0 g of eight-arm polyethylene glycol hydroxy-monoacetic acid (III-2) was added and dissolved in 20 ml of anhydrous methanol and bathed in ice water, and 0.8 ml of concentrated sulfuric acid was added dropwise. The resulting mixture was reacted at room temperature for 3 hours. The system was adjusted to pH 7.0 with 8% sodium bicarbonate aqueous solution and extracted three times with dichloromethane. The organic phases were combined, dried over anhydrous magnesium sulfate, and filtered. The filtrate was concentrated at 40° C. to a viscous state to dryness to give eight-arm polyethylene glycol hydroxy-methyl monoacetate (IIIB-2).

NMR (DMSO) δ: 3.32 (s, 3H, CH$_2$COOCH$_3$), 4.13 (s, 2H, CH$_2$COOCH$_3$), 4.57 (t, 7H, CH$_2$OH).

Example 12: Eight-Arm Polyethylene Glycol Sulfonate-Methyl Monoacetate (IIIC-2)

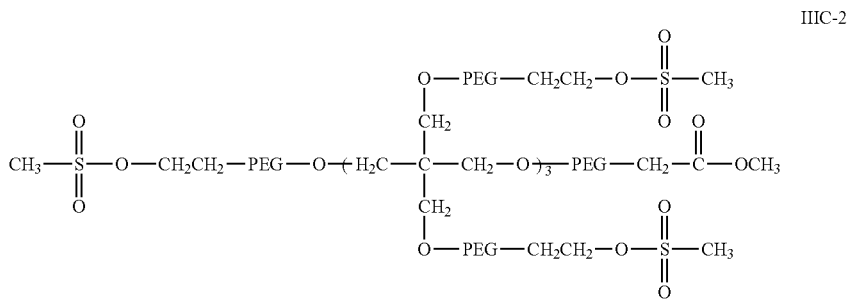

Steps:

In a three-neck round-bottom flask, nitrogen gas was added, and 3.0 g of eight-arm polyethylene glycol hydroxy-methyl monoacetate was added and dissolved in 50 ml of toluene. The resulting mixture was heated, and 38 mL of toluene was distilled off. When the distillate was clear, the mixture was cooled to room temperature, added with 5 ml of dichloromethane, and stirred for 10 minutes, added with 878 μl of triethylamine, and stirred for 5 minutes, and added dropwise with 440 μl of methylsulfonyl chloride. The resulting mixture was reacted overnight under closed conditions. On the next day, the reaction mixture was added with 3 ml of absolute ethanol, stirred for 15 minutes, and filtered. The filtrate was concentrated at 60° C. to dryness to give eight-arm polyethylene glycol sulfonate-methyl monoacetate (IIIC-2).

NMR (DMSO) δ: 3.17 (s, 21H, CH$_2$OSO$_2$CH$_3$), 4.13 (s, 2H, CH$_2$COOCH$_3$), 4.30 (t, 14H, CH$_2$OSO$_2$CH$_3$).

Example 13: Synthesis of Eight-Arm Polyethylene Glycol Amine-Monoacetic Acid (V-2)

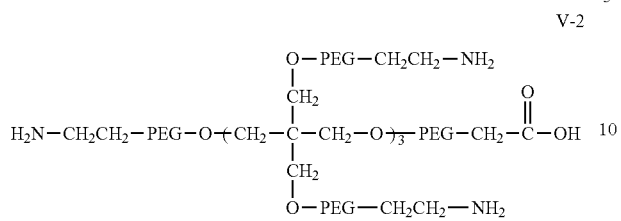

Steps:

In a single-neck round bottom flask, 2.6 g of eight-arm polyethylene glycol sulfonate-methyl monoacetate was added and dissolved in 7.8 mL of de-aerated water. The solution was adjusted to pH 12.0 with 2 N aqueous sodium hydroxide solution and reacted at room temperature for 2 to 2.5 hours. The system was added with 26 mL of an aqueous ammonia solution in which 1.3 g of ammonium chloride was dissolved, and reacted under stirring at room temperature for 72 hours. After the reaction was completed, the reaction mixture was added with 7 g of sodium chloride, and after dissolving, the reaction mixture was extracted three times with dichloromethane. The organic phases were combined, concentrated at 40° C. to dryness, then added with 30 mL of de-aerated water, stirred for dissolution until the liquid was clear. The solution was adjusted to pH 2-3 with 2 N hydrochloric acid, added with 5 g of sodium chloride, and extracted three times with dichloromethane. The organic phases were combined, dried over anhydrous sodium sulfate until the liquid was clarified, and filtered. The filtrate was concentrated at 40° C. to dryness to give eight-arm polyethylene glycol amine-monoacetic acid (V-2).

NMR (DMSO) δ: 2.96 (t, 14H, CH$_2$CH$_2$NH$_2$), 4.40 (s, 2H, CH$_2$COOH).

Example 14: Synthesis of Eight-Arm Polyethylene Glycol Maleimide-Monoacetic Acid (VI-2)

Steps:

In a three-neck round bottom flask, nitrogen gas was introduced, and 2.0 g of eight-arm polyethylene glycol hydroxy-monoacetic acid (III-2) and 0.0005 g of BHT were added and dissolved in 20 ml of dichloromethane, and 876 μl of triethylamine was added. The resulting mixture was stirred for 5 to 10 minutes, and added with 1.98 g of MAL-NHS. The system was filled with nitrogen, protected from light, and reacted under stirring overnight under closed conditions. On the next day, the reaction mixture was concentrated at 40° C. to a viscous state, added with 40 ml of de-aerated water for dissolution until the liquid was clear, allowed to stand for 30 minutes, and added with 15% sodium chloride. The system was adjusted to pH 2-3 with dilute hydrochloric acid and extracted three times with dichloromethane. The organic phases were combined, dried over anhydrous sodium sulfate until the liquid was clarified, and filtered. The filtrate was concentrated at 40° C. to dryness to give eight-arm polyethylene glycol maleimide-monoacetic acid (VI-2).

NMR (DMSO) δ: 2.32 (t, 14H,

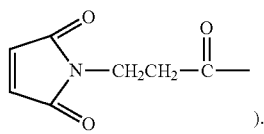

4.40 (s, 2H, CH$_2$COOH), 7.00 (s, 14H,

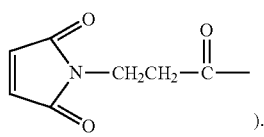

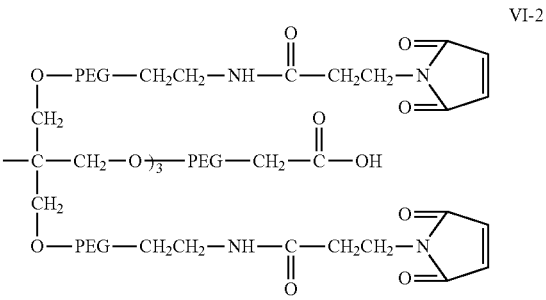

Example 15: Synthesis of Eight-Arm Polyethylene Glycol Maleimide-NHS Ester (VII-2)

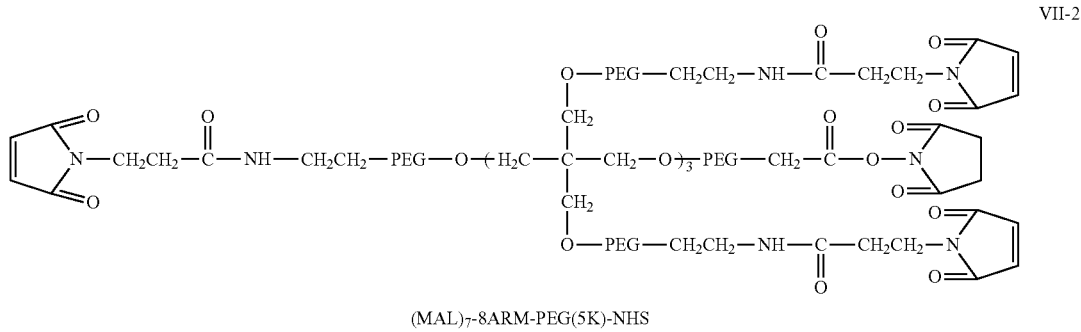

(MAL)₇-8ARM-PEG(5K)-NHS

Steps:

In a three-neck round bottom flask, nitrogen gas was introduced, and under dark conditions, 2 g of eight-arm polyethylene glycol maleimide-monoacetic acid (VI-2) and 0.12 g of NHS were added and dissolved in 40 ml of dichloromethane. After all the solids were dissolved, 0.2312 g of DCC was added. The system was reacted under stirring overnight in the dark and closed conditions. On the next day, the reaction mixture was filtered. The filtrate was concentrated at 40° C. to dryness to give eight-arm polyethylene glycol maleimide-mono-NHS ester (VII-2).

NMR (DMSO) δ: 2.32 (t, 14H,

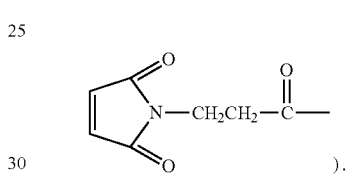
), 2.83 (s, 4H,

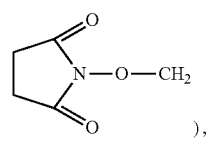
), 4.50 (s, 2H,

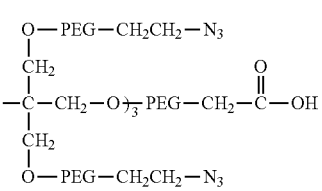
), 7.0 (s, 14H,

).

Example 16: Synthesis of Eight-Arm Polyethylene Glycol Azide-Monoacetic Acid (VI-3)

Steps:

In a three-neck round-bottom flask, nitrogen gas was introduced, and 2.0 g of eight-arm polyethylene glycol sulfonate-methyl monoacetate (IIIC-2) and 0.0005 g of BHT and 0.32 g of sodium azide were added and dissolved in 40 ml of DMF. The resulting mixture was heated to 90° C., reacted for 3 hours, cooled to room temperature, added with 40 ml of water and 15% sodium chloride, and extracted with dichloromethane. The organic phase was dried over anhydrous sodium sulfate until the liquid was clarified, and filtered. The filtrate was concentrated at 40° C. to dryness to give eight-arm polyethylene glycol azide-monoacetic acid (VI-3).

NMR (DMSO) δ: 4.00 (s, 2H, CH₂COOH).

Example 17: Synthesis of Eight-Arm Polyglycol Azide-NHS Ester (VI-4)

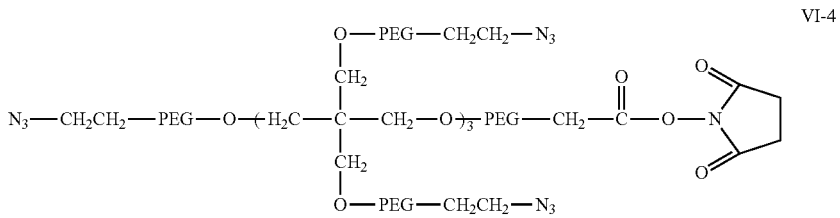

VI-4

Steps:

In a three-neck round bottom flask, nitrogen gas was introduced, and under dark conditions, 2 g of eight-arm polyethylene glycol azide-monoacetic acid (VI-3) and 0.120 g of NHS were added and dissolved in 40 ml of dichloromethane. After all the solids were dissolved, 0.2312 g of DCC was added. The system was reacted under stirring overnight in the dark and closed conditions. On the next day, the reaction mixture was filtered. The filtrate was concentrated at 40° C. to dryness to give eight-arm polyethylene glycol azide-mono-NHS ester (VI-4).

NMR (DMSO) δ: 2.83 (s, 4H,

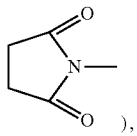

), 4.50 (s, 2H, (s, 2H,

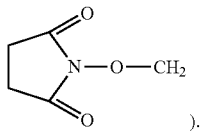

).

Example 18: Synthesis of Four-Arm Dodecaethylene Glycol Hydroxy-Monoacetic Acid Steps:

In a three-neck round-bottom flask, nitrogen gas was added, and 100 g of four-arm dodecaethylene glycol (4ARM-PEG12-OH) and 500 mL of tetrahydrofuran (THF) were added and dissolved by heating, and about 20% solvent was distilled off. The resulting mixture was cooled, added with 2.99 g of potassium t-butoxide, and reacted at room temperature for 2 hours. The resulting mixture was added dropwise with 4.34 g of t-butyl bromoacetate and reacted at room temperature overnight. On the next day, the reaction mixture was filtered. The filtrate was concentrated to a viscous state, added with 500 mL of an alkaline hydrolysis solution (4.08 g of sodium hydroxide and 38.32 g of sodium phosphate in 500 mL of water), and alkalized at 80° C. for 2 hours. The solution was adjusted to pH 2-3 with 2 N hydrochloric acid solution, added with 15% sodium chloride, and extracted three times with dichloromethane. The organic phases were combined, dried over anhydrous sodium sulfate, and filtered. The filtrate was concentrated at 50° C. to a viscous state and precipitated with diethyl ether. The obtained precipitate was dried under vacuum. 20 g of the crude product was prepared into an aqueous solution having a conductivity of 100 μs/cm, which was separated by a DEAE anion column. The sodium chloride aqueous solution eluate having a conductivity of 50 μs/cm was collected. The aqueous phase was adjusted to pH 2-3 with 2 N hydrochloric acid and extracted with dichloromethane. The organic phases were combined, dried over anhydrous sodium sulfate, and filtered. The filtrate was concentrated and precipitated with diethyl ether to give four-arm dodecaethylene glycol hydroxy-monoacetic acid.

NMR (DMSO) δ:

Four-arm dodecaethylene glycol hydroxy-monoacetic acid (III-1): 4.01 (s, 2H, $CH_2COOH$), 4.54 (t, 3H, $CH_2OH$).

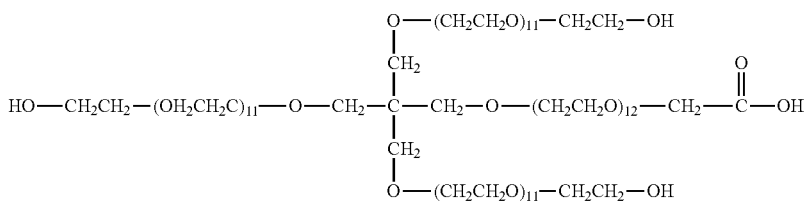

Example 19: Four-Arm Dodecaethylene Glycol Hydroxy-Methyl Monoacetate

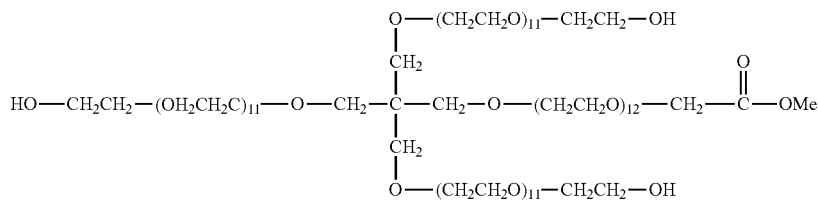

Steps:

In a single-neck round-bottom flask, 5 g of four-arm dodecaethylene glycol hydroxy-monoacetic acid was added and dissolved in 20 mL of anhydrous methanol and bathed in ice water, and 0.84 mL of concentrated sulfuric acid was added dropwise. The resulting mixture was reacted at room temperature for 3 hours. The system was adjusted to pH 7.0 with 8% sodium bicarbonate aqueous solution and extracted three times with dichloromethane. The organic phases were combined, dried over anhydrous magnesium sulfate and filtered. The filtrate was concentrated at 40° C. to a viscous state and precipitated with diethyl ether. The obtained precipitate was dried under vacuum to give four-arm dodecaethylene glycol hydroxy-methyl monoacetate.

NMR (DMSO) δ: 3.32 (s, 3H, $CH_2COOCH_3$), 4.03 (s, 2H, $CH_2COOCH_3$), 4.53 (t, 3H, $CH_2OH$).

Example 20: Four-Arm Dodecaethylene Glycol Sulfonate-Methyl Monoacetate

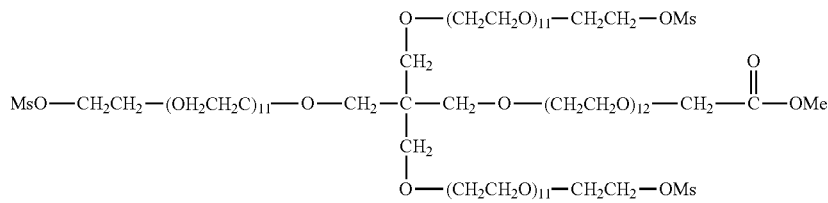

Steps:

In a three-neck round-bottom flask, nitrogen gas was introduced, and 5.0 g of four-arm dodecaethylene glycol hydroxy-methyl monoacetate was added and dissolved in 50 mL of toluene. The resulting mixture was heated, and 38 mL of toluene was distilled off. When the distillate was clear, the resulting mixture was cooled to room temperature, added with 13 mL of dichloromethane, and stirred for 10 minutes, added with 278 μL of triethylamine, and stirred for 5 minutes, and added dropwise with 150 μL of methylsulfonyl chloride. The resulting mixture was reacted overnight under closed conditions. On the next day, the reaction mixture was added with 900 μL of absolute ethanol, stirred for 15 minutes, and filtered. The filtrate was concentrated at 60° C. to a viscous state, dissolved in 60 mL of isopropanol under heating, then precipitated in an ice water bath, and filtered. The obtained filter cake was washed once with isopropanol and dried under vacuum to give four-arm dodecaethylene glycol sulfonate-methyl monoacetate.

NMR (DMSO) δ: 3.13 (s, 9H, $CH_2OSO_2CH_3$), 4.19 (s, 2H, $CH_2COOCH_3$), 4.31 (t, 6H, $CH_2OSO_2CH_3$).

Example 21: Four-Arm Dodecaethylene Glycol Azide-Methyl Monoacetate

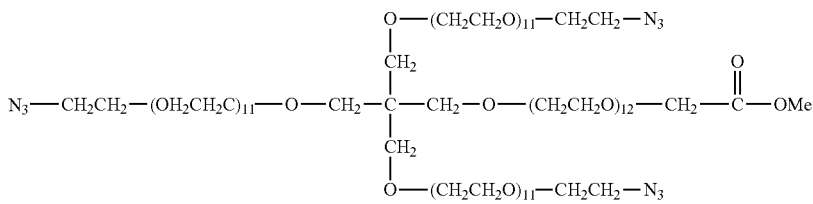

Steps:

In a three-neck round-bottom flask, nitrogen gas was introduced, and 5.0 g of four-arm dodecaethylene glycol sulfonate-methyl monoacetate and 0.7 g of sodium azide were added and dissolved in 25 mL of DMF. The mixture was heated to 90° C., reacted for 3 hours, then cooled to room temperature, added with 25 mL of water and 15% sodium chloride, and extracted with dichloromethane. The organic phase was dried over anhydrous sodium sulfate and filtered. The filtrate was concentrated, dissolved in 100 mL of isopropanol under heating, precipitated in an ice water bath, and filtered. The obtained filter cake was washed once with isopropanol and dried under vacuum to give four-arm dodecaethylene glycol azide-methyl monoacetate.

NMR (DMSO) δ: 4.13 (s, 2H, $CH_2COOCH_3$).

Example 22: Four-Arm Dodecaethylene Glycol Azide-Monoacetic Acid

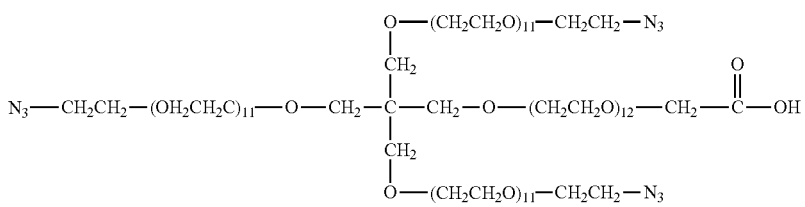

Steps:

In a 100 mL beaker, 5.0 g of four-arm dodecaethylene glycol azide-methyl monoacetate and de-aerated water were added. The system was adjusted to pH 12 with 0.2 N sodium hydroxide, then reacted under stirring at room temperature for 3 hours, and then adjusted to pH 2-3 with 1 N hydrochloric acid, added with 15% sodium chloride, and extracted with dichloromethane. The organic phase was dried over anhydrous sodium sulfate and filtered. The filtrate was concentrated, dissolved in 90 mL of isopropanol under heating, then precipitated in an ice water bath and filtered. The obtained filter cake was washed once with isopropanol and dried under vacuum to give four-arm dodecaethylene glycol azide-monoacetic acid.

NMR (DMSO) δ: 4.01 (s, 2H, $CH_2COOH$).

Example 23: Four-Arm Dodecaethylene Glycol Azide-Monoacetate Succinimidyl Ester

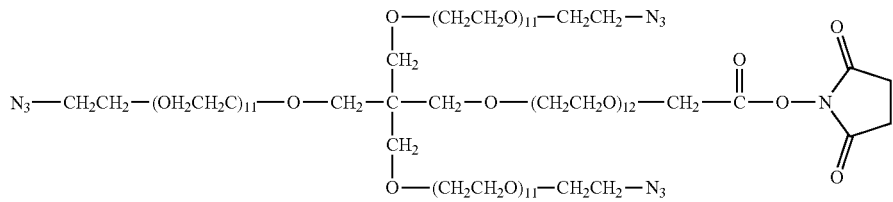

Steps:

In a 100 mL beaker, 2.0 g of four-arm dodecaethylene glycol sulfonate-methyl monoacetate and 50 mg of N,N-hydroxysuccinimide (NHS) were added and dissolved in 20 mL of dichloromethane, and 135 mg of dicyclohexylcarbodiimide (DCC) was added. The resulting mixture was reacted under stirring at room temperature for 2 hours and then filtered. The filtrate was concentrated, dissolved in 40 mL of isopropanol under heating, and then precipitated in an ice water bath and filtered. The obtained filter cake was washed once with isopropanol and dried under vacuum to give four-arm dodecaethylene glycol azide-monoacetate succinimidyl ester.

NMR (DMSO) δ: 2.81 (s, 4H,

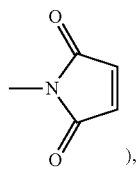

), 4.62 (s, 2H, $CH_2COO$).

Example 24: Synthesis of Four-Arm Dodecaethylene Glycol Amine-Monoacetic Acid

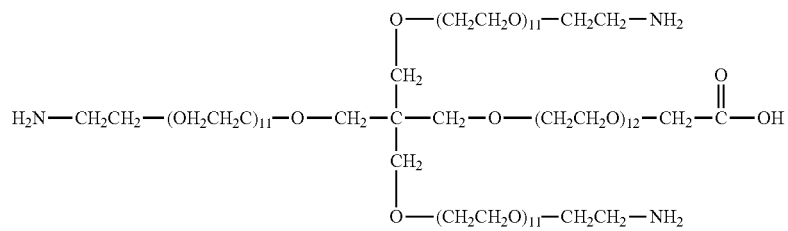

Steps:

In a three-neck round-bottom flask, 5 g of four-arm dodecaethylene glycol sulfonate-methyl monoacetate was added and dissolved in 7.8 mL of de-aerated water under nitrogen protection. The solution was adjusted to pH 12.0 with 2 N aqueous sodium hydroxide and reacted at room temperature for 2 to 2.5 hours. The system was added with 26 mL of an aqueous ammonia solution in which 1.3 g of ammonium chloride was dissolved, and reacted under stirring at room temperature for 72 hours. After the reaction was completed, the reaction mixture was added with 7 g of sodium chloride, and after dissolving, the reaction mixture was extracted three times with dichloromethane. The organic phases were combined, concentrated at 40° C. to dryness, then added with 30 mL of de-aerated water, and stirred for dissolution until the liquid was clear. The solution was adjusted to pH 2-3 with 2 N hydrochloric acid, added with 5 g of sodium chloride, and then extracted three times with dichloromethane. The organic phases were combined, dried over anhydrous sodium sulfate until the liquid was clarified, and filtered. The filtrate was concentrated at 40° C. to a viscous state, precipitated with 50 mL of diethyl ether and filtered. The obtained precipitate was dried under vacuum to give four-arm dodecaethylene glycol amine-monoacetic acid.

NMR (DMSO) δ: 2.96 (t, 6H, $CH_2CH_2NH_2$), 4.03 (s, 2H, $CH_2COOH$).

Example 25: Synthesis of Four-Arm Dodecaethylene Glycol Maleimide-Monoacetic Acid

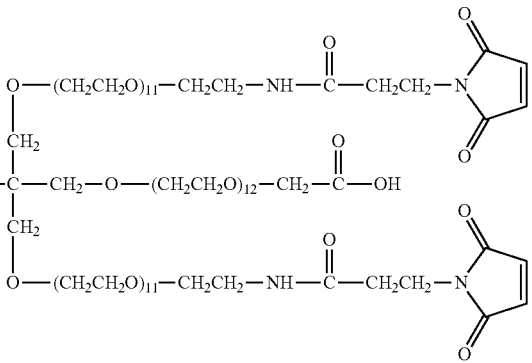

Steps:

In a single-neck round-bottom flask, 3.2 g of four-arm dodecaethylene glycol amine-monoacetic acid was added and dissolved in dichloromethane and bathed in ice water, and 500 μL of TEA and 1.06 g of MAL-NHS were added. The resulting mixture was reacted under stirring at room temperature for 12 hours or more. The reaction mixture was concentrated at 40° C. to dryness, added with 30 mL of de-aerated water and stirred, and washed with 20 mL of ethyl acetate. The aqueous phase was extracted three times with dichloromethane. The organic phases were combined, dried over anhydrous sodium sulfate until the liquid was clarified, and filtered. The filtrate was concentrated at 40° C. to a viscous state, and precipitated with 50 mL of isopropyl alcohol in ice water bath, and filtered. The obtained precipitate was dried under vacuum to give four-arm dodecaethylene glycol maleimide-monoacetic acid NMR (DMSO) δ: 2.32 (t, 6H,

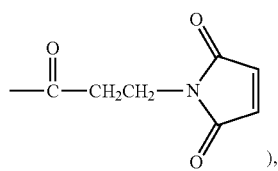), 3.13 (q, 6H, CH$_2$CH$_2$NH), 4.40 (s, 2H, CH$_2$COOH), 6.99 (s, 6H,

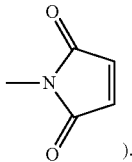).

Example 26: Four-Arm Dodecaethylene Glycol Maleimide-Monoacetate Succinimidyl Ester

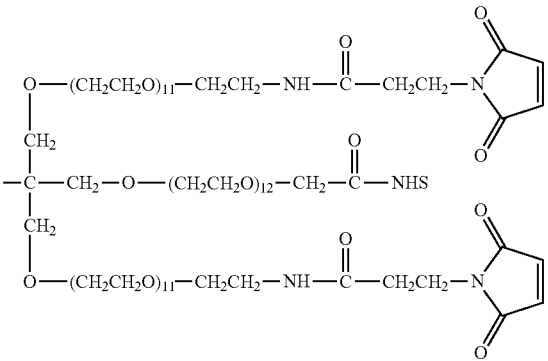

(MAL)$_3$-PEG12-NHS

Steps:

In a 100 mL beaker, 3.2 g of four-arm dodecaethylene glycol maleimide-monoacetic acid and 75 mg of NHS were added and dissolved in 20 mL of dichloromethane, and 150 mg of DCC was added. The resulting mixture was reacted under stirring at room temperature for 2 hours and filtered. The filtrate was concentrated, dissolved in 40 mL of isopropanol under heating, and then precipitated in an ice water bath, and filtered. The obtained filter cake was washed once with isopropanol and dried under vacuum to give four-arm dodecaethylene glycol maleimide-monoacetate succinimidyl ester.

NMR (DMSO) δ: 2.32 (t, 6H,

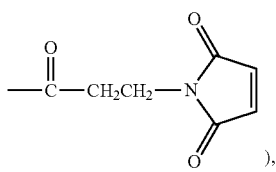

), 2.82 (s, 4H,

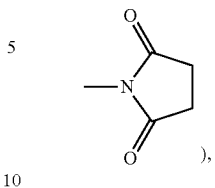

), 3.15 (q, 6H, CH$_2$CH$_2$NH), 4.60 (s, 2H, CH$_2$COO), 6.99 (s, 6H,

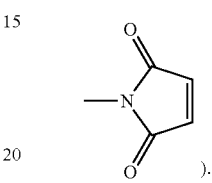

).

Synthesis Examples of [PEG-2]

The reactions in Examples 27 to 35 are as shown in Scheme 1.

Scheme 1

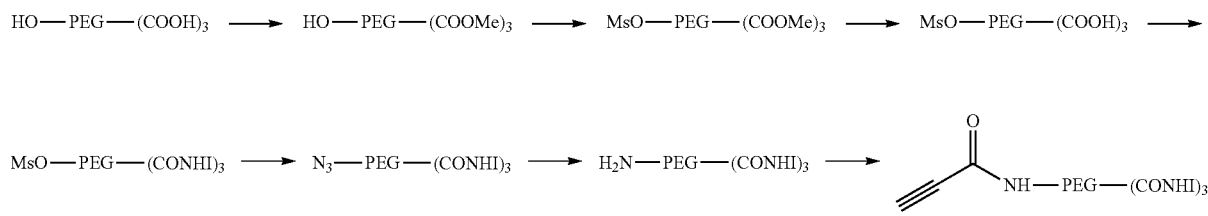

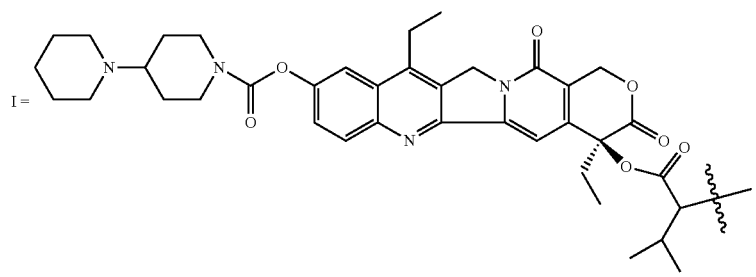

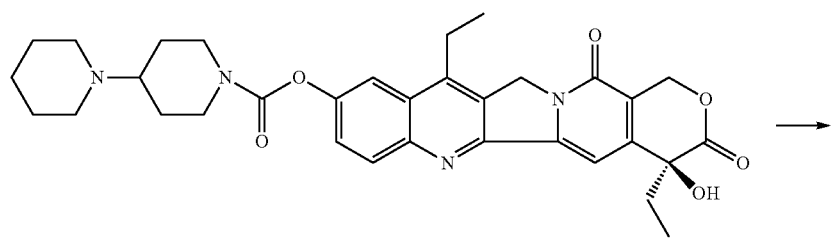

-continued

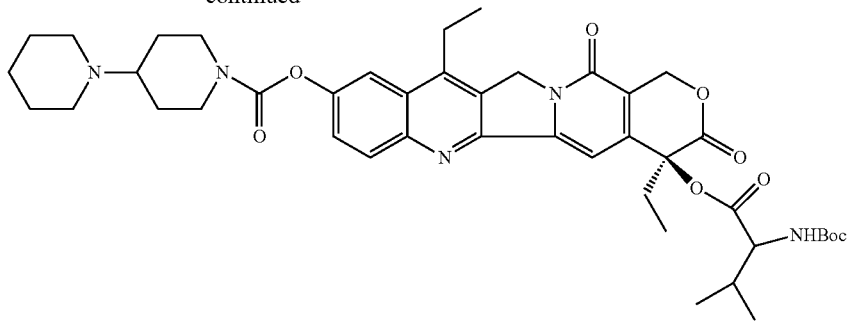

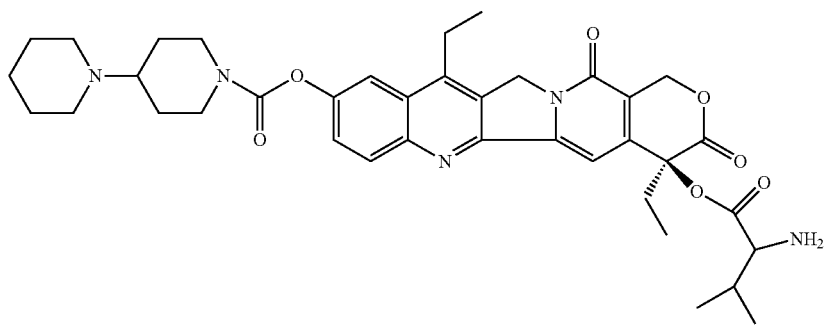

Example 27: Preparation of Four-Arm Polyethylene Glycol Methyl Carboxylate-Monohydroxy (5 K) (T1-1)

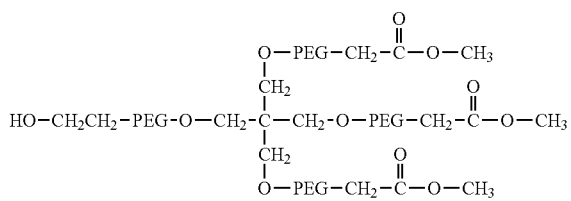

50 g of monohydroxytricarboxy four-arm polyethylene glycol (5 K) was dissolved in methanol. Thionyl chloride was added dropwise thereto. After the completion of the dropwise addition, the resulting mixture was further reacted under stirring at room temperature for 3 h. The reaction mixture was concentrated. The residue was dissolved with isopropanol under heating and cooled to precipitate a solid, and filtered. The obtained filter cake was dried under vacuum overnight to give a white solid. $^1$H NMR (300 MHz, DMSO-$d_6$) δ: 3.31 (s, 9H, CH$_2$COOCH$_3$), 4.12 (s, 6H, CH$_2$COOCH$_3$), 4.55 (t, 1H, CH$_2$OH).

Example 28: Preparation of Four-Arm Polyethylene Glycol Methyl Carboxylate-Monohydroxymethanesulfonate (5 K) (T1-2)

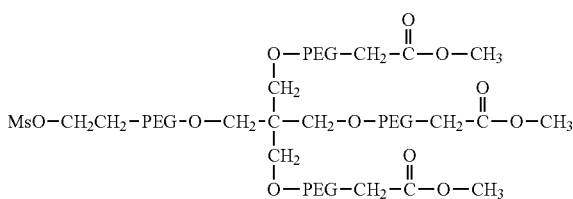

45 g of four-arm polyethylene glycol methyl carboxylate-monohydroxy (5 K) was dissolved in dichloromethane. Triethylamine was added thereto. The resulting mixture was stirred evenly. Further, methanesulfonyl chloride was added dropwise thereto. After the completion of the dropwise addition, the resulting mixture was further reacted under stirring at room temperature overnight. The reaction mixture was concentrated, and the residue was dissolved with isopropanol under heating, and cooled to precipitate a solid, and filtered. The obtained filter cake was dried under vacuum overnight to give a white solid product. $^1$H NMR (300 MHz, DMSO-$d_6$) δ: 3.13 (s, 3H, CH$_2$OSO$_2$CH$_3$), 4.17 (s, 6H, CH$_2$COOCH$_3$), 4.30 (t, 2H, CH$_2$OSO$_2$CH$_3$).

Example 29: Preparation of Four-Arm Polyethylene Glycol Carboxylic Acid-Monohydroxymethanesulfonate (5 K) (T1-3)

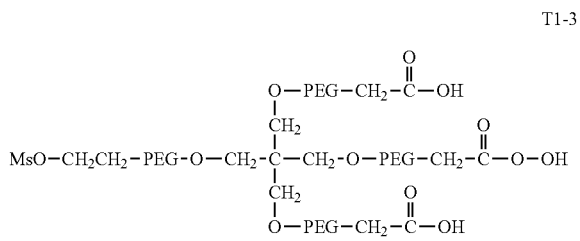

T1-3

42 g of four-arm polyethylene glycol methyl carboxylate-monohydroxymethanesulfonate was dissolved in methanol. 1 N sodium hydroxide solution was added thereto. The system was heated to reflux for 3 h, cooled, and then acidified with dilute hydrochloric acid. The reaction mixture was concentrated under reduced pressure. The residue was added with water and extracted with dichloromethane. The extract was washed with saturated brine, dried, filtered and then concentrated. The residue was dissolved with isopropanol under heating, and cooled to precipitate a solid, and filtered. The obtained filter cake was dried under vacuum overnight to give a white solid product. $^1$H NMR (300 MHz, DMSO-$d_6$) δ: 3.13 (s, 3H, $CH_2OSO_2CH_3$), 4.01 (s, 6H, $CH_2COOH$), 4.30 (t, 2H, $CH_2OSO_2CH_3$).

Example 30: Preparation of N-Tert-Butoxycarbonyl Valine Irinotecan Ester (D1-1)

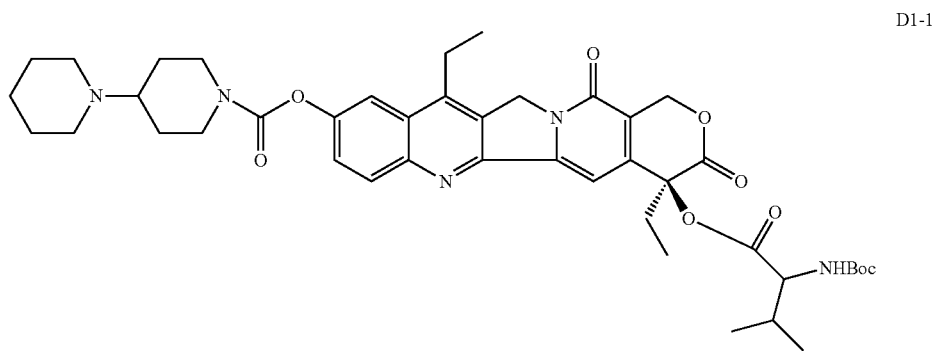 [SMILES: CCc1c2c(nc3ccc(OC(=O)N4CCC(N5CCCCC5)CC4)cc13)-c1cc3c(c(=O)n1C2)COC(=O)[C@@]3(CC)OC(=O)C(NC(=O)OC(C)(C)C)C(C)C]

D1-1

Irinotecan base (13.0 g, 22.2 mmol) was dissolved in dichloromethane (500 mL), and N-tert-butoxycarbonylvaline (9.63 g, 44.4 mmol) and DMAP (5.42 g, 44.4 mmol) were added. A solution of EDC (12.80 g, 66.7 mmol) in dichloromethane (280 mL) was added dropwise under nitrogen protection. After the completion of the dropwise addition, the system was reacted at room temperature overnight. When TLC monitoring showed that the reaction was complete, the reaction mixture was washed with distilled water (500 mL) and a saturated sodium chloride solution (500 mL), dried over anhydrous sodium sulfate, and concentrated to dryness. The residue was purified by a silica gel column, precipitated with isopropyl ether, and dried under vacuum at room temperature to give a pale yellow solid (12.63 g, yield: 72.4%). $^1$H NMR (300 MHz, DMSO-$d_6$) δ: 8.07 (d, 1H), 7.92 (d, 1H), 7.66 (dd, 1H), 7.43 (m, 1H), 7.15 (s, 1H), 5.47 (s, 2H), 5.12 (s, 2H), 4.36 (m, 1H), 3.86-3.61 (m, 4H), 2.92-2.74 (m, 3H), 2.49 (m, 4H), 2.29 (d, 1H), 2.16-2.10 (m, 2H), 1.83-1.52 (m, 10H), 1.47 (s, 9H), 1.31 (s, 3H), 0.93 (m, 9H).

Example 31: Preparation of Valine Irinotecan Ester (D1-2)

D1-2

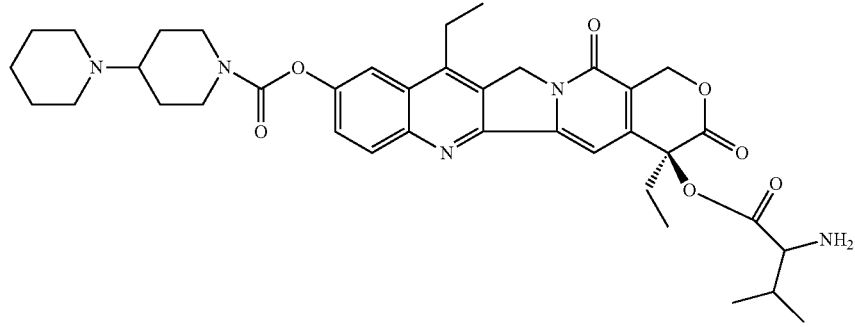

N-tert-butoxycarbonylvaline irinotecan ester (12.0 g, 16.1 mmol) was dissolved in dichloromethane (240 mL), and trifluoroacetic acid (120 mL) was added thereto. The resulting mixture was reacted under stirring at room temperature for 3 h. When TLC monitoring showed that the reaction was complete, the reaction mixture was evaporated under reduced pressure to remove solvent, then dissolved with dichloromethane (500 mL), and then concentrated to dryness, which was repeated several times until most of the trifluoroacetic acid was removed. The resulting mixture was precipitated with isopropyl ether (500 mL) and filtered. The obtained filter cake was washed with isopropyl ether (200 mL) and dried under vacuum at room temperature to give a pale yellow solid (13.4 g, yield: 95.3%). $^1$H NMR (300 MHz, DMSO-$d_6$) δ: 7.93 (d, 1H), 7.65 (dd, 1H), 7.42 (m, 1H), 7.11 (s, 1H), 5.35 (s, 2H), 5.07 (s, 2H), 4.28 (m, 1H), 3.81-3.59 (m, 4H), 2.87-2.66 (m, 3H), 2.33 (m, 4H), 2.21 (d, 1H), 2.06-1.97 (m, 2H), 1.75-1.51 (m, 10H), 1.32 (s, 3H), 0.92 (m, 9H).

Example 32: Preparation of Four-Arm Polyethylene Glycol Tricarboxylate(Valine Irinotecan Ester) Ester-Monohydroxymethanesulfonyl Ester (5 K) (T1-4)

T1-4

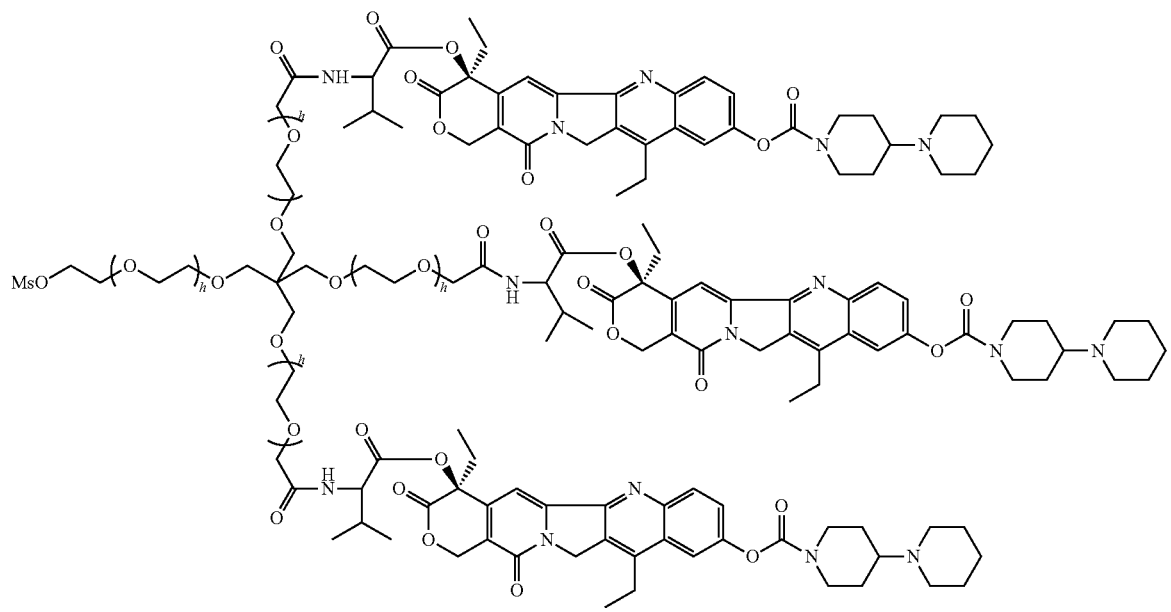

Four-arm polyethylene glycol carboxylic acid-monohydroxymethanesulfonate (5 K) was dissolved in dichloromethane (500 mL), and valine irinotecan ester and DMAP were added thereto. Under nitrogen protection, the resulting mixture was cooled and added dropwise with a solution of EDC (12.80 g, 66.6 mmol) in dichloromethane (280 mL). After the completion of the dropwise addition, the ice bath was removed. The system was naturally warmed to room temperature and reacted overnight. When the HPLC monitoring showed that the macromolecular starting material was completely reacted, the reaction mixture was concentrated, and the residue was dissolved with isopropanol under heating, and after cooling, it was crystallized, and filtered. The obtained crystals were dried under vacuum overnight to give a product. $^1$H NMR (300 MHz, DMSO-$d_6$) δ: 8.09 (d, 3H), 7.92 (d, 3H), 7.67 (dd, 3H), 7.43 (m, 3H), 7.12 (s, 3H), 5.37 (s, 6H), 5.03 (s, 6H), 4.35-4.22 (m, 9H), 4.07 (s, 18H), 3.81-3.49 (m, 450H), 3.13 (s, 9H), 2.86-2.67 (m, 9H), 2.35 (m, 12H), 2.28 (d, 3H), 2.09-1.98 (m, 6H), 1.76-1.53 (m, 30H), 1.31 (s, 9H), 0.91 (m, 27H).

Example 33: Preparation of Four-Arm Polyethylene Glycol Tricarboxylate(Valine Irinotecan Ester) Ester-Monoazide (5 K) (T1-5)

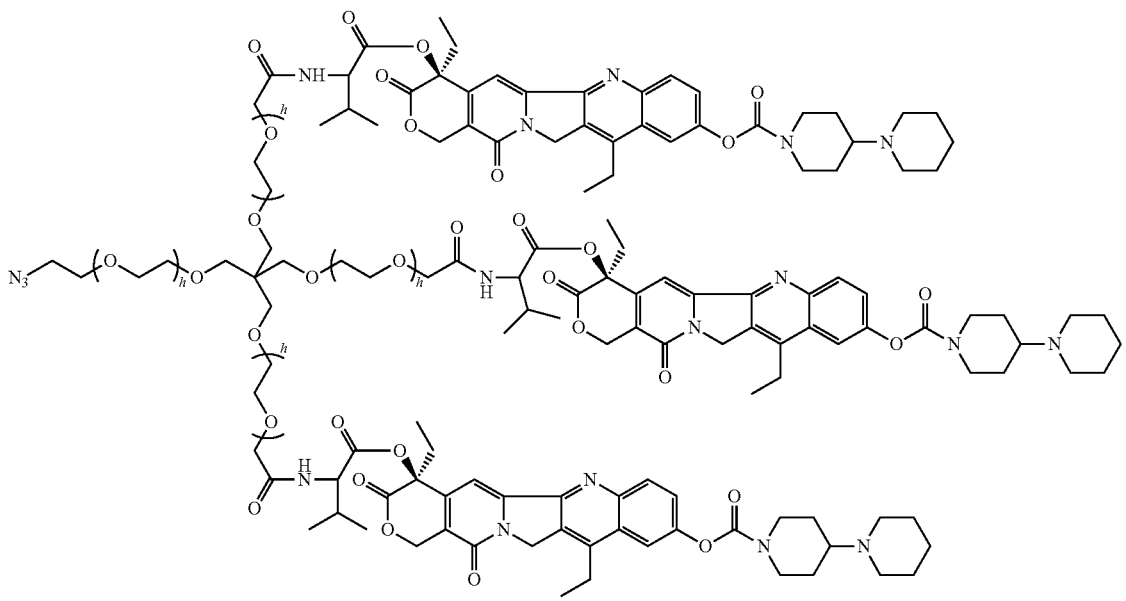

T1-5

Four-arm polyethylene glycol tricarboxylate(valine irinotecan ester) ester-monohydroxymethanesulfonyl ester(5 K) was dissolved in DMF, and sodium azide was added thereto. The system was heated to 90° C. and reacted for 3 h, then cooled and recrystallized from isopropanol to give a product. $^1$H NMR (300 MHz, DMSO-$d_6$) δ: 8.07 (d, 3H), 7.93 (d, 3H), 7.65 (dd, 3H), 7.44 (m, 3H), 7.15 (s, 3H), 5.38 (s, 6H), 5.04 (s, 6H), 4.36-4.24 (m, 12H), 4.05 (s, 18H), 3.82-3.48 (m, 450H), 2.88-2.69 (m, 9H), 2.33 (m, 12H), 2.25 (d, 3H), 2.11-1.96 (m, 6H), 1.77-1.54 (m, 30H), 1.32 (s, 9H), 0.92 (m, 27H).

Example 34: Preparation of Four-Arm Polyethylene Glycol Tricarboxylate(Valine Irinotecan Ester) Ester-Monoamine (5 K) (T1-6)

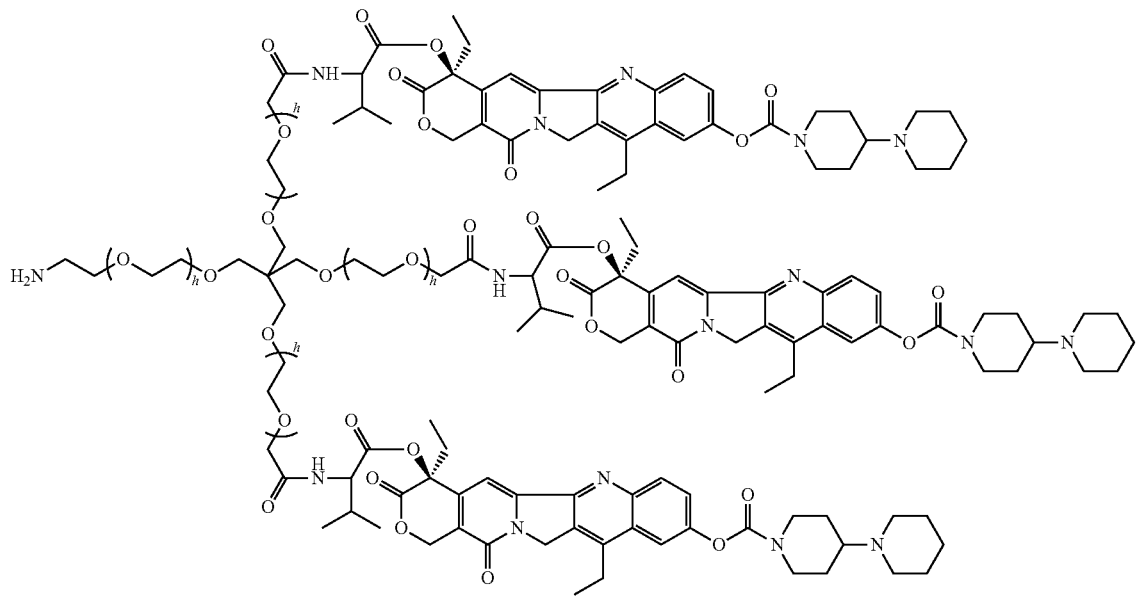

T1-6

Four-arm polyethylene glycol tricarboxylate(valine irinotecan ester) ester-monoazide (5 K) was dissolved in dichloromethane, and triphenyl phosphine was added thereto. The resulting mixture was reacted at room temperature overnight. The reaction mixture was concentrated, and the residue was recrystallized from isopropanol to give a product. $^1$H NMR (300 MHz, DMSO-$d_6$) δ: 8.06 (d, 3H), 7.91 (d, 3H), 7.66 (dd, 3H), 7.45 (m, 3H), 7.17 (s, 3H), 5.35 (s, 6H), 5.02 (s, 6H), 4.36-4.24 (m, 12H), 4.07 (s, 18H), 3.82-3.48 (m, 450H), 2.88-2.69 (m, 9H), 2.35 (m, 12H), 2.26 (d, 3H), 2.11-1.96 (m, 6H), 1.77-1.54 (m, 30H), 1.31 (s, 9H), 0.91 (m, 27H).

Example 35: Preparation of Four-Arm Polyethylene Glycol Tricarboxylate(Valine Irinotecan Ester) Ester-Monoaminopropynamide (5 K) (T1-7)

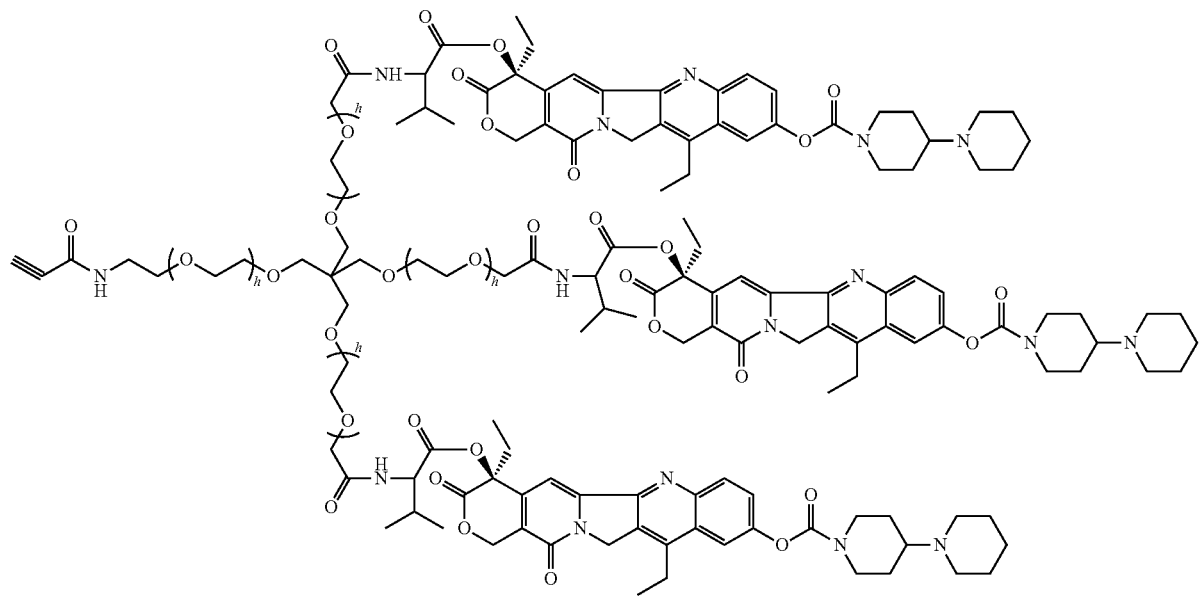

T1-7

Propargylic acid was dissolved in dichloromethane (500 mL), and four-arm polyethylene glycol tricarboxylate(valine irinotecan ester) ester-monoamine (5 K) and DMAP were added thereto. Under nitrogen protection, the resulting mixture was cooled and added dropwise with a solution of EDC (12.80 g, 66.6 mmol) in dichloromethane (280 mL). After the completion of the dropwise addition, the ice bath was removed. The system was naturally warmed to room temperature and reacted overnight. When the HPLC monitoring showed that the macromolecular starting material was completely reacted, the reaction mixture was concentrated, and the residue was dissolved with isopropanol under heating, and after cooling, it was crystallized, and filtered. The obtained crystals were dried under vacuum overnight to give a product. $^1$H NMR (300 MHz, DMSO-$d_6$) δ: 8.09 (s, 1H), 8.06 (d, 3H), 7.91 (d, 3H), 7.66 (dd, 3H), 7.45 (m, 3H), 7.17 (s, 3H), 5.35 (s, 6H), 5.02 (s, 6H), 4.36-4.24 (m, 9H), 4.07 (s, 18H), 3.82-3.48 (m, 450H), 2.88-2.69 (m, 12H), 2.35 (m, 12H), 2.26 (d, 3H), 2.11-1.96 (m, 6H), 1.77-1.54 (m, 30H), 1.31 (s, 9H), 0.92 (m, 27H).

The reactions in Examples 36 to 39 are as shown in Scheme 2.

To a reaction flask, 32.0 g (0.4 mmol) of HS-PEG-(COOH) and 440.3 mg (2 mmol) of Py-S—S-Py were added and dissolved in methanol. The resulting mixture was reacted under stirring at room temperature overnight. The reaction mixture was concentrated to dryness. The residue was crystallized from isopropanol and filtered. The obtained crystals were dried to give a white solid (1.6 g). $^1$H NMR (300 MHz, DMSO-$d_6$) δ: 8.57 (s, 1H), 7.66 (s, 1H), 7.29 (s, 1H), 7.24 (s, 1H), 4.19 (s, 6H).

Example 38: Preparation of Py-S—S-PEG-(CONHI)$_3$(5 K)(T2-3)

Py-S—S-PEG-(CONHI)$_3$     T2-3

To a reaction flask, 2.5 g (0.5 mmol) of Py-SS-PEG-(COOH)$_3$, 4.3 g (5.25 mmol) of valine irinotecan ester trifluoroacetate and 932 mg (7 mmol) of HOBt were added and dissolved in dichloromethane, and then 1.8 mL (10.5 mmol) of diisopropylethylamine was added thereto. The resulting mixture was stirred well. 1.34 g (7 mmol) of EDCI was added thereto. After the completion of the addition, the Scheme 2

MsO—PEG—(COOMe)$_3$ → HS—PEG—(COOH)$_3$ → Py—S—S—PEG—(COOH)$_3$ →
Py—S—S—PEG—(CONHI)$_3$ → HS—PEG—(CONHI)$_3$

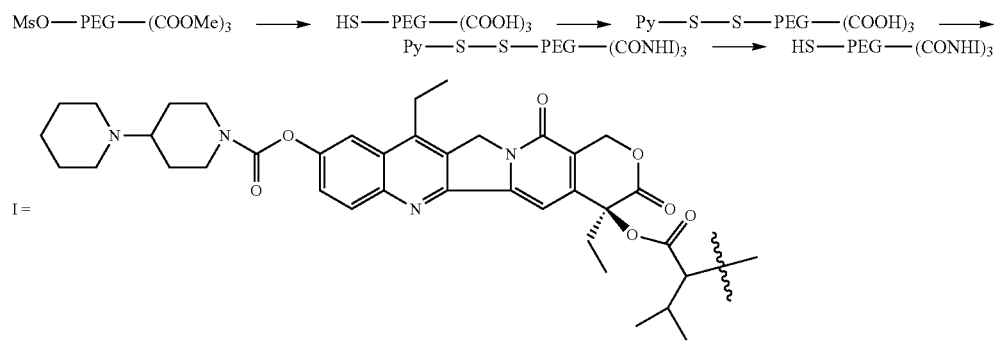

I =

Example 36: Preparation of Sulfydryl Polyethylene Glycol Tricarboxylic Acid (5 K) (T2-1)

HS-PEG-(COOH)$_3$     T2-1

To a reaction flask, 3.0 g (0.6 mmol) of polyethylene glycol methyl tricarboxylate-monohydroxymethanesulfonate (5 K) and 274 mg (3.6 mmol) of thiourea were added, and 30 mL of absolute ethanol was added. The resulting mixture was refluxed overnight. The reaction mixture was concentrated, added with 30 mL of water, and transferred to a three-necked flask, which was protected with nitrogen. 278 mg (1.8 mmol) of DTT and sodium hydroxide solution were added thereto. The resulting mixture was reacted under stirring at room temperature for 4 h. The reaction mixture was acidified and washed with ethyl acetate. The aqueous layer was extracted three times with dichloromethane. The organic phases were combined, washed with saturated brine, dried, filtered and then concentrated. The residue was crystallized from isopropanol and filtered. The obtained crystals were dried to give a white solid (1.8 g). $^1$H NMR (300 MHz, DMSO-$d_6$) δ: 4.19 (s, 6H).

Example 37: Protection of Sulfydryl Polyethylene Glycol Heptacarboxylic Acid (5 K) (T2-2)

Py-S—S-PEG-(COOH)$_3$     T2-2 resulting mixture was stirred at room temperature overnight. The reaction mixture was concentrated to dryness. The residue was crystallized from isopropanol and filtered. The obtained crystals were dried to give a white solid (2.2 g). $^1$H NMR (300 MHz, DMSO-$d_6$) δ: 8.57 (s, 1H), 8.09 (d, 3H), 7.92 (d, 3H), 7.67 (m, 8H), 7.43 (m, 3H), 7.29 (s, 1H), 7.24 (s, 1H), 7.12 (s, 3H), 5.37 (s, 2H), 5.03 (s, 2H), 4.35-4.22 (m, 9H), 4.19 (s, 6H), 4.07 (s, 6H), 3.13 (s, 3H), 2.86-2.67 (m, 9H), 2.35 (m, 8H), 2.28 (d, 3H), 2.09-1.98 (m, 6H), 1.76-1.53 (m, 30H), 1.31 (s, 9H), 0.91 (m, 9H).

Example 39: Preparation of SH-PEG-(CONHI)$_3$(5 K)(T2-4)

HS-PEG-(CONHI)$_3$

SH-4ARMPEG5K—(CONHI)$_3$     T2-4

1.5 g (0.3 mmol) of the starting material Py-S—S-PEG-(CONHI)$_3$ was dissolved in dichloromethane, and DTT and triethylamine were added thereto. The resulting mixture was stirred at room temperature overnight. The reaction mixture was concentrated to dryness. The residue was crystallized from isopropanol and filtered. The obtained crystals were dried to give a white solid (1.2 g). $^1$H NMR (300 MHz, DMSO-$d_6$) δ: 8.09 (d, 3H), 7.92 (d, 3H), 7.67 (m, 3H), 7.43 (m, 3H), 7.12 (s, 3H), 5.37 (s, 6H), 5.03 (s, 6H), 4.35-4.22

(m, 9H), 4.19 (s, 6H), 4.07 (s, 6H), 3.13 (s, 9H), 2.86-2.67 (m, 9H), 2.35 (m, 4H), 2.28 (d, 3H), 2.09-1.98 (m, 6H), 1.76-1.53 (m, 30H), 1.31 (s, 9H), 0.91 (m, 9H).

The reactions in Examples 40 to 41 are as shown in Scheme 3.

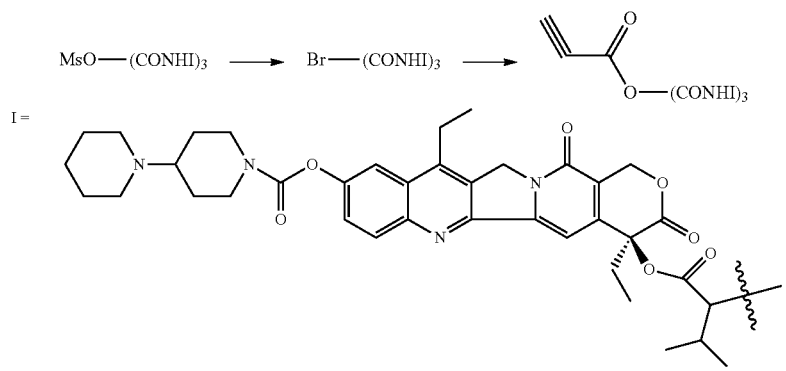

Scheme 3

Example 40: Preparation of Four-Arm Polyethylene Glycol Tricarboxylate(Valine Irinotecan Ester) Ester-Monobromo (5 K) (T3-1)

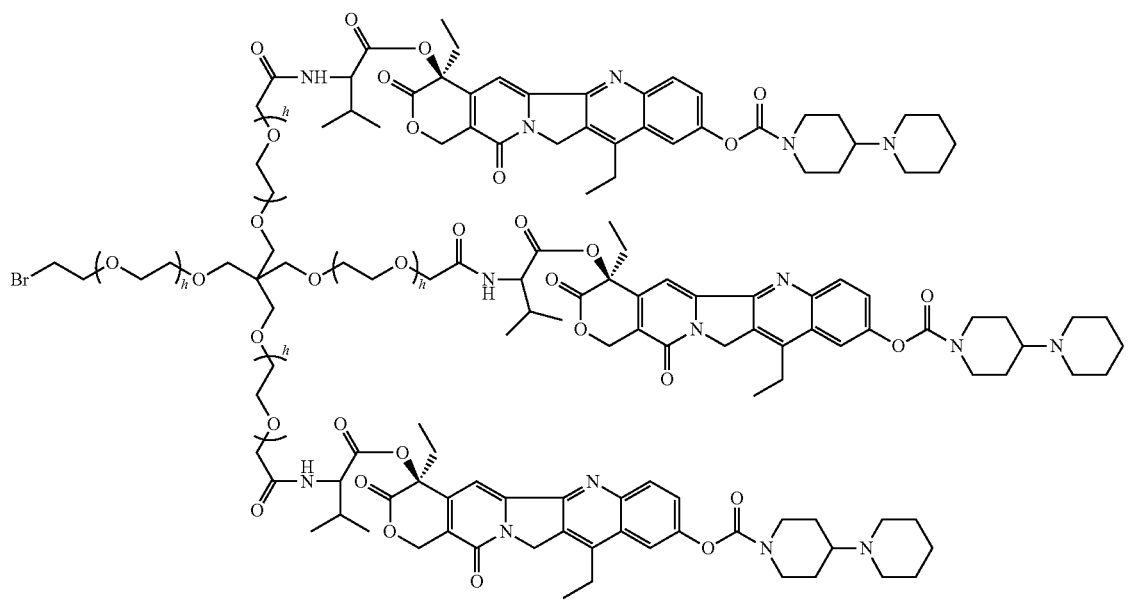

10 g of four-arm polyethylene glycol tricarboxylate (valine irinotecan ester) ester-monohydroxymethanesulfonyl ester (5 K) was dissolved in dichloromethane, and tetrabutylammonium bromide was added thereto. The resulting mixture was reacted at room temperature overnight. The reaction mixture was concentrated. The residue was dissolved with isopropanol under heating, crystallized after cooling, and filtered. The obtained crystals were dried to give a product. $^1$H NMR (300 MHz, DMSO-$d_6$) δ: 8.06 (d, 3H), 7.91 (d, 3H), 7.66 (dd, 3H), 7.45 (m, 3H), 7.17 (s, 3H), 5.35 (s, 6H), 5.02 (s, 6H), 4.36-4.24 (m, 9H), 4.07 (s, 18H), 3.82-3.48 (m, 450H), 2.88-2.69 (m, 9H), 2.35 (m, 12H), 2.26 (d, 3H), 2.11-1.96 (m, 6H), 1.77-1.54 (m, 30H), 1.31 (s, 9H), 0.92 (m, 27H).

Example 41: Preparation of Four-Arm Polyethylene Glycol Tricarboxylate(Valine Irinotecan Ester) Ester-Monohydroxy (Propiolate) Ester (5 K) (T3-2)

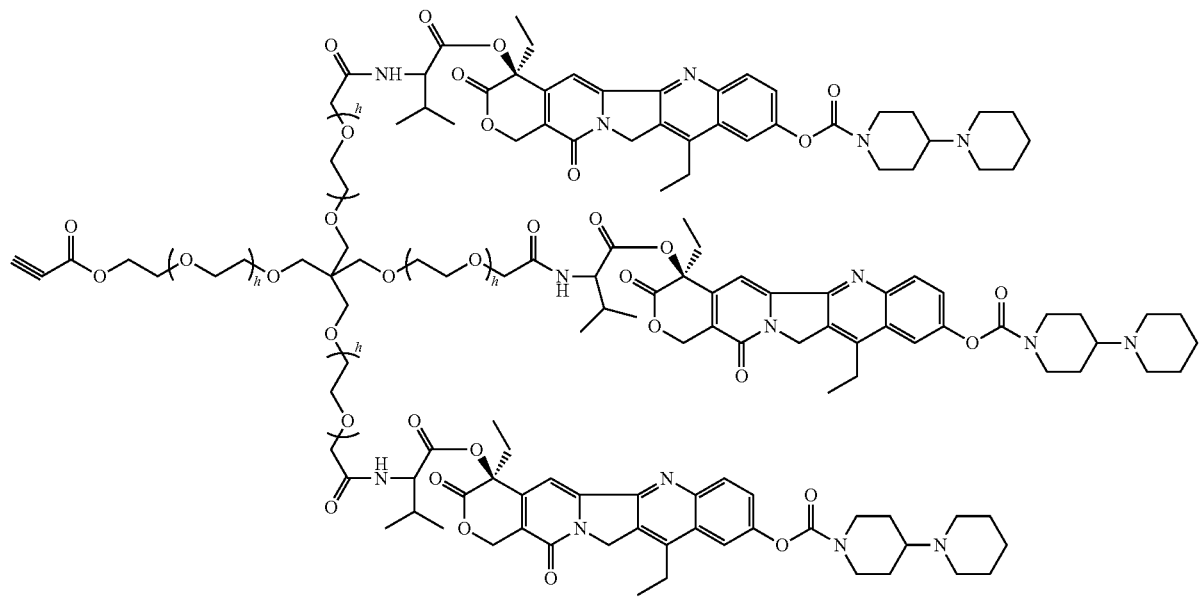

T3-2

Propargylic acid was dissolved in dichloromethane (500 mL), and four-arm polyethylene glycol tricarboxylate (valine irinotecan ester) ester-monobromo (5 K) and DMAP were added thereto. Under nitrogen protection, the resulting mixture was cooled and then added dropwise with a solution of EDC (12.80 g, 66.6 mmol) in dichloromethane (280 mL). After the completion of the dropwise addition, the ice bath was removed. The system was naturally warmed to room temperature and reacted overnight. When the HPLC monitoring showed that the macromolecular starting material was completely reacted, the reaction liquid was concentrated, and the residue was dissolved with isopropanol by heating, crystallized after cooling, and filtered. The obtained crystals were dried under vacuum overnight to give a product. $^1$H NMR (300 MHz, DMSO-$d_6$) δ: 8.06 (d, 3H), 7.91 (d, 3H), 7.66 (dd, 3H), 7.45 (m, 3H), 7.17 (s, 3H), 5.35 (s, 6H), 5.02 (s, 6H), 4.36-4.24 (m, 9H), 4.07 (s, 18H), 3.82-3.48 (m, 450H), 2.88-2.69 (m, 12H), 2.35 (m, 12H), 2.26 (d, 3H), 2.11-1.96 (m, 6H), 1.77-1.54 (m, 30H), 1.31 (s, 9H), 0.91 (m, 27H).

The reactions in Examples 42 to 45 are as shown in Scheme 4.

Scheme 4

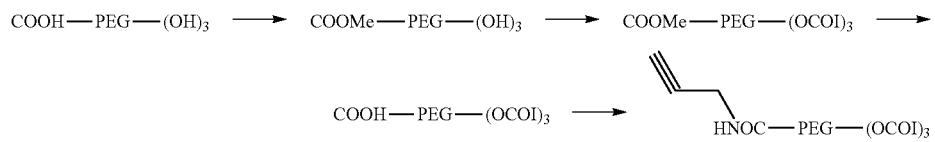

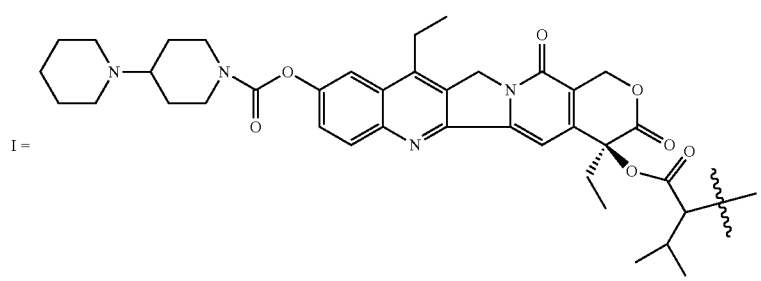

Example 42: Preparation of Four-Arm Polyethylene Glycol Hydroxy-Methyl Monoacetate (5 K) (T4-1)

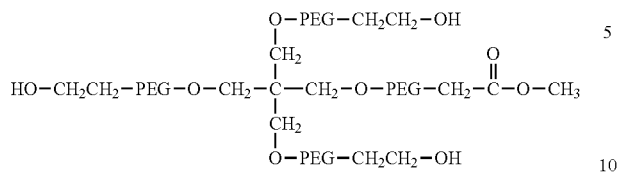

T4-1

50 g of four-arm polyethylene glycol hydroxy-monoacetic acid (5 K) was dissolved in methanol, and thionyl chloride was added dropwise thereto. After the completion of the dropwise addition, the resulting mixture was further reacted under stirring at room temperature for 3 h. The reaction mixture was concentrated. The residue was dissolved with isopropanol under heating, and cooled to precipitate a solid, and filtered. The obtained filter cake was dried under vacuum overnight to give a white solid product. $^1$H NMR (DMSO-$d_6$) δ: 3.32 (s, 3H, CH$_2$COOCH$_3$), 4.13 (s, 2H, CH$_2$COOCH$_3$), 4.57 (t, 3H, CH$_2$OH).

Example 43: Preparation of Four-Arm Polyethylene Glycol Methyl Monoacetate Tris(Irinotecan)Carbonate (5 K) (T4-2)

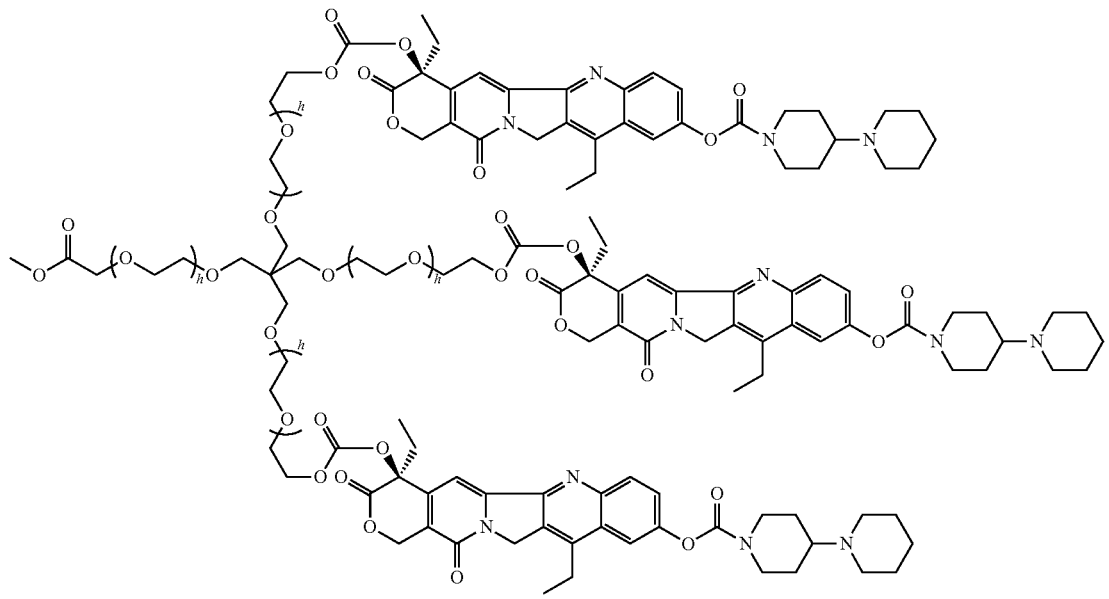

T4-2

5.9 g of irinotecan was dissolved in dichloromethane, and 3.7 g of 4,4-dimethylaminopyridine was added thereto. The resulting mixture was cooled under nitrogen protection. A solution of 3 g of diphosgene in dichloromethane was added dropwise. After the completion of the dropwise addition, the resulting mixture was naturally warmed to room temperature. After reacting for 30 minutes, four-arm polyethylene glycol hydroxy-methyl monoacetate (5 K) was further added thereto. After the completion of the addition, the resulting mixture was reacted at room temperature overnight. The reaction mixture was concentrated. The residue was dissolved with isopropanol under heating, and cooled to precipitate a solid, and filtered. The obtained filter cake was dried under vacuum overnight to give a pale yellow solid product. $^1$H NMR (300 MHz, DMSO-$d_6$) δ: 7.93 (d, 3H), 7.65 (dd, 3H), 7.44 (m, 3H), 7.15 (s, 3H), 5.38 (s, 6H), 5.04 (s, (6, H), 4.36-4.24 (m, 9H), 4.05 (s, 18H), 3.82-3.48 (m, 450H), 3.12 (s, 9H), 2.88-2.69 (m, 9H), 2.33 (m, 12H), 2.25 (d, 3H), 2.11-1.96 (m, 2H), 1.77-1.54 (m, 10H), 1.32 (s, 3H), 0.95 (m, 3H).

Example 44: Preparation of Four-Arm Polyethylene Glycol Monoacetic Acid Tris(Irinotecan)Carbonate (5 K) (T4-3)

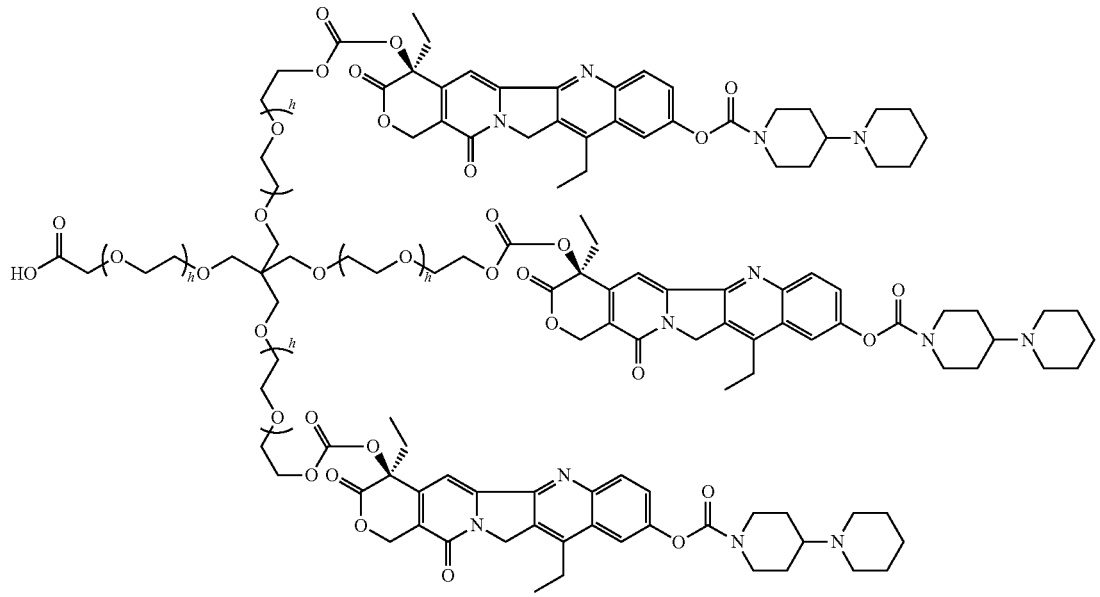

T4-3

10 g of four-arm polyethylene glycol methyl monoacetate tris(irinotecan)carbonate (5 K) was dissolved in methanol, and 1 N sodium hydroxide solution was added thereto. The resulting mixture was heated to reflux. After the reaction was completed, the reaction mixture was cooled, acidified with dilute hydrochloric acid, and then concentrated. The residue was dissolved with isopropanol under heating, and cooled to precipitate a solid, and filtered. The obtained filter cake was dried under vacuum overnight to give a product. $^1$H NMR (300 MHz, DMSO-$d_6$) δ: 7.93 (d, 3H), 7.65 (dd, 3H), 7.44 (m, 3H), 7.15 (s, 3H), 5.38 (s, 6H), 5.04 (s, 6H), 4.36-4.24 (m, 9H), 4.05 (s, 18H), 3.82-3.48 (m, 450H), 2.88-2.69 (m, 9H), 2.33 (m, 12H), 2.25 (d, 3H), 2.11-1.96 (m, 6H), 1.77-1.54 (m, 30H), 1.32 (s, 9H), 0.95 (m, 9H).

Example 45: Preparation of Four-Arm Polyethylene Glycol Monoacetic Acid (N-Propargyl)Amide Tris (Irinotecan)Carbonate (5 K) (T4-4)

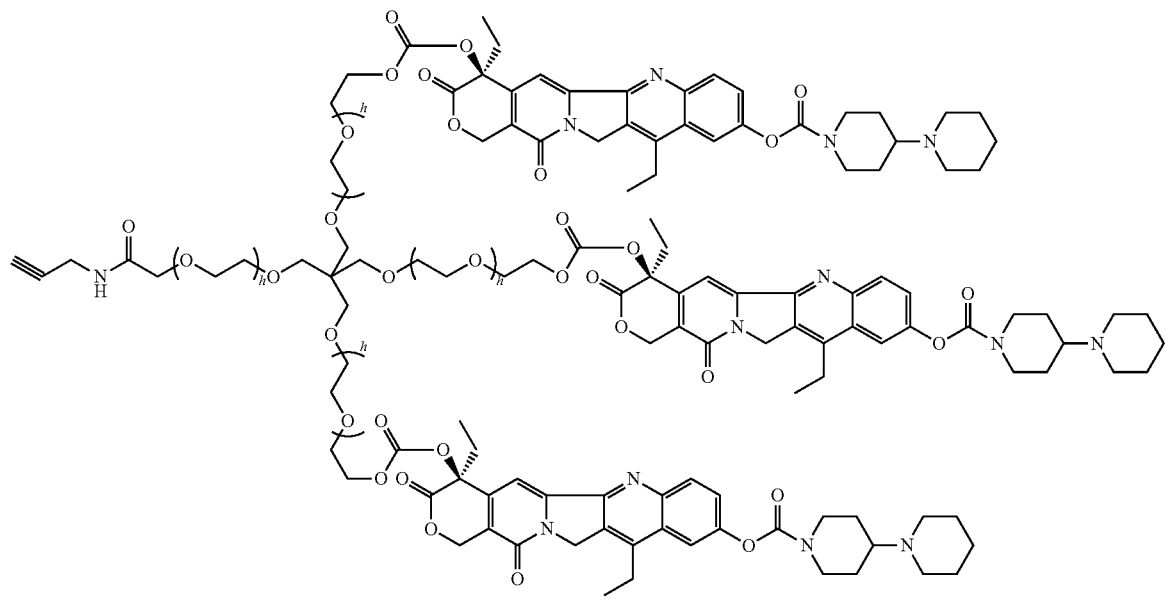

T4-4

Four-arm polyethylene glycol monoacetic acid tris(irinotecan)carbonate (5 K) was dissolved in dichloromethane, and propargylamine and DMAP were added thereto. Under nitrogen protection, the resulting mixture was cooled, and then added dropwise with a solution of EDC in dichloromethane. After the completion of the dropwise addition, the ice bath was removed. The system was naturally warmed to room temperature and reacted overnight. When the HPLC monitoring showed that the macromolecular starting material was completely reacted, the reaction mixture was concentrated. The residue was dissolved with isopropanol under heating, crystallized after cooling, and filtered. The obtained crystals were dried under vacuum overnight to give a product. $^1$H NMR (300 MHz, DMSO-$d_6$) δ: 7.93 (d, 3H), 7.65 (dd, 3H), 7.44 (m, 3H), 7.15 (s, 3H), 5.38 (s, 6H), 5.04 (s, 6H), 4.36-4.24 (m, 9H), 4.05 (s, 18H), 3.82-3.48 (m, 450H), 2.88-2.69 (m, 12H), 2.33 (m, 12H), 2.25 (d, 3H), 2.11-1.96 (m, 6H), 1.77-1.54 (m, 30H), 1.32 (s, 9H), 0.94 (m, 3H).

The reactions in Examples 46 to 51 are shown in Scheme 5.

Preparation of SH-PEG-CONHI ylamine was added thereto. The resulting mixture was stirred well. Methanesulfonyl chloride was added dropwise thereto. After the completion of the dropwise addition, the resulting mixture was further reacted under stirring at room temperature overnight. The reaction mixture was concentrated. The residue was dissolved with isopropanol under heating, and cooled to precipitate a solid, and filtered. The obtained filter cake was dried under vacuum overnight to give a white solid product. $^1$H NMR (300 MHz, DMSO-$d_6$) δ: 4.30 (t, 2H), 4.17 (s, 2H), 3.13 (s, 3H).

Example 48: Preparation of Sulfydrylpolyethylene Glycol Carboxylic Acid (3.5 K) (T5-3)

HS-PEG-COOH      T5-3

To a reaction flask, 2.1 g (0.6 mmol) of polyethylene glycol methyl carboxylate-monohydroxymethanesulfonate (3.5 K) and 274 mg (3.6 mmol) of thiourea were added, and 30 mL of absolute ethanol was added thereto. The resulting mixture was refluxed overnight. The reaction mixture was concentrated, added with 30 mL of water, and transferred to a three-necked flask, which was protected with nitrogen gas. 278 mg (1.8 mmol) of DTT and sodium hydroxide solution Scheme 5

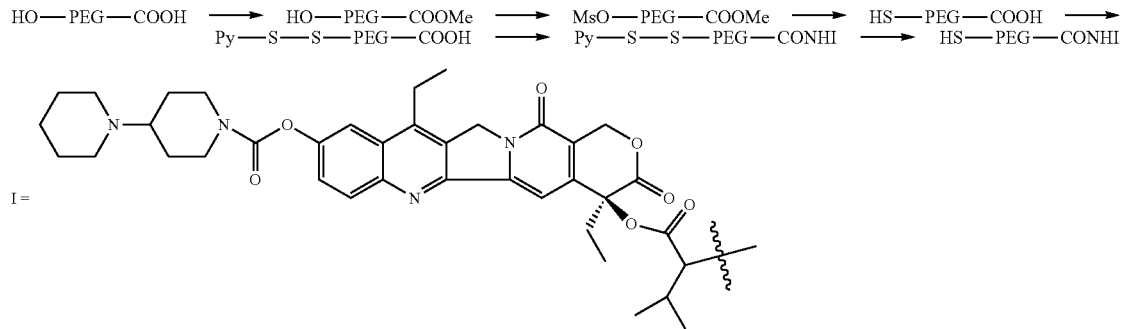

Example 46: Preparation of Hydroxypolyethylene Glycol Methyl Carboxylate (3.5 K) (T5-1)

HO-PEG-COOMe      T5-1

50 g of monohydroxy polyethylene glycol carboxylic acid (3.5 K) was dissolved in methanol, and thionyl chloride was added dropwise thereto. After the completion of the dropwise addition, the resulting mixture was further reacted under stirring at room temperature for 3 h. The reaction mixture was concentrated. The residue was dissolved with isopropanol under heating, and cooled to precipitate a solid, and filtered. The obtained filter cake was dried under vacuum overnight to give a white solid product. $^1$H NMR (300 MHz, DMSO-$d_6$) δ: 4.55 (t, 1H), 4.12 (s, 2H), 3.31 (s, 3H).

Example 47: Preparation of Polyethylene Glycol Methyl Carboxylate-Monohydroxymethanesulfonate (3.5 K) (T5-2)

MsO-PEG-COOMe      T5-2

45 g of polyethylene glycol methyl carboxylate-monohydroxy (5 K) was dissolved in dichloromethane, and triethwere added thereto. The resulting mixture was reacted under stirring at room temperature for 4 h. The reaction mixture was acidified and washed with ethyl acetate. The aqueous layer was extracted three times with dichloromethane. The organic phases were combined, washed with saturated brine, dried and filtered. The filtrate was concentrated, and the residue was crystallized from isopropanol and filtered. The obtained filter cake was dried to give a white solid. $^1$H NMR (300 MHz, DMSO-$d_6$) δ: 4.19 (s, 2H).

Example 49: Protection of Sulfydrylpolyethylene Glycol Carboxylic Acid (3.5 K) (T5-4)

Py-S—S-PEG-COOH      T5-4

To a reaction flask, 1.4 g (0.4 mmol) of HS-PEG-COOH and 440.3 mg (2 mmol) of Py-SS-Py were added and dissolved in methanol. The resulting mixture was reacted under stirring at room temperature overnight. The reaction mixture was concentrated to dryness. The residue was crystallized from isopropanol and filtered. The obtained filter cake was dried to give a white solid (1.2 g). $^1$H NMR (300 MHz, DMSO-$d_6$) δ: 8.57 (s, 1H), 7.66 (s, 1H), 7.29 (s, 1H), 7.24 (s, 1H), 4.19 (s, 2H).

Example 50: Preparation of Py-S—S-PEG-CONHI (3.5 K) (T5-5)

Py-S—S-PEG-CONHI    T5-5

To a reaction flask, 1.7 g (0.486 mmol) of Py-SS-PEG-COOH, 1.19 g (1.457 mmol) of valine irinotecan ester trifluoroacetate and 131 mg (0.971 mmol) of HOBt were added and dissolved in dichloromethane. Further, 760 μL (4.371 mmol) of diisopropylethylamine was added thereto. The resulting mixture was stirred well. 186.1 mg (0.971 mmol) of EDCI was added thereto. After the completion of the addition, the resulting mixture was stirred at room temperature overnight. The reaction mixture was concentrated to dryness. The residue was crystallized from isopropanol and filtered. The obtained filter cake was dried to give a white solid (1.5 g). $^1$H NMR (300 MHz, DMSO-$d_6$) δ: 8.57 (s, 1H), 8.09 (d, 1H), 7.92 (d, 1H), 7.67 (m, 2H), 7.43 (m, 1H), 7.29 (s, 1H), 7.24 (s, 1H), 7.12 (s, 1H), 5.37 (s, 2H), 5.03 (s, 2H), 4.35-4.22 (m, 3H), 4.19 (s, 2H), 4.07 (s, 6H), 3.81-3.49 (m, 150H), 3.13 (s, 3H), 2.86-2.67 (m, 3H), 2.35 (m, 4H), 2.28 (d, 1H), 2.09-1.98 (m, 2H), 1.76-1.53 (m, 10H), 1.31 (s, 9H), 0.91 (m, 9H).

Example 51: Preparation of SH-PEG-CONHI (3.5 K) (T5-6)

HS-PEG-CONHI

SH-PEG3.5K—CONHI    T5-6

1.5 g (0.428 mmol) of the starting material Py-S—S-PEG-CONHI was dissolved in dichloromethane, and DTT and triethylamine were added thereto. The resulting mixture was stirred at room temperature overnight. The reaction mixture was concentrated to dryness. The residue was crystallized from isopropanol and filtered. The obtained filter cake was dried to give a white solid (1.1 g). $^1$H NMR (300 MHz, DMSO-$d_6$) δ: 8.09 (d, 1H), 7.92 (d, 1H), 7.67 (m, 1H), 7.43 (m, 1H), 7.12 (s, 1H), 5.37 (s, 2H), 5.03 (s, 2H), 4.35-4.22 (m, 3H), 4.19 (s, 2H), 4.07 (s, 6H), 3.81-3.49 (m, 150H), 3.13 (s, 3H), 2.86-2.67 (m, 3H), 2.35 (m, 4H), 2.28 (d, 1H), 2.09-1.98 (m, 2H), 1.76-1.53 (m, 10H), 1.31 (s, 9H), 0.91 (m, 9H).

Example 52: Preparation of SH-PEG6-CONHI

The starting material SH-PEG6-COOH was purchased from Biomatrik Inc., and the rest of the synthesis process was referred to Examples 49 to 51.

The reactions in Examples 53 to 58 are shown in Scheme 6.

Preparation of SH-PEG-(CONHI)$_7$

Example 53: Preparation of Hydroxypolyethylene Glycol Methyl Heptacarboxylate (5 K) (T6-1)

HO-PEG-(COOMe)$_7$    T6-1

50 g of monohydroxypolyethylene glycol heptacarboxylic acid (5 K) was dissolved in methanol, and thionyl chloride was added dropwise thereto. After the completion of the dropwise addition, the resulting mixture was further reacted under stirring at room temperature for 3 h. The reaction mixture was concentrated to dryness to give a product. $^1$H NMR (300 MHz, DMSO-$d_6$) δ: 4.55 (t, 1H), 4.12 (s, 14H), 3.31 (s, 21H).

Example 54: Preparation of Polyethylene Glycol Methyl Heptacarboxylate-Monohydroxymethanesulfonate (5 K) (T6-2)

MsO-PEG-COOMe)$_7$    T6-2

45 g of polyethylene glycol methyl heptacarboxylate-monohydroxy (5 K) was dissolved in dichloromethane, and triethylamine was added thereto. The resulting mixture was stirred well. Methanesulfonyl chloride was further added dropwise thereto. After the completion of the dropwise addition, the resulting mixture was further reacted under stirring at room temperature overnight. The reaction mixture was concentrated to dryness to give a product. $^1$H NMR (300 MHz, DMSO-$d_6$) δ: 4.30 (t, 2H), 4.17 (s, 14H), 3.31 (s, 21H), 3.13 (s, 3H).

Example 55: Preparation of Sulfydrylpolyethylene Glycol Heptacarboxylic Acid (5 K) (T6-3)

HS-PEG-(COOH)$_7$    T6-3

To a reaction flask, 3.0 g (0.6 mmol) of polyethylene glycol methyl hexacarboxylate-monohydroxymethanesulfonate (5 K) and 274 mg (3.6 mmol) of thiourea were added, and 30 mL of absolute ethanol was added thereto. The resulting mixture was refluxed overnight. The reaction mixture was concentrated, added with 30 mL of water, and transferred to a three-necked flask, which was protected with nitrogen gas. 278 mg (1.8 mmol) of DTT and sodium hydroxide solution were added thereto. The resulting mixture was reacted under stirring at room temperature for 4 h. The reaction mixture was acidified and washed with ethyl acetate. The aqueous layer was extracted three times with dichloromethane. The organic phases were combined, washed with saturated brine, dried and filtered. The filtrate was concentrated to dryness to give a product. $^1$H NMR (300 MHz, DMSO-$d_6$) δ: 4.19 (s, 14H).

Scheme 6

HO—PEG—(COOH)$_7$ ⟶ HO—PEG—(COOMe)$_7$ ⟶ MsO—PEG—(COOMe)$_7$ ⟶ HS—PEG—(COOMe)$_7$ ⟶
Py—S—S—PEG—(COOMe)$_7$ ⟶ Py—S—S—PEG—(CONHI)$_7$ ⟶ HS—PEG—(CONHI)$_7$

I =

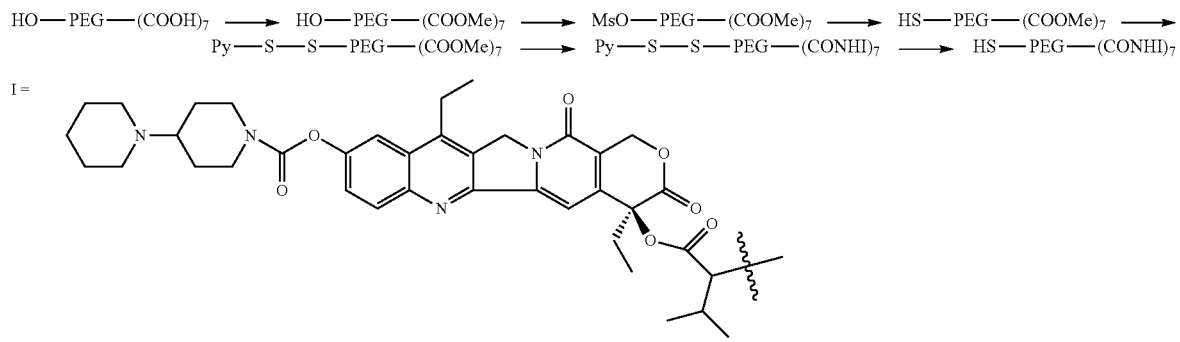

Example 56: Protection of Sulfydrylpolyethylene Glycol Heptacarboxylic Acid (5 K) (T6-4)

Py-S—S PEG-(COOH)₇   T6-4

To a reaction flask, 2.0 g (0.4 mmol) of HS-PEG-(COOH)₇ and 440.3 mg (2 mmol) of Py-S—S-Py were added and dissolved in methanol. The resulting mixture was reacted under stirring at room temperature overnight. The reaction mixture was concentrated to dryness to give a product. ¹H NMR (300 MHz, DMSO-d₆) δ: 8.57 (s, 1H), 7.66 (s, 1H), 7.29 (s, 1H), 7.24 (s, 1H), 4.19 (s, 14H).

Example 57: Preparation of Py-S—S-PEG-(CONHI)₇(5 K) (T6-5)

Py-S—S-PEG-(CONHI)₇   T6-5

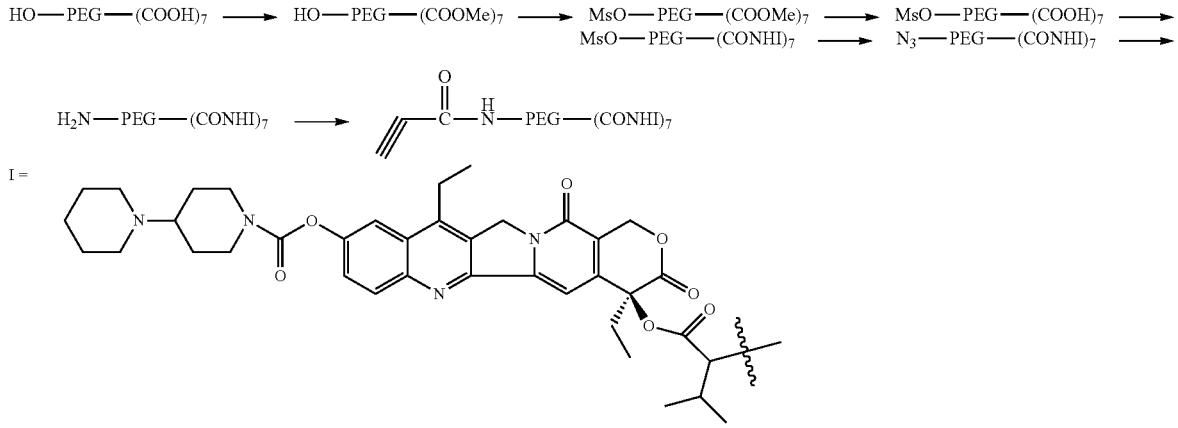

I =

To a reaction flask, 2.5 g (0.5 mmol) of Py-SS-PEG-(COOH)₇, 4.3 g (5.25 mmol) of valine irinotecan ester trifluoroacetate and 932 mg (7 mmol) of HOBt were added and dissolved in dichloromethane, and then 1.8 mL (10.5 mmol) of diisopropylethylamine was added thereto. The resulting mixture was stirred well. 1.34 g (7 mmol) of EDCI was added thereto. After the completion of the addition, the resulting mixture was reacted under stirring at room temperature overnight. The reaction mixture was concentrated to dryness to give a product. ¹H NMR (300 MHz, DMSO-d₆) δ: 8.57 (s, 1H), 8.09 (d, 7H), 7.92 (d, 7H), 7.67 (m, 8H), 7.43 (m, 7H), 7.29 (s, 1H), 7.24 (s, 1H), 7.12 (s, 7H), 5.37 (s, 14H), 5.03 (s, 14H), 4.35-4.22 (m, 21H), 4.19 (s, 14H), 4.07 (s, 14H), 3.13 (s, 3H), 2.86-2.67 (m, 21H), 2.35 (m, 8H), 2.28 (d, 7H), 2.09-1.98 (m, 14H), 1.76-1.53 (m, 70H), 1.31 (s, 21H), 0.91 (m, 21H).

Example 58: Preparation of SH-PEG-(CONHI)₇(5K) (T6-6)

HS-PEG-(CONHI)₇

HS-8ARM-PEG(5K)—(CONHI)₇   T6-6

1.5 g (0.3 mmol) of the starting material Py-S—S-PEG-(CONHI)₇ was dissolved in dichloromethane, and DTT and triethylamine were added thereto. The resulting mixture was reacted under stirring at room temperature overnight. The reaction mixture was concentrated to dryness to give a product. ¹H NMR (300 MHz, DMSO-d₆) δ: 8.09 (d, 7H), 7.92 (d, 7H), 7.67 (m, 7H), 7.43 (m, 7H), 7.12 (s, 7H), 5.37 (s, 14H), 5.03 (s, 14H), 4.35-4.22 (m, 21H), 4.19 (s, 14H), 4.07 (s, 14H), 3.13 (s, 21H), 2.86-2.67 (m, 21H), 2.35 (m, 4H), 2.28 (d, 7H), 2.09-1.98 (m, 14H), 1.76-1.53 (m, 70H), 1.31 (s, 21H), 0.91 (m, 21H).

The reactions in Examples 59 to 65 are shown in Scheme 7.

Preparation of Alkynyl-PEG-(CONHI)₇

Scheme 7

HO—PEG—(COOH)₇ ⟶ HO—PEG—(COOMe)₇ ⟶ MsO—PEG—(COOMe)₇ ⟶ MsO—PEG—(COOH)₇ ⟶ MsO—PEG—(CONHI)₇ ⟶ N₃—PEG—(CONHI)₇ ⟶ H₂N—PEG—(CONHI)₇ ⟶ HC≡C—C(O)—NH—PEG—(CONHI)₇

Example 59: Preparation of Hydroxypolyethylene Glycol Methyl Carboxylate (5 K)

The preparation was the same as that in Example 54.

Example 60: Preparation of Polyethylene Glycol Methyl Heptacarboxylate-Monohydroxymethanesulfonate (5 K)

The preparation was the same as that in Example 55.

Example 61: Preparation of MsO-PEG-(COOH)₇ (5 K) (T7-1)

MsO-PEG-(COOH)₇   T7-1

3.0 g (0.6 mmol) of polyethylene glycol methyl hexacarboxylate-monohydroxymethanesulfonate (5 K) was dissolved in methanol, and 1 N sodium hydroxide solution was added thereto. The system was heated to reflux for 3 h. The reaction mixture was cooled, then acidified with dilute hydrochloric acid, and concentrated under reduced pressure. The residue was added with water and extracted with dichloromethane. The extract was washed with saturated brine, dried and filtered. The filtrate was concentrated to dryness to give a product. ¹H NMR (300 MHz, DMSO-d₆) δ: 3.13 (s, 3H, CH₂OSO₂CH₃), 4.01 (s, 14H).

Example 62: Preparation of MsO-PEG-(CONHI)₇ (5 K) (T7-2)

MsO-PEG-(CONHI)₇    T7-2

To a reaction flask, 2.5 g (0.5 mmol) of MsO-PEG-(COOH)₇, 4.3 g (5.25 mmol) of valine irinotecan ester trifluoroacetate and 932 mg (7 mmol) of HOBt were added and dissolved in dichloromethane, and then 1.8 mL (10.5 mmol) of diisopropylethylamine was added thereto. The resulting mixture was stirred well. 1.34 g (7 mmol) of EDCI was added thereto. After the completion of the addition, the resulting mixture was stirred at room temperature overnight. The reaction mixture was concentrated to dryness to give a product. $^1$H NMR (300 MHz, DMSO-d₆) δ: 8.09 (d, 7H), 7.92 (d, 7H), 7.67 (m, 7H), 7.43 (m, 7H), 7.12 (s, 7H), 5.37 (s, 14H), 5.03 (s, 14H), 4.35-4.22 (m, 21H), 4.19 (s, 14H), 4.07 (s, 14H), 3.13 (s, 3H), 2.86-2.67 (m, 21H), 2.35 (m, 8H), 2.28 (d, 7H), 2.09-1.98 (m, 14H), 1.76-1.53 (m, 70H), 1.31 (s, 21H), 0.91 (m, 42H).

Example 63: Preparation of N₃-PEG-(CONHI)₇ (5 K) (T7-3)

N₃-PEG-(CONHI)₇    T7-3

MsO-PEG-(CONHI)₇ (5 K) was dissolved in DMF, and sodium azide was added thereto. The system was heated to 90° C. for 3 h. The reaction mixture was cooled and then recrystallized from isopropanol to give a product. $^1$H NMR (300 MHz, DMSO-d₆) δ: 8.07 (d, 7H), 7.93 (d, 21H), 7.65 (dd, 21H), 7.44 (m, 21H), 7.15 (s, 21H), 5.38 (s, 14H), 5.04 (s, 14H), 4.36-4.24 (m, 28H), 4.05 (s, 42H), 2.88-2.69 (m, 21H), 2.33 (m, 28H), 2.25 (d, 7H), 2.11-1.96 (m, 14H), 1.77-1.54 (m, 70H), 1.32 (s, 21H), 0.92 (m, 42H).

Example 64: Preparation of NH₂-PEG-(CONHI)₇ (5 K) (T7-4)

NH₂-PEG-(CONHI)₇    T7-4

NH₂-PEG-(CONHI)₇ (5 K) was dissolved in dichloromethane, and triphenyl phosphine was added thereto. The resulting mixture was reacted at room temperature overnight. The reaction mixture was concentrated to dryness to give a product. $^1$H NMR (300 MHz, DMSO-d₆) δ: 8.07 (d, 7H), 7.93 (d, 21H), 7.65 (dd, 21H), 7.44 (m, 21H), 7.15 (s, 21H), 5.38 (s, 14H), 5.04 (s, 14H), 4.36-4.24 (m, 28H), 4.05 (s, 42H), 2.88-2.69 (m, 21H), 2.33 (m, 28H), 2.25 (d, 7H), 2.11-1.96 (m, 14H), 1.77-1.54 (m, 70H), 1.32 (s, 21H), 0.92 (m, 42H).

Example 65: Preparation of HC≡CCONH-PEG-(CONHI)₇ (5 K) (T7-5)

HC≡CCONH-PEG-(CONHI)₇    T7-5

Propargylic acid was dissolved in dichloromethane (500 mL), and NH₂-PEG-(CONHI)₇ (5K) and DMAP were added thereto. Under nitrogen protection, the resulting mixture was cooled and added dropwise with a solution of EDC (12.80 g, 66.6 mmol) in dichloromethane (280 mL). After the completion of the dropwise addition, the ice bath was removed. The system was naturally warmed to room temperature and reacted overnight. When the HPLC monitoring showed that the macromolecular starting material was completely reacted, the reaction mixture was concentrated to dryness to give a product. $^1$H NMR (300 MHz, DMSO-d₆) δ: 8.33 (s, 1H), 8.07 (d, 7H), 7.93 (d, 21H), 7.65 (dd, 21H), 7.44 (m, 21H), 7.15 (s, 21H), 5.38 (s, 14H), 5.04 (s, 14H), 4.36-4.24 (m, 28H), 4.05 (s, 42H), 2.88-2.69 (m, 22H), 2.33 (m, 28H), 2.25 (d, 7H), 2.11-1.96 (m, 14H), 1.77-1.54 (m, 70H), 1.32 (s, 21H), 0.92 (m, 42H).

The reactions in Examples 66 to 67 are as shown in Scheme 8.

Scheme 8

HO—PEG—COOH → HO—PEG—COOMe →
MsO—PEG—COOMe → HS—PEG—COOH →

Py—S—S—PEG—COOH →

Py—S—S—PEG—CONHR →

HS—PEG—CONHR

R =

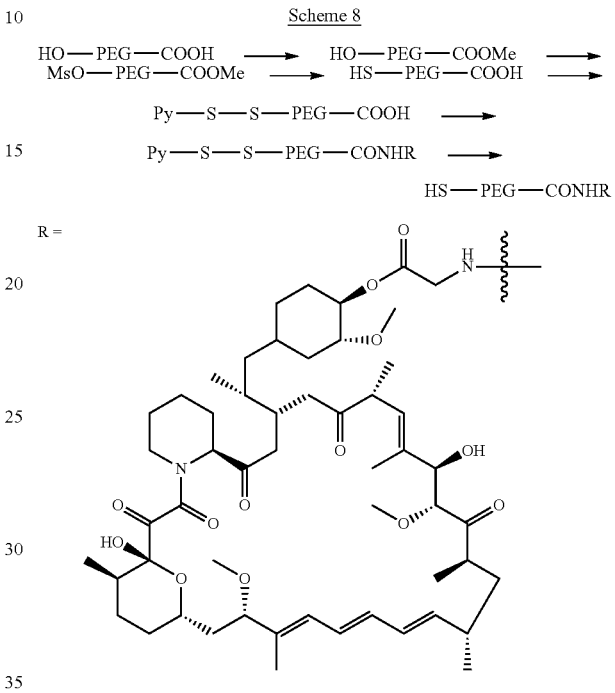

The glycine rapamycin ester of the present invention was prepared in accordance with the prior art (CN201410715522.X).

Example 66: Preparation of Py-S—S-PEG-CONHR (5 K) (T8-1)

Py-S—S-PEG-CONHR    T8-1

To a reaction flask, Py-S—S-PEG-COOH (1.75 g, 0.5 mmoL), glycine rapamycin ester (970 mg, 1 mmoL), 1-hydroxybenzotriazole (HOBt, 68 mg, 0.5 mmoL) and DMAP (122 mg, 1 mmoL) were added and dissolved in dichloromethane. The resulting mixture was cooled in an ice bath and then added dropwise with a solution of DCC (155 mg, 0.75 mmoL) in dichloromethane. After the completion of the dropwise addition, the resulting mixture was naturally warmed to room temperature and reacted overnight. On the next day, the reaction mixture was concentrated, and the residue was crystallized from isopropanol to give a white solid (1.4 g). $^1$H-NMR (300 MHz, CDCl₃): 0.90 (Me, 3H, 43), 0.92 (Me, 3H, 49), 0.94 (Me, 3H, 46), 0.96 (Me, 3H, 48), 0.97 (Me, 3H, 45), 1.10 (CH₂, 2H, 24), 1.11 (CH₂, 2H, 36), 1.20 (CH₂, 2H, 42), 1.33 (CH₂, 2H, 41), 1.37 (CH, 1H, 37), 1.45 (CH₂, 2H, 5), 1.47 (CH₂, 2H, 4), 1.60 (CH₂, 2H, 13), 1.61 (CH₂, 2H, 12), 1.65 (CH₂, 2H, 15), 1.65 (CH₂, 2H, 44), 1.74 (Me, 3H, 47), 1.75 (CH, 1H, 35), 2.07 (CH, 4H, 3, 11, 23, 25), 2.08 (CH₂, 2H, 33), 3.14 (Me, 3H, 50), 3.33 (CH, 1H, 31), 3.36 (Me, 3H, 51), 3.37 (CH₂, 2H, 6), 3.42 (CH, 1H, 40), 3.44 (Me, 3H, 52), 3.56 (CH, 1H, 39), 3.64 (CH₂, 1800H, PEG), 3.71 (CH, 1H, 16), 3.72 (CH, 1H, 27), 3.86 (CH, 1H, 14), 4.17 (CH$_2$, 2H, 54), 4.19 (CH, 1H, 28), 5.16 (CH, 1H, 2), 5.17 (CH, 1H, 34), 5.29 (=CH, 1H, 30), 5.39 (=CH, 1H, 22), 5.95 (=CH, 1H, 18), 6.13 (=CH, 1H, 21), 6.31 (=CH, 1H, 20), 6.38 (=CH, 1H, 19), 7.23 (—Py, 1H), 7.29 (—Py, 1H), 7.67 (—Py, 1H), 8.34 (CH, 1H, 55), 8.62 (—Py, 1H).

Example 67: Preparation of SH-PEG-CONHR (5 K) (T8-2)

HS-PEG-CONHR  T8-2

1.4 g (0.4 mmol) of the starting material Py-S—S-PEG-CONHR was dissolved in dichloromethane, and DTT and triethylamine were added thereto. The resulting mixture was stirred at room temperature overnight. The reaction mixture was concentrated to dryness. The residue was crystallized from isopropanol filtered. The obtained filter cake was dried to give a white solid. $^1$H-NMR (300 MHz, CDCl$_3$): 0.90 (Me, 3H, 43), 0.92 (Me, 3H, 49), 0.94 (Me, 3H, 46), 0.96 (Me, 3H, 48), 0.97 (Me, 3H, 45), 1.10 (CH$_2$, 2H, 24), 1.11 (CH$_2$, 2H, 36), 1.20 (CH$_2$, 2H, 42), 1.33 (CH$_2$, 2H, 41), 1.37 (CH, 1H, 37), 1.45 (CH$_2$, 2H, 5), 1.47 (CH$_2$, 2H, 4), 1.60 (CH$_2$, 2H, 13), 1.61 (CH$_2$, 2H, 12), 1.65 (CH$_2$, 2H, 15), 1.65 (CH$_2$, 2H, 44), 1.74 (Me, 3H, 47), 1.75 (CH, 1H, 35), 2.07 (CH, 4H, 3, 11, 23, 25), 2.08 (CH$_2$, 2H, 33), 3.14 (Me, 3H, 50), 3.33 (CH, 1H, 31), 3.36 (Me, 3H, 51), 3.37 (CH$_2$, 2H, 6), 3.42 (CH, 1H, 40), 3.44 (Me, 3H, 52), 3.56 (CH, 1H, 39), 3.64 (CH$_2$, 1800H, PEG), 3.71 (CH, 1H, 16), 3.72 (CH, 1H, 27), 3.86 (CH, 1H, 14), 4.17 (CH$_2$, 2H, 54), 4.19 (CH, 1H, 28), 5.16 (CH, 1H, 2), 5.17 (CH, 1H, 34), 5.29 (=CH, 1H, 30), 5.39 (=CH, 1H, 22), 5.95 (=CH, 1H, 18), 6.13 (=CH, 1H, 21), 6.31 (=CH, 1H, 20), 6.38 (=CH, 1H, 19), 8.34 (CH, 1H, 55).

Examples of Coupling

Example 68: Preparation of Ligand Drug Conjugate (APEGA-2) of Formula (II) (TM-[PEG-1A]-[PEG-2A]-Drug)

Wherein, the A is a maleimido-sulfydryl system, PEG1 is (MAL)3-4ARM-PEG(5K)—NHS (Example 9), PEG2 is HS-PEG(3.5K)—CONHI (Example 51), TM is a recombinant anti-HER2 humanized monoclonal antibody, and I is irinotecan.

Step 1, Synthesis of Ligand Drug Conjugate of Formula (II)—the First Step Coupling The starting materials were fed in accordance with a molar ratio of antibody to [PEG-1] of 1:60. 40 μL (200 μg) of PEG1 solution having a concentration of 100 mg/mL (prepared with 1 mM HCl) was quickly added to a coupling buffer system (50 mM sodium phosphate, pH 6.0, 50 mM sodium chloride, 1 mM EDTA) containing 1.0 mg of antibody (42 μL of 24.5 mg/mL antibody was added to 118 μL of the coupling buffer). The resulting mixture was reacted under gently shaking at room temperature for 2 hours, and then stored at −20° C. to terminate the reaction.

Step 2, Purification and Coupling for Removing Unmodified Antibody Molecule

Primary coupling purification: The coupling reaction group was diluted 4 times, and then purified by cation exchange chromatography, and the breakthrough peak and the elution peak (unmodified antibody and PEG-antibody conjugate with a low coupling degree) were collected. The breakthrough peak was cryopreserved; and the elution peak was diluted 4 times and concentrated and then refrigerated overnight for secondary coupling, and the preparation method was referred to step 1.

Secondary coupling purification: The coupling reaction group was purified by cation exchange chromatography, and the breakthrough peak and the elution peak (unmodified antibody and PEG-antibody conjugate with a low coupling degree) were collected. The breakthrough peak was cryopreserved; and the elution peak was diluted 4 times and concentrated and then refrigerated overnight for tertiary coupling, and the preparation method was referred to step 1.

Tertiary coupling purification: The tertiary coupling reaction group was purified by cation exchange chromatography, and the breakthrough peak was collected and combined with the breakthrough peaks collected in the primary and secondary coupling.

Treatment of breakthrough peak: The combined breakthrough peak was concentrated to an antibody concentration of 5.0 mg/ml for the second step coupling.

Step 3, the Second Step Coupling: Reaction for Coupling with [PEG-2]

The starting materials were fed in accordance with a molar ratio of [PEG-1] to [PEG-2] of 1:1. 40 μL of PEG2 solution having a concentration of 42 mg/mL (prepared with 1 mM HCl) was quickly added to a coupling solution (80 μL) of the PEG1-antibody coupling reaction solution (1:60). The resulting mixture was reacted under gently shaking at room temperature for 2 hours, and then stored at −20° C. to terminate the reaction. The free PEG2 molecule was removed by ultrafiltration, and the solution was replaced with a solution containing 50 mM PB and 97 mM NaCl (pH 6.0). The resulting solution was further sterilized through filtration to obtain a conjugate.

Example 69: Preparation of Antibody Drug Conjugate (APEGA-4) of Formula (II) (TM-[PEG-1A]-[PEG-2A]-Drug)

Wherein, the A is a maleimido-sulfydryl system, PEG1 is (MAL)3-4ARMPEG5K—NHS (Example 9), PEG2 is SH-4ARMPEG5K—(CONHI)3 (Example 39), TM is a recombinant anti-HER2 humanized monoclonal antibody, and I is irinotecan. The preparation method was referred to Example 68.

Example 70: Preparation of Antibody Drug Conjugate (APEGA-5) of Formula (II) (TM-[PEG-1A]-[PEG-2A]-Drug)

Wherein, the A is a maleimido-sulfydryl system, PEG1 is (MAL) 3-4ARMPEG(5K)—NHS (Example 9), PEG2 is HS-8ARM-PEG(5K)—(CONHI)$_7$ (Example 58), TM is a recombinant anti-HER2 humanized monoclonal antibody, and I is irinotecan. The preparation method was referred to Example 68.

Example 71: Preparation of Antibody Drug Conjugate (APEGA-6) of Formula (II) (TM-[PEG-1A]-[PEG-2A]-Drug)

Wherein, the A is a maleimido-sulfydryl system, PEG1 is (MAL) 7-8ARM-PEG(5K)—NHS (Example 15), PEG2 is SH-4ARMPEG5K—(CONHI)3 (Example 39), TM is a recombinant anti-HER2 humanized monoclonal antibody, and I is irinotecan. The preparation method was mainly referred to Example 68 except that the coupling buffer system was a solution containing 50 mM sodium phosphate, pH 7.2, 50 mM sodium chloride, and 1 mM EDTA.

Example 72: Determination of Antibody Content of Antibody Drug Conjugates in Examples 68, 69, 70, and 71

Method: UV/Vis Method

In formula (1), the sum of the absorbances of a drug and an antibody at 280 nm constitutes the total absorbance ($A_{280}$):

$$A_{280} = (\varepsilon_{drug}^{280} C_{drug} + \varepsilon_{mAb}^{280} C_{mAb}) 1 \quad (1)$$

In the formula, $\varepsilon_{drug}^{280}$ is the extinction coefficient of the drug at 280 nm; $C_{drug}$ is the concentration of the drug (mg/ml); $\varepsilon_{mAb}^{280}$ is the extinction coefficient of the antibody at 280 nm; and $C_{mAb}$ is the concentration of the antibody.

Equation (2) is a parallel equation for the total absorbance of the drug at the maximum absorption $\lambda(D)$:

$$A_{\lambda(D)} = (\varepsilon_{drug}^{\lambda(D)} C_{drug} + \varepsilon_{mAb}^{\lambda(D)} C_{mAb}) 1 \quad (2)$$

In the formula, $\varepsilon_{drug}^{\lambda(D)}$ is the extinction coefficient of the drug at $\lambda(D)$ nm; $C_{drug}$ is the concentration of the drug; $\varepsilon_{mAb}^{\lambda(D)}$ is the extinction coefficient of the antibody at $\lambda(D)$ nm; and $C_{mAb}$ is the concentration of the antibody (mg/ml).

The concentration of antibody and drug can be calculated separately by the above two equations.

$$C_{mAb} = (A_{280} \varepsilon_{drug}^{\lambda(D)} - A_{\lambda(D)} \varepsilon_{drug}^{280}) / [(\varepsilon_{mAb}^{280} \varepsilon_{drug}^{\lambda(D)} - \varepsilon_{mAb}^{\lambda(D)} \varepsilon_{drug}^{280}) 1]$$

$$C_{drug} = (A_{280} \varepsilon_{mAb}^{\lambda(D)} - A_{\lambda(D)} \varepsilon_{mAb}^{280}) / [(\varepsilon_{drug}^{280} \varepsilon_{mAb}^{\lambda(D)} - \varepsilon_{drug}^{\lambda(D)} \varepsilon_{mAb}^{280}) 1]$$

The average drug antibody coupling ratio (DAR) is calculated by dividing $$\frac{C_{drug}}{Mr_{drug}} \text{ by } \frac{C_{mAb}}{Mr_{mAb}},$$

expressed as the number of moles of the drug divided by the number of moles of the antibody:

$$DAR = \frac{C_{drug} \times Mr_{mAb}}{C_{mAb} \times Mr_{drug}}$$

The results are shown in Table 1.

TABLE 1

Quantitative summary of two-step coupling products by UV-Vis

| Sample | $C_{drug}$ (mg/ml) | $C_{mAb}$ (mg/ml) | DAR | $\lambda$ (254) | $\lambda$ (280) |
|---|---|---|---|---|---|
| APEGA-2 (4ARM + 1ARM) | 0.288 | 0.058 | 14.3 | 1.78 | 0.414 |
| APEGA-4 (4ARM + 4ARM) | 0.281 | 0.037 | 56.8 | 1.724 | 0.372 |
| APEGA-5 (4ARM + 8ARM) | 0.229 | 0.093 | 125.5 | 1.444 | 0.405 |
| APEGA-6 (8ARM + 4ARM) | 0.080 | 0.217 | 114.2 | 0.614 | 0.44 |

Example 73: Preparation of Antibody Conjugate of Formula (II) (TM-[PEG-1A]-[PEG-2A]-Drug)

Wherein, the A is a maleimido-sulfydryl system, PEG1 is (MAL)3-4ARM-PEG(5K)—NHS (Example 9), PEG2 is HS-PEG(3.5K)—CONHR (Example 51), TM is a recombinant anti-CD3 humanized monoclonal antibody (organ transplant rejection- and autoimmune disease-associated antibody), and R is rapamycin (used for prophylaxis and treatment of renal transplant rejection). The preparation method was referred to Example 68.

Example 74: Determination of Antibody Content of Antibody Drug Conjugate in Example 73

The method for determining the antibody content was the same as Example 72. The detection results are shown in Table 2.

TABLE 2

Quantitative summary of two-step coupling products by UV-Vis

| Sample | $C_{drug}$ (mg/ml) | $C_{mAb}$ (mg/ml) | DAR | $\lambda$ (267) | $\lambda$ (280) |
|---|---|---|---|---|---|
| APEGA-1R (4ARM + 1ARM) | 0.086 | 0.24 | 14.3 | 0.639 | 0.491 |

Example 75: Preparation of Antibody Drug Conjugate of Formula (II) (TM-[PEG-1A]-[PEG-2A]-Drug)

Wherein, the A is a maleimido-sulfydryl system, PEG1 is (MAL)3-PEG12-NHS (Example 26), PEG2 is SH-PEG6-CONHI (Example 52), TM is a recombinant anti-HER2 humanized monoclonal antibody, and I is irinotecan. The preparation method was referred to Example 68.

Example 76: Determination of Antibody Content of Antibody Drug Conjugate in Example 75

The method for determining the antibody content was the same as that in Example 72. The detection results are shown in Table 3.

TABLE 3

Quantitative summary of two-step coupling products by UV-Vis

| Sample | $C_{drug}$ (mg/ml) | $C_{mAb}$ (mg/ml) | DAR | $\lambda$ (254) | $\lambda$ (280) |
|---|---|---|---|---|---|
| APEGA-7 (4ARM + 1ARM) | 0.081 | 0.15 | 20.4 | 0.584 | 0.340 |

Pharmacokinetics and Pharmaceutical Efficacy

Example 77: Rat Pharmacokinetic Assay of Antibody Drug Conjugates in Examples 68, 69, 70, and 71

Experimental method: SD rats were anesthetized by intraperitoneal injection of 1% pentobarbital sodium at 40 mg/kg, and then the skin behind the neck and in front of the neck was prepared and disinfected by iodophor. The skin at the right to the middle of the neck was cut open to expose the jugular vein. A venous catheter was inserted into the blood vessel and then ligated, and the skin at the opening was sutured. After the operation was completed, approximately 0.2 mL of heparin sodium solution and 0.1 mL of blocking solution were intraductally injected into the catheter, and thereafter replaced daily for a week. After a week, the rats with all the surgical wounds healed and the catheter fixed accurately and repeated blood collection unobstructed were used in the pharmacokinetic study of this project. The rats were given recombinant anti-HER2 humanized monoclonal antibody and APEGA-2, 4, 5, and 6 via tail vein respectively, and the blood of the rats were collected at the set time points after administration, and analyzed.

0.05 μg/ml human HER2 protein was coated in a microwell with 0.05 M carbonate buffer, 100 μl/well, and cultured overnight at 4° C. The plate was washed with 400 μL of PBST, blocked with 300 μL of blocking solution at 37° C. for 1 h, and then washed with 400 μL of PBST. The standard and the samples to be tested were added to the above-mentioned coated reaction wells, 100 μl/well, and incubated at 37° C. for 1 hour. The wells were then washed. Addition of enzyme-labeled antibody: Each reaction well was added with a goat anti-human IgG enzyme-labeled antibody, 100 μl/well, and incubated at 37° C. for 1 hour, and then washed. Addition of substrate solution for color development: Each reaction well was added with a temporarily prepared TMB substrate solution, 50 μl/well, and incubated at 37° C. for 15-30 minutes. Termination of reaction: Each reaction well was added with 2 M sulfuric acid, 50 μl/well. The absorbance was measured at 450 nm on an ELISA detector. The regression equation was obtained by linear regression using the absorbance value of the standard corresponding to the absorbance value (excluding the blank). The concentration of the antibody in the sample to be tested was obtained by substituting the absorbance value of the sample to be tested (excluding the blank) into the standard curve equation.

Experimental results: The results are shown in FIG. 1. This experiment confirmed that after the drug was conjugated, the elimination rate of each sample was increased to some extent compared with the recombinant anti-HER2 humanized monoclonal antibody, but the downward trend was not very significant.

Example 78: Pharmacodynamic Test of Antibody Drug Conjugates in Examples 68, 69, 70, and Method: The pharmaceutical efficacy of the samples was evaluated using the N87 gastric cancer model and the SKOV-3 ovarian cancer model with high expression of HER2. The cell line in the logarithmic growth phase was inoculated subcutaneously into the right side of the immunodeficient mice with an inoculation amount of $5 \times 10^6$ cells/mouse. After the transplanted tumor was formed, it was passed through the mice for 2 generations for use. The tumor tissue in the vigorous growth period was cut into tumor pieces with a diameter of about 2 mm and inoculated subcutaneously into the right torso of nude mice or NOD/SCID mice under aseptic conditions. The diameter of the formed tumor tissue was measured by a vernier caliper, and the long and short diameters are represented by a and b, respectively. The tumor volume (TV) was calculated as: $TV = \frac{1}{2} \times a \times b^2$. After the tumors were grown to 100-150 mm$^3$, the animals were randomly grouped. Both models included vehicle group, positive control group (recombinant anti-HER2 humanized monoclonal antibody, 30 mg/kg) and tested sample group (APEGA-2, 4, 5, and 6 were given, respectively, at a dose of 30 mg/kg, based on recombinant anti-HER2 humanized monoclonal antibody). Both the tested sample and the control drug were administered once a week in the tail vein for a total of four doses. The diameter of the transplanted tumor was measured twice a week during the entire experiment, and the body weight of the mice was weighed. After the end of the administration, the animals were sacrificed after two weeks of observation.

Figure 2:
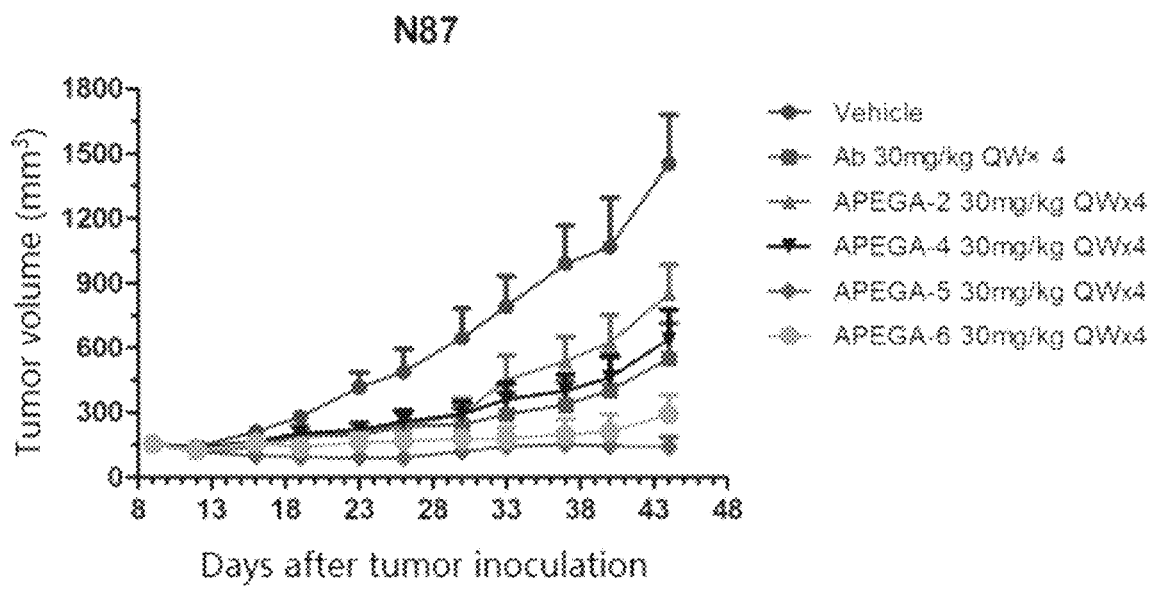
FIG. 2 is a graph showing the mean tumor volume of the gastric cancer model (NCI-N87) corresponding to the number of days after tumor transplantation, with an injection dose of 30 mg/kg. Ab: unmodified antibody; APEGA-2: antibody-drug conjugate (four-arm+single-arm); APEGA-4: antibody-drug conjugate (four-arm+four-arm); APEGA-5: antibody-drug conjugate (four-arm+eight-arm); and APEGA-6: antibody-drug conjugate (eight-arm+four-arm).
Figure 3:
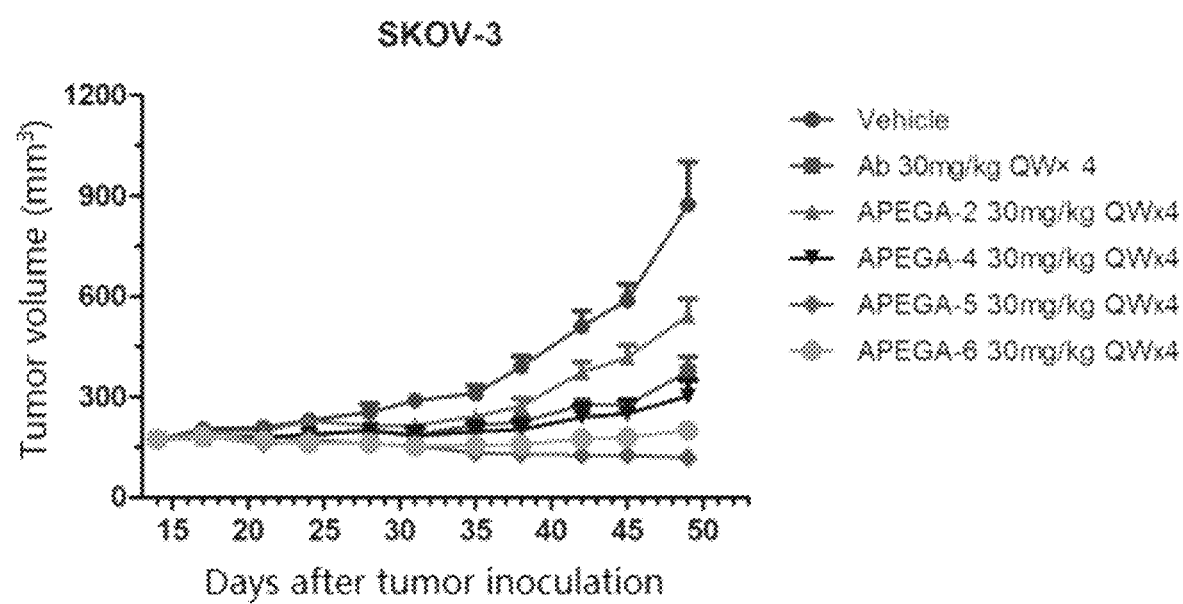
FIG. 3 is a graph showing the mean tumor volume of the ovarian cancer model (SKOV-3) corresponding to the number of days after tumor transplantation, with an injection dose of 30 mg/kg. Ab: unmodified antibody; APEGA-2: antibody-drug conjugate (four-arm+single-arm); APEGA-4: antibody-drug conjugate (four-arm+four-arm); APEGA-5.

Experimental results: The experimental results are shown in FIG. 2, Table 4, and FIG. 3, Table 5.

TABLE 4

Comparison of tumor inhibition rates of different tested samples in the gastric cancer model (NCI-N87) in the fifth week of administration

| Tested sample | Tumor inhibition rate (%) |
| --- | --- |
| Ab 30 mg/kg QW × 4 | 62.1 |
| APEGA-2 30 mg/kg QW × 4 | 41.3 |
| APEGA-4 30 mg/kg QW × 4 | 56.0 |
| APEGA-5 30 mg/kg QW × 4 | 90.4 |
| APEGA-6 30 mg/kg QW × 4 | 80.0 |

TABLE 5

Comparison of tumor inhibition rates of different tested samples in the ovarian cancer model (SKOV-3) in the fifth week of administration

| Tested sample | Tumor inhibition rate (%) |
| --- | --- |
| Ab 30 mg/kg QW × 4 | 57.2 |
| APEGA-2 30 mg/kg QW × 4 | 37.9 |
| APEGA-4 30 mg/kg QW × 4 | 65.4 |
| APEGA-5 30 mg/kg QW × 4 | 86.4 |
| APEGA-6 30 mg/kg QW × 4 | 77.1 |

The results showed that the tested samples, APEGA-5 and APEGA-6, showed significant anti-tumor activity in both tumor models and had a significantly better pharmaceutical efficacy then the recombinant anti-HER2 humanized monoclonal antibody of the same dose and dosage regimen. Wherein, APEGA-5 had stronger anticancer activity and was better than APEGA-6 in both models. The other two tested samples, APEGA-2 and APEGA-4, had relatively weak pharmaceutical efficacy. APEGA-2 had weaker pharmaceutical efficacy in both models than recombinant anti-HER2 humanized monoclonal antibody, and APEGA-4 had a pharmaceutical efficacy similar to the recombinant anti-HER2 humanized monoclonal antibody. During the whole experiment, the animals were not observed to have obvious abnormal reactions, which had better drug tolerance.

The invention claimed is:

1. A ligand drug conjugate or a pharmaceutically acceptable salt thereof
    wherein,
    the ligand drug conjugate is selected from the group consisting of APEGA-2, APEGA-4, APEGA-5 and APEGA-6, each having the structural formula shown below:

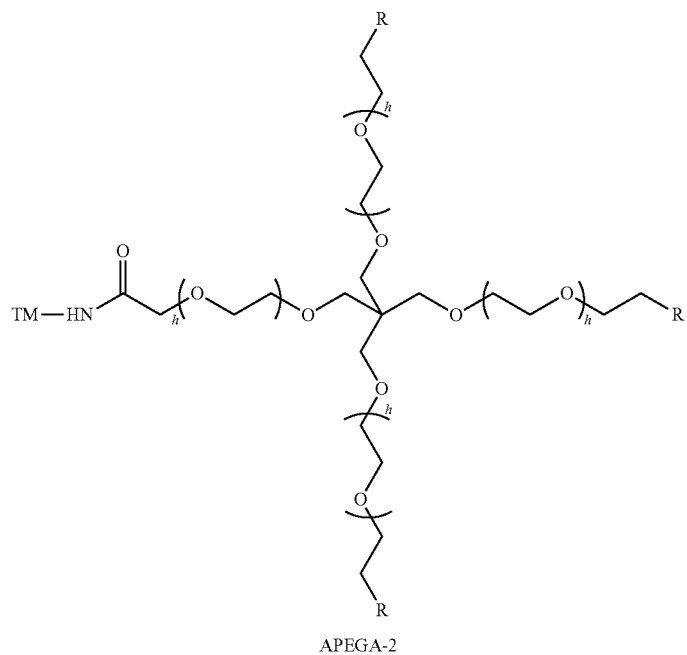
APEGA-2
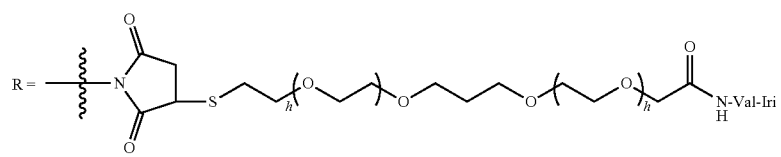
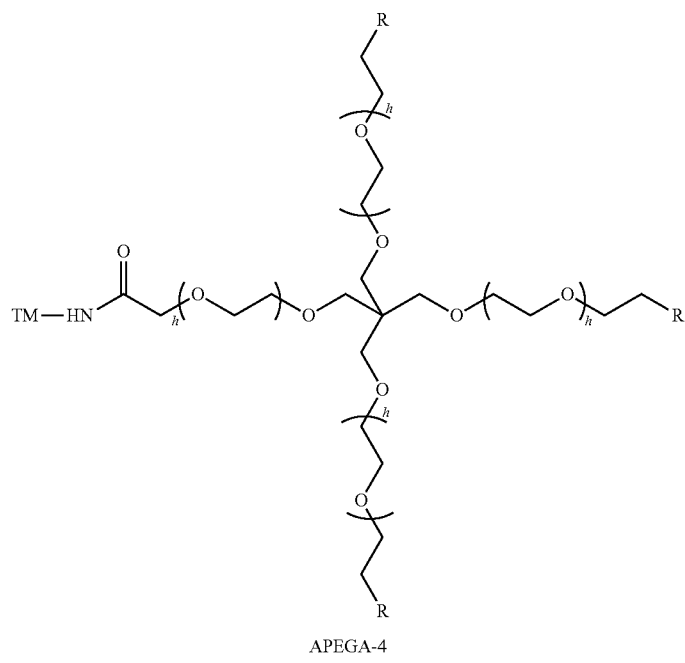
APEGA-4

-continued
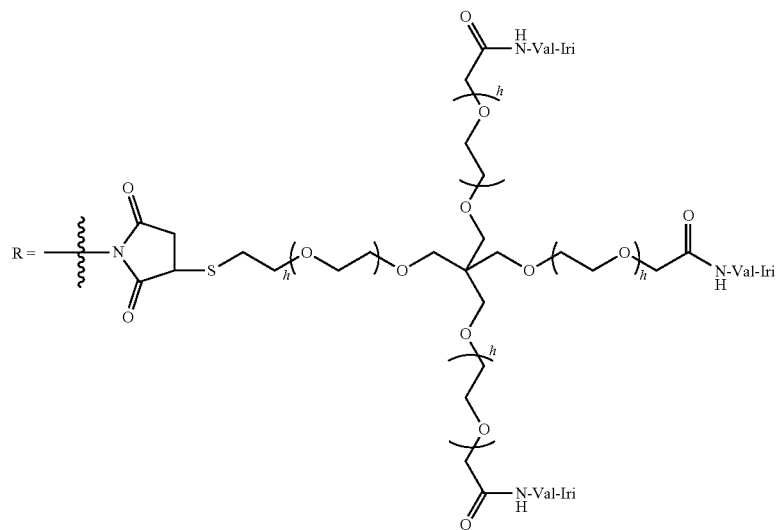
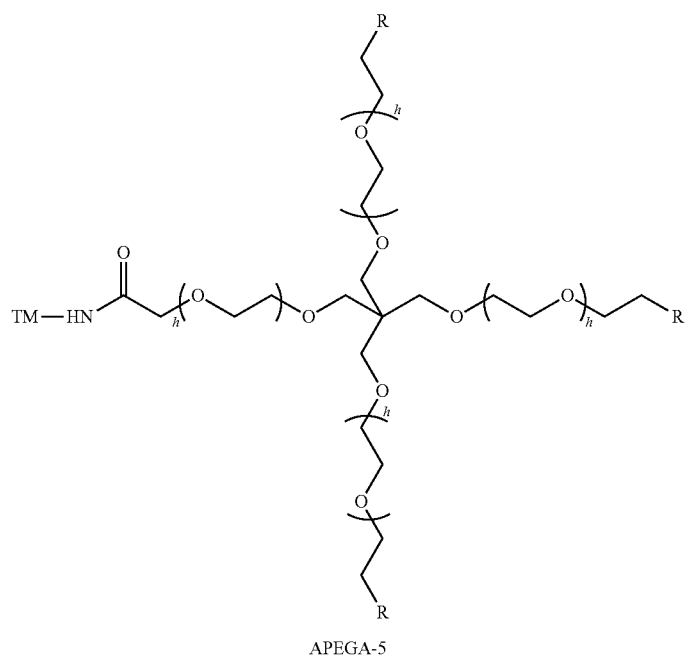
APEGA-5

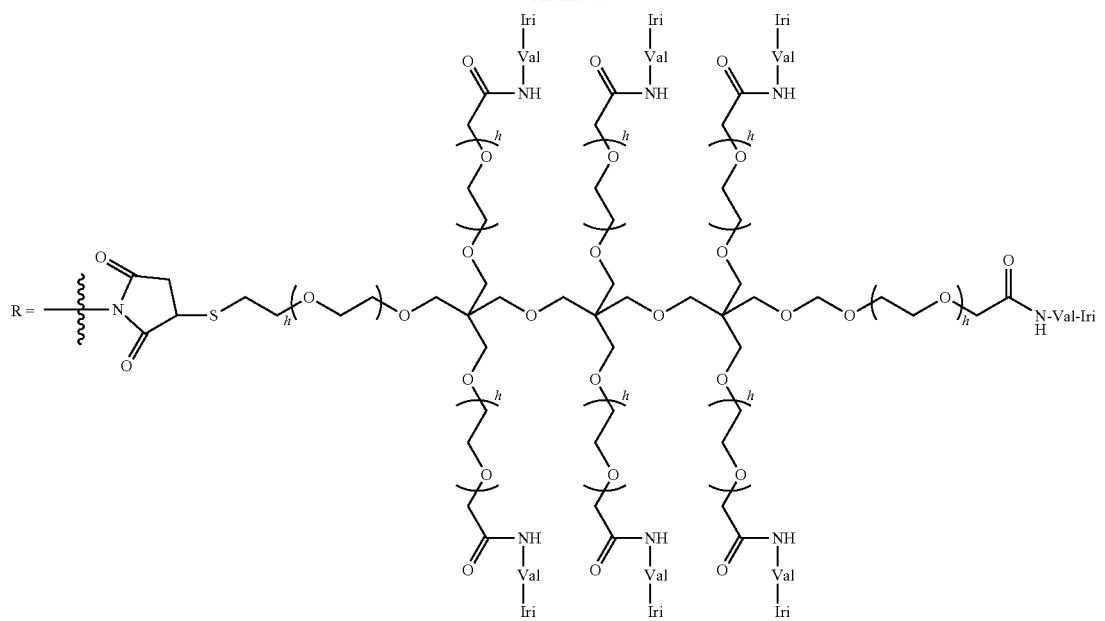
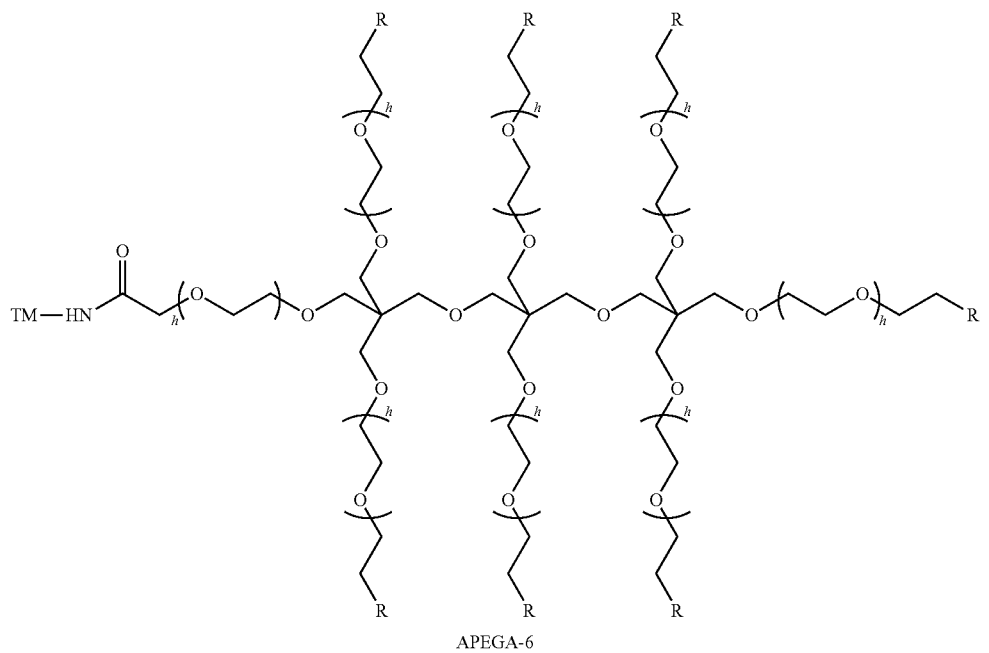
APEGA-6

-continued
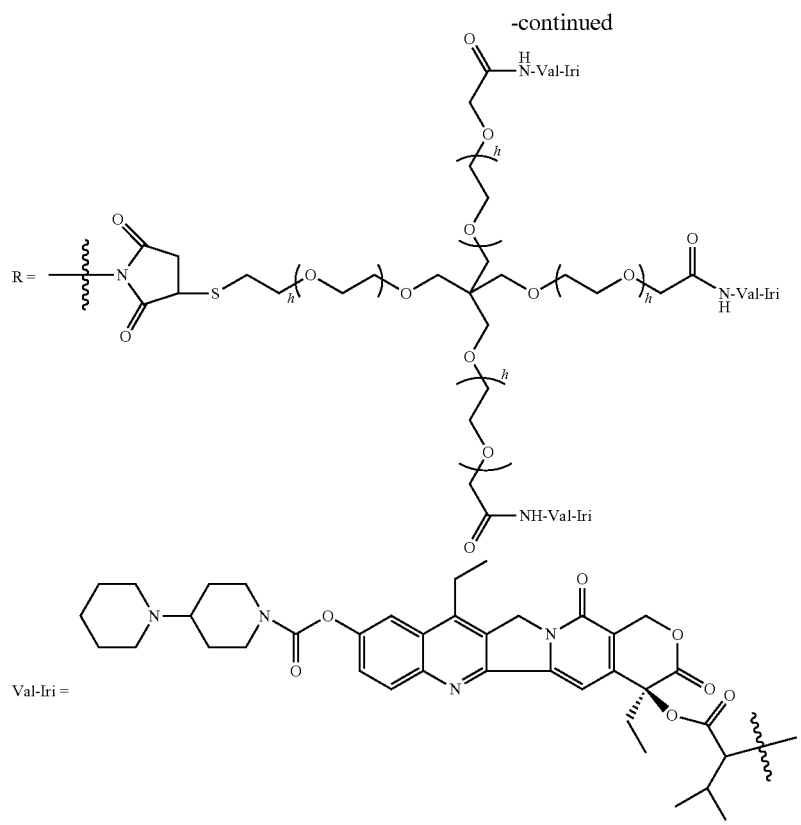
wherein, Val is proline; Iri is irinotecan; h is the same or not the same, and each independently is an integer selected from 1 to 240; TM is a ligand unit, the TM ligand unit is selected from the group consisting of a monoclonal antibody and a polyclonal antibody.
* * * * *